(12) United States Patent
Gill

(10) Patent No.: US 11,957,320 B2
(45) Date of Patent: Apr. 16, 2024

(54) IMAGE GUIDED SPINAL DECOMPRESSION WITH CONTRALATERAL OBLIQUE VIEW

(71) Applicant: Beth Israel Deaconess Medical Center, Inc., Boston, MA (US)

(72) Inventor: Jatinder S. Gill, Lincoln, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 567 days.

(21) Appl. No.: 16/823,115

(22) Filed: Mar. 18, 2020

(65) Prior Publication Data
US 2020/0281621 A1    Sep. 10, 2020

Related U.S. Application Data

(63) Continuation-in-part of application No. PCT/US2019/051155, filed on Sep. 13, 2019, which
(Continued)

(51) Int. Cl.
*A61B 17/56*    (2006.01)
*A61B 1/00*    (2006.01)
(Continued)

(52) U.S. Cl.
CPC ........ *A61B 1/3135* (2013.01); *A61B 1/00094* (2013.01); *A61B 1/009* (2022.02);
(Continued)

(58) Field of Classification Search
CPC ........ A61B 17/320016; A61B 1/00094; A61B 1/005; A61B 1/043; A61B 1/0684;
(Continued)

(56) References Cited

U.S. PATENT DOCUMENTS 4,905,670 A    3/1990 Adair
5,514,091 A    5/1996 Yoon
(Continued)

FOREIGN PATENT DOCUMENTS

CA    2441871 A1    10/2002
JP    7-80086 A    3/1995
(Continued)

OTHER PUBLICATIONS

U.S. Appl. No. 15/844,440, filed Dec. 15, 2017, 2018-0256021, Published.
(Continued)

*Primary Examiner* — Howard D Brown, Jr.
(74) *Attorney, Agent, or Firm* — McCarter & English, LLP

(57) ABSTRACT

The present invention relates to a flexible surgical system for endoscopic spinal decompression and methods thereof. Various methods of accessing the epidural space with this instrument are described. The system design enables placement of the device through several approaches. It is then advanced under direct visualization or fluoroscopic (X-Ray), for example, into areas of the spine including lumbar (low back), thoracic (mid and upper back) and cervical (neck). The pathologies encroaching upon the spinal space can then be visualized wherein the epidural membrane can optionally be displaced to further aid in visualization. The membrane can be used to protect regions of tissue adjacent the site to tissue removal.

32 Claims, 49 Drawing Sheets

Related U.S. Application Data is a continuation-in-part of application No. 15/844,440, filed on Dec. 15, 2017.

(60) Provisional application No. 62/730,874, filed on Sep. 13, 2018, provisional application No. 62/435,675, filed on Dec. 16, 2016.

(51) Int. Cl.

| | | |
|---|---|---|
| *A61B 1/005* | (2006.01) | |
| *A61B 1/04* | (2006.01) | |
| *A61B 1/06* | (2006.01) | |
| *A61B 1/313* | (2006.01) | |
| *A61B 1/32* | (2006.01) | |
| *A61B 17/32* | (2006.01) | |
| *A61B 90/00* | (2016.01) | |
| *A61B 90/30* | (2016.01) | |

(52) U.S. Cl.
CPC ............ *A61B 1/043* (2013.01); *A61B 1/0684* (2013.01); *A61B 1/32* (2013.01); *A61B 17/320016* (2013.01); *A61B 90/04* (2016.02); *A61B 90/30* (2016.02); *A61B 90/36* (2016.02); *A61B 2017/320069* (2017.08); *A61B 2017/32007* (2017.08); *A61B 2217/005* (2013.01)

(58) Field of Classification Search
CPC ......... A61B 1/3135; A61B 1/32; A61B 90/04; A61B 90/30; A61B 90/36; A61B 2017/320069; A61B 2017/32007; A61B 2217/005; A61B 5/0084; A61B 90/361; A61B 17/320068; A61B 2018/00023; A61B 2018/00166; A61B 2018/00184; A61B 2018/00196; A61B 2018/00285; A61B 2018/0044; A61B 2018/00601; A61B 2018/2266; A61B 18/22; A61B 17/3401; A61B 17/3421; A61B 2017/00685; A61B 2018/00577; A61B 2018/00625; A61B 2018/00922; A61B 2018/00928; A61B 2018/00982; A61B 2018/202; A61B 2018/20553; A61B 2018/2222; A61B 2018/2227; A61B 2018/2233; A61B 2090/0436; A61B 2090/0454; A61B 2090/049; A61B 2090/061; A61B 2090/306; A61B 2090/309; A61B 2090/3614; A61B 2090/3966; A61B 1/00082; A61B 1/00089; A61B 1/00098; A61B 1/00135; A61B 1/015; A61B 1/018; A61B 1/042; A61B 1/05; A61B 1/0669; A61B 1/0676; A61B 1/07

See application file for complete search history.

(56) References Cited

U.S. PATENT DOCUMENTS

| | | | |
|---|---|---|---|
| 5,782,800 A | 7/1998 | Yoon | |
| 6,482,235 B1 | 11/2002 | Lambrecht et al. | |
| 6,925,323 B2 | 8/2005 | Snoke | |
| 7,449,019 B2 | 11/2008 | Uchida et al. | |
| 7,553,307 B2 | 6/2009 | Bleich et al. | |
| 7,738,968 B2 | 6/2010 | Bleich | |
| 7,896,879 B2 | 3/2011 | Solsberg et al. | |
| 7,914,540 B2 | 3/2011 | Schwartz et al. | |
| 7,942,830 B2 | 5/2011 | Solsberg et al. | |
| 8,002,836 B2* | 8/2011 | Lambrecht | A61F 2/442 606/86 R |
| 8,142,479 B2 | 3/2012 | Hess | |
| 8,257,356 B2* | 9/2012 | Bleich | A61M 25/09041 606/79 |
| 8,523,909 B2 | 9/2013 | Hess | |
| 8,734,477 B2 | 5/2014 | Solsberg et al. | |
| 9,833,303 B2 | 12/2017 | Hacker et al. | |
| 9,867,600 B2 | 1/2018 | Parihar et al. | |
| 2002/0138091 A1 | 9/2002 | Pflueger | |
| 2003/0158591 A1 | 8/2003 | Brett | |
| 2006/0235452 A1 | 10/2006 | Schomer et al. | |
| 2006/0247663 A1 | 11/2006 | Schwartz et al. | |
| 2007/0255172 A1 | 11/2007 | Pflueger | |
| 2008/0103504 A1* | 5/2008 | Schmitz | A61B 17/320016 606/45 |
| 2009/0099409 A1 | 4/2009 | Luehrs et al. | |
| 2011/0098531 A1 | 4/2011 | To | |
| 2011/0160731 A1* | 6/2011 | Bleich | A61B 17/3421 606/167 |
| 2011/0190772 A1* | 8/2011 | Saadat | A61B 17/1659 606/79 |
| 2011/0288540 A1* | 11/2011 | Wright | A61B 18/1477 606/33 |
| 2011/0307064 A1 | 12/2011 | Schaller | |
| 2013/0178939 A1* | 7/2013 | Poulos | A61F 2/4611 623/17.16 |
| 2013/0226239 A1* | 8/2013 | Altarac | A61B 17/864 606/279 |
| 2014/0088577 A1 | 3/2014 | Anastassiou et al. | |
| 2015/0045891 A1* | 2/2015 | Poulos | H04W 52/0254 623/17.15 |
| 2015/0202005 A1 | 7/2015 | Fuflyigin et al. | |
| 2015/0272678 A1 | 10/2015 | Kim et al. | |
| 2018/0256021 A1 | 9/2018 | Gill | |

FOREIGN PATENT DOCUMENTS

| | | |
|---|---|---|
| JP | 9-266881 A | 10/1997 |
| KR | 10-2011-0100990 A | 9/2011 |
| WO | 2016/044640 A1 | 3/2016 |

OTHER PUBLICATIONS

Ahn et al., Use of lasers in minimally invasive spine surgery. Expert Rev Med Devices. Jun. 2018;15(6):423-433.

Biscup, Lasers in Spine Surgery . . . and Other Controversial Topics. SpineLine. pp. 21-23, Sep.-Oct. 2009.

Gill et al., Contralateral Oblique View Is Superior to the Lateral View for Lumbar Epidural Access. Pain Med. May 2016;17(5):839-850.

Laser Spine Institute, Advantages of Minimally Invasive Decompression Through Laminotomy and Foraminotomy. Retrieved online at: https://www.laserspineinstitute.com/assets/pdf/lfd_outcomes.pdf. 4 pages, Jan. 18, 2017.

Stern, Lasers in Spine Surgery: A Review. SpineLine, pp. 17-20, Sep.-Oct. 2009.

International Search Report and Written Opinion for Application No. PCT/US2019/051155, dated Dec. 4, 2019, 15 pages.

* cited by examiner

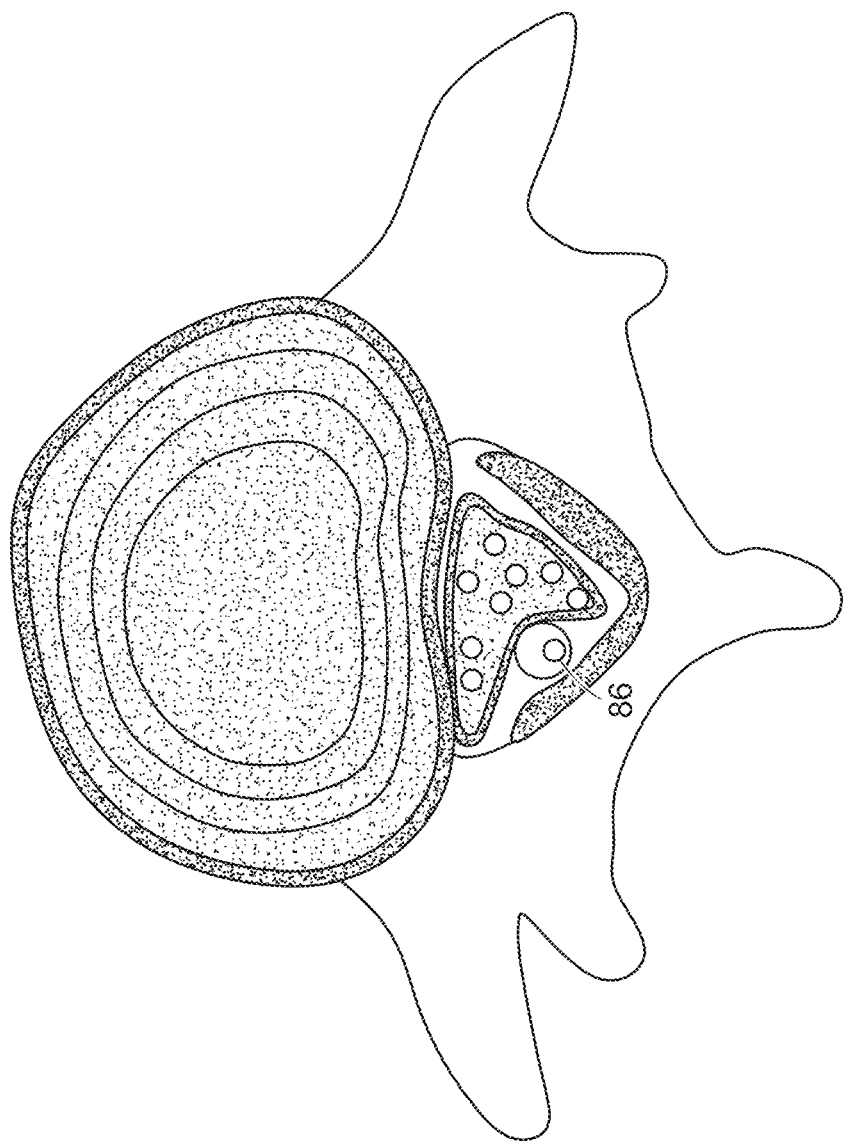
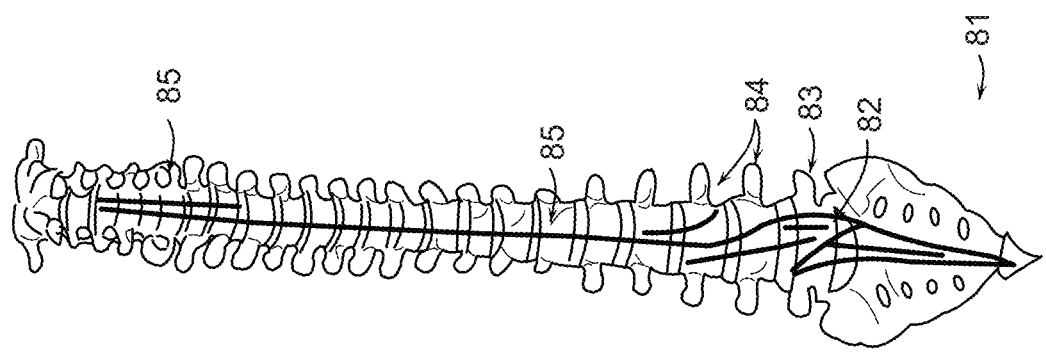
FIG. 8

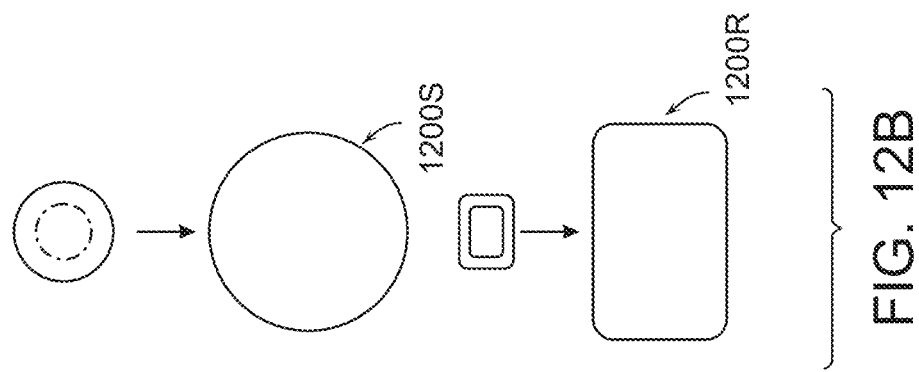
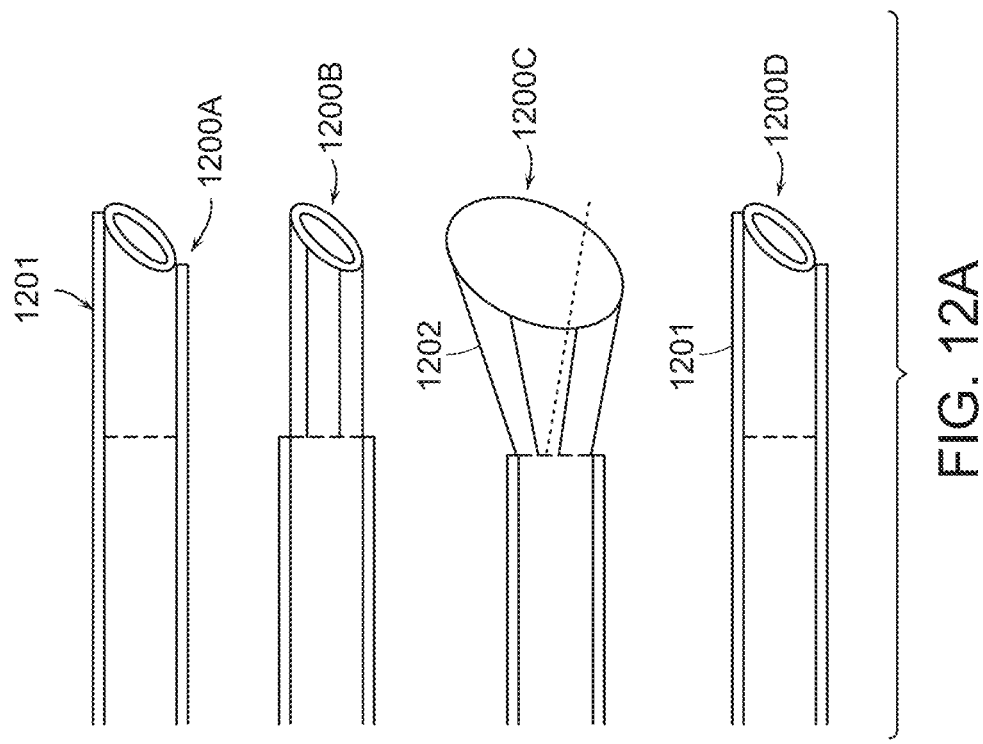

IMAGE GUIDED SPINAL DECOMPRESSION WITH CONTRALATERAL OBLIQUE VIEW

CROSS REFERENCE TO RELATED APPLICATIONS

This application is a continuation-in-part of International Patent Application No. PCT/US2019/051155, filed Sep. 13, 2019, which claims priority to U.S. Provisional Application No. 62/730,874, filed Sep. 13, 2018, and is also a continuation-in-part of U.S. application Ser. No. 15/844,440, filed Dec. 15, 2017, which claims the priority of U.S. Provisional Application No. 62/435,675, filed Dec. 16, 2016, the entire contents of each application listed above being incorporated herein by reference.

BACKGROUND OF THE INVENTION

The epidural space encloses the spinal canal and is a common area of spine pathology such as disc herniation or spinal stenosis. At the current time open surgical approaches are the only reliable method to address these conditions in the spine. Given the invasive nature of the surgery, this remains a last resort and has long term deleterious consequences. The epidural space can be accessed with needles and catheters. The role of minimally invasive epidural surgery however remains limited. This is because of technological limitations to achieve safe, precise, and adequate decompression, as the space is very small for large rigid scopes. Current minimally invasive solutions also lack advanced visualization capabilities to guide procedures. Existing procedures such as laminotomy and foraminotomy involve accessing the region of injury through the back and drilling through a portion of the lamina, for example, to provide access to the site for electrocautery or a laser fiber. These procedures remain invasive and alter the structural integrity of the spine and the epidural membrane.

Epiduroscopy may also be used in combination with a laser for ablating a disc where the resulting debris can be resorbed or manual removal of small disc fragments. The primary reason epiduroscopic surgery has not advanced involves the difficulties for visualizing the structures in the epidural space. Safety is also a concern because of collateral damage that could result in a sensitive nerve area or the possibility of damaging the wrong structure due to poor visibility.

Currently the only methods attempting visualization in the epidural space involve fluid distension, balloon neuroplasty, or a balloon cannula system. However, these methods are inadequate to support epiduroscopic surgery. It is clear from the above that there is an ongoing need for improvements in minimally invasive decompressive surgery of the spine.

SUMMARY OF THE INVENTION

The present invention addresses the problems of conventional endoscopic spinal decompression surgery by providing a flexible imaging endoscope having a diameter of 5 mm or less that provides visualization and ablation of tissue associated with a herniated disc, for example, without damaging adjacent structures. More specifically encroaching structures in the epidural space such as a herniated disc, or ligament (as seen in spinal stenosis), and other encroaching structures can be safely removed in a minimally invasive manner using a laser instrument. Devices and methods of preferred embodiments are used to displace the epidural membrane to enable visualization and ablation of a structure intruding into the epidural space.

A preferred embodiment can employ a tubular body having a working channel extending from a proximal end to a distal end in which a fiber optic device can be inserted for delivering light having an energy density sufficient to ablate tissue. The tubular body can include device elements that distend the epidural diameter to provide improved visualization. By dilating the epidural space the user can more efficiently direct pulsed laser illumination onto tissues to be removed. A lens or lens system can be used on the distal end of the fiber optic device to form a beam of light having a desired shape at a selected distance at which the tissue to be ablated is located. A beam can have a selected spot size and energy distribution suitable to remove a selected volume of tissue in response to a pulse or sequence of pulses from the laser. Due to its emission wavelength, a $CO_2$ laser is preferably used for the tissue removal process, although other lasers emitting in the infrared or near infrared portion of the electromagnetic spectrum can also be used such as a Nd:YAG or Ho:YAG lasers emitting in the range of 1400 nm to 1908 nm, for example, or light emitting diode (LED) lasers. The waveguide used for delivery of $CO_2$ laser light can employ different distal beam shaping elements to precisely define the ablation volume for each light pulse. Further embodiments can employ other tissue removal devices to access and remove spinal defects. Thus, such tissue removal devices can include a laser, an ultrasound probe to deliver energy for tissue removal, a cutting or oblation tool such as a quantum molecular resonance (QMR) probe as described in further detail herein.

A membrane can be used to deflect tissue away from the surgical space and can protect adjacent tissue from being damaged during removal of tissue from the target region. The membrane can be temporarily deployed behind the target tissue to prevent damage to underlying tissue or structure. The membrane can comprise a shape memory material that is delivered to the region in a first state and that deploys to have a different shape in a second state. The material can comprise a metal such as nitinol, a polymer, or combination thereof, which deploy in the form of a sheet they may be planar or curved to facilitate use and removal. The membrane can deflect tissue to enable transmission of energy out the spinal defect to be removed, or it can shield tissue on a front side of the membrane so that energy directed onto a spinal defect on a second side of the membrane does not damage the shielded tissue. The membrane can protect the duramater from being damaged, and/or in can protect the thecal sac, for example.

The protective membrane can also be used to protect the duramater during the treatment of spinal stenosis using contralateral oblique approach to access the tissue to be removed by a minimally invasive surgical procedure involving percutaneous insertion of a tool between the laminae connected by the ligamentum flavum that is protruding into the spinal canal across the ventral interlaminar line (VILL). In a preferred embodiment of this procedure, the protective membrane can be inserted in a direction from the base of the spine such as from the "tail bone opening" at the sacrum or from a non-treatment level to access the epidural space. A wire or catheter having the protective membrane at the distal end or along a length thereof is inserted under fluoroscopic examination to precisely position the membrane into a position between the duramater. A surgical tool can then be inserted through the narrow opening between the spinous processes from the contralateral oblique view to access the tissue to be removed and thereby decompress the spinal column. Preferred embodiments can utilize visualization with a camera to view the surgical site using the surgical tool. Depending on the location and geometry of the tissue to be removed, the protective membrane can be positioned from other access points as described herein or can occasionally the surgery can be performed without the membrane where it is not feasible or critical to insert the membrane. Maintaining an angle of the contralateral oblique view of less than 45 degrees can enable safe placement of the tool from the opposite side starting behind the ventral interlaminar line. As the contralateral oblique view can present a very small opening to access the surgical site, it can be necessary to removal bone tissue, for example, to gain entry into the interlaminal space. For many patients it can be essential to alter the axis of the surgical tool so as to deliver the cutting tool or other tissue removal instrument as described herein so as to remove the volume of tissue to decompress the spine.

A preferred embodiment uses an imaging device such as a CCD or CMOS digital imager to visualize the surgical region of interest. The imaging device preferably has at least 50,000 pixels and preferably more than 1 million pixels for high resolution imaging at video frame rates. For embodiments employing a lower resolution camera, the number of pixels can be at least 30,000 or at least 10,000. The imaging device can be mounted for positioning at the distal end of the device or a working channel within the device, or alternatively, can be optically coupled to a proximal end of a fiber optic imaging channel that can extend through the device or working channel to enable viewing of the region of interest. The imaging device can be mounted within a second tubular body in which laser light delivery system can also be mounted such that the imaging device and related optical elements are arranged to view the illuminated region of tissue. A second white light source such as one or more light emitting devices (LED) can be used to provide illumination of the small surgical field of view. The LEDs or fiber optic illumination elements can be arranged in an annular array at the distal end of the device to provide more uniform illumination.

BRIEF DESCRIPTION OF THE DRAWINGS

FIG. 8 schematically depicts the caudal, interlaminar, and transforaminal approaches for epiduroscopy.

FIGS. 12A-12B schematically depicts unstowing and stowing of the tip of the epiduroscope according to an embodiment.

FIG. 36 illustrates placement of a shield between the spinal column and the ligamentum flavum. FIG. 37 illustrates contralateral introduction of a decompression tool. FIG. 38 illustrates initial stages of removal of ligamentum flavum as the decompression tool is advanced. FIG. 39 illustrates further insertion of the decompression tool and additional removal of ligamentum flavum all the way to the vertebral body. FIG. 40 illustrates placement of the shield on the opposite lateral side and removal of ligamentum flavum by opposite contralateral insertion of the decompression tool.

FIG. 41 illustrates the expansion of the now decompressed epidural column into space vacated by the ligamentum flavum after the procedure is concluded.

DETAILED DESCRIPTION OF THE INVENTION

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Any range described herein will be understood to include the endpoints and all values between the endpoints.

Figure 1:
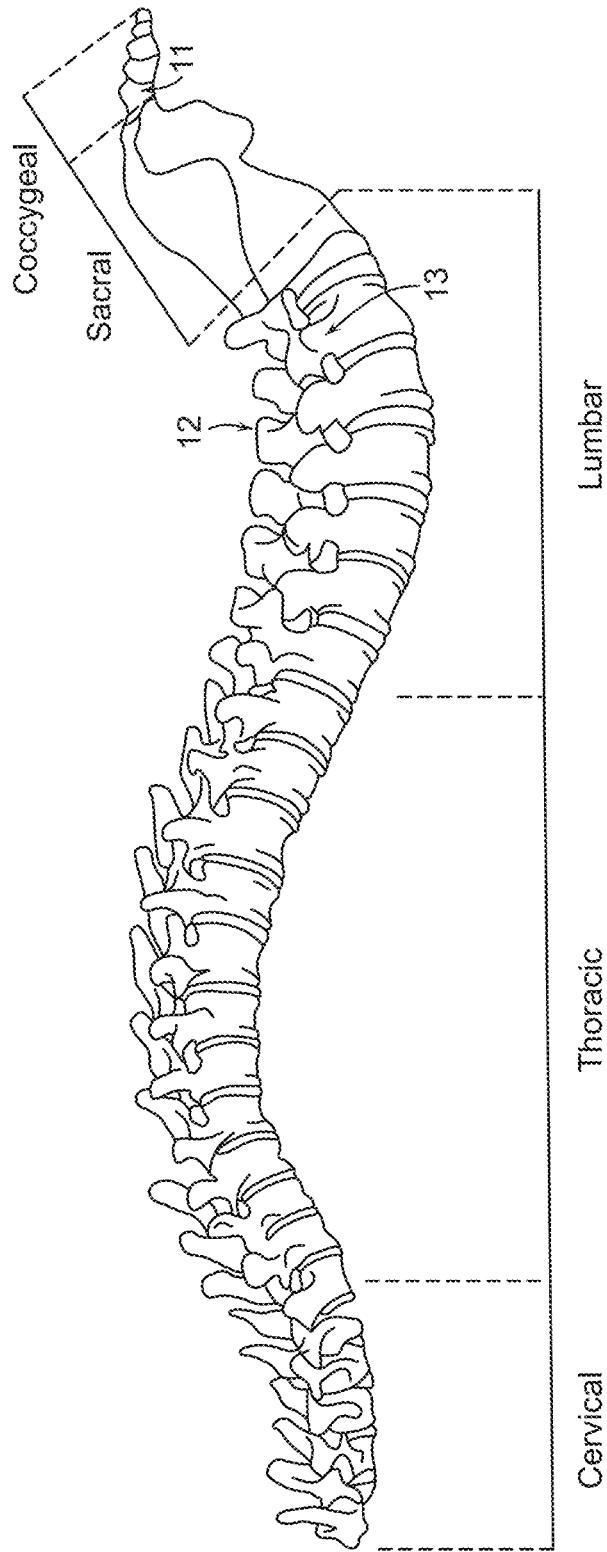
FIG. 1 is an image depicting the structure of the human spine.

The basic structural unit of the spine is a vertebra. There are 7 individual vertebrae in the neck, 12 individual vertebrae in the upper and mid back (thoracic vertebra), and five individual vertebra in the lower back (lumbar vertebra) in the human spinal column. There are nine fused vertebrae below the lumbar vertebrae, namely, the sacrum (5 fused vertebrae), and the tail bone (4 fused vertebrae). The individual vertebrae are joined to each other in the front and the back. The structure of the human spine is shown in FIG. 1 and the structure of an individual vertebra with the intervertebral disc on top is shown in FIG. 2.

The spine has 33 vertebrae (7 cervical, 12 thoracic, 5 lumbar, 5 sacral, 4 coccygeal). Preferred embodiments of an endoscopic device can be advanced into all areas of the spinal canal and may be introduced from below, via the tail bone opening 11 (sacro-coccygeal hiatus), or the back, the interlaminar opening 12, or the side, the transforaminal opening 13. The device is flexible and preferably has a diameter of less than 5 mm in diameter. The cross sectional shape can be substantially circular, oval, rectangular, ellipsoidal or a non-uniform ellipse shape, depending upon the location of percutaneous entry. Generally, the cross-sectional area of the device is less than 20 mm$^2$, is preferably less than 14 mm$^2$, and to further reduce the risk of perforation of damage to the epidural membrane surrounding features is less than 10 mm$^2$.

Figure 2:
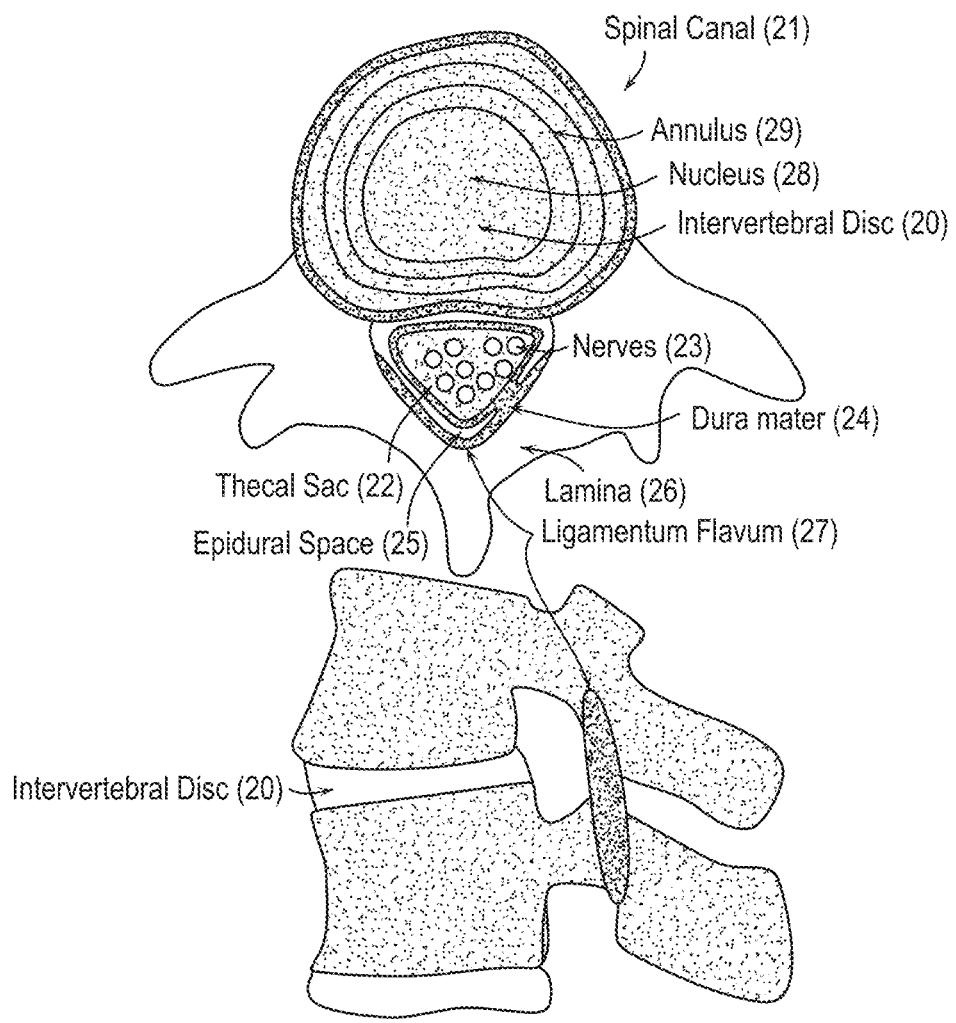
FIG. 2 schematically depicts the structure of an individual vertebra with the intervertebral disc on top.

The intervertebral disc is a cushion like structure in between the vertebrae that accommodates motion and absorbs shock as shown in FIG. 2 which schematically depicts a cross section of the spine. The intervertebral disc 20 is consequently a cushion between the vertebrae that enables freedom of movement while preserving the structure.

In the middle of the vertebra there is an opening or a hole, in the spinal canal 21. Inside the spinal canal 21 a fluid filled sac is positioned, the thecal sac 22. Inside the thecal sac 22 lie the nerves 23 and the spinal cord. The fluid in the thecal sac 23 is enclosed in a soft membrane, the duramater 24, which can be easily deformed.

The space between the duramater 24 and the bone of the vertebra is the epidural space 25. The epidural space 25 ends at the upper end of the spine and below at the base of the sacrum. Since the duramater 24 can be deformed, the epidural space 25 size may be increased manually by pushing with a mechanical device such as a balloon. The space created cannot, however, be sustained after the distending force dissipates given the outward force exerted on the duramater 24 by the fluid in the thecal sac 22.

The spinal canal 21 is a conduit for the spinal cord and the nerves 23. The margins of the spinal canal 21 are formed by the vertebral body or the disc in the front. In the back the margin is formed by the bony laminae 26 that are joined together by the ligamentum flavum 27. In the back the vertebra are attached to each other through several ligaments and joints. The ligamentum flavum 27 also connects the vertebrae in the back.

Figure 3:
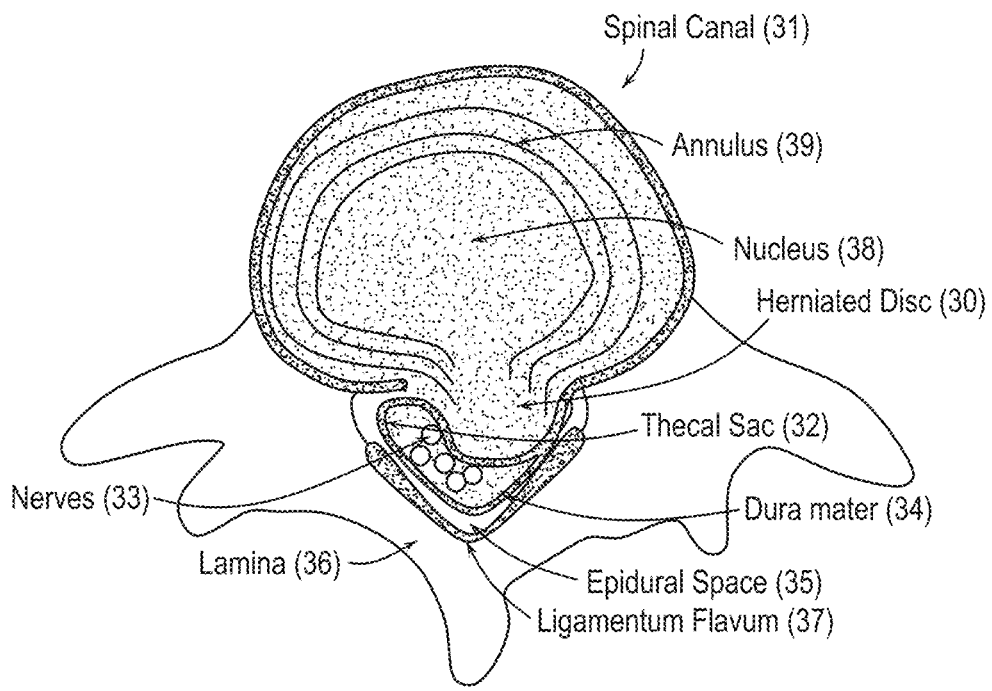
FIG. 3 schematically depicts disc herniation.

The intervertebral disc 20 is composed of a central soft gelatinous material in the center, the nucleus 38, which is enclosed in tough circumferential fibro cartilage, the disc annulus 39. With wear and tear, the disc annulus 39 may at times rupture allowing the disc to herniate or displace itself into the canal 31. FIG. 3 schematically depicts a disc herniation 30 that extends out of the disc center. The herniated disc 30 material creates severe pain because of irritation as well as pressure on the nerves and spinal cord that get impinged against the bony canal.

These may lead to neurological problems such as weakness, numbness, as well as bladder and bowel incontinence. When the pain is severe or where it does not get better with time or where the patient develops neurological problems, the only option is that of removal of the herniated disc 30 requiring a significant surgical procedure by removing the bone and overlying tissue. This may also be amenable to endoscopic removal without removing the overlying bone.

The herniated disc 30 lies in the front part of the epidural space 35. As is seen in FIG. 3, the herniated material 30 is occupying at least a portion of the spinal canal 31 and creating pressure on the nerves 33. As is also clear from FIG. 3, to remove the disc, the overlying bone and tissue need to be removed surgically. However there is another option of threading a laser device to the area of the herniated disc material 30 and removing the herniated disc material 30 by vaporizing it, as the majority of the disc material 30 comprises water. The small amount of debris can be absorbed by the body or removed by suction, for example.

Figure 4:
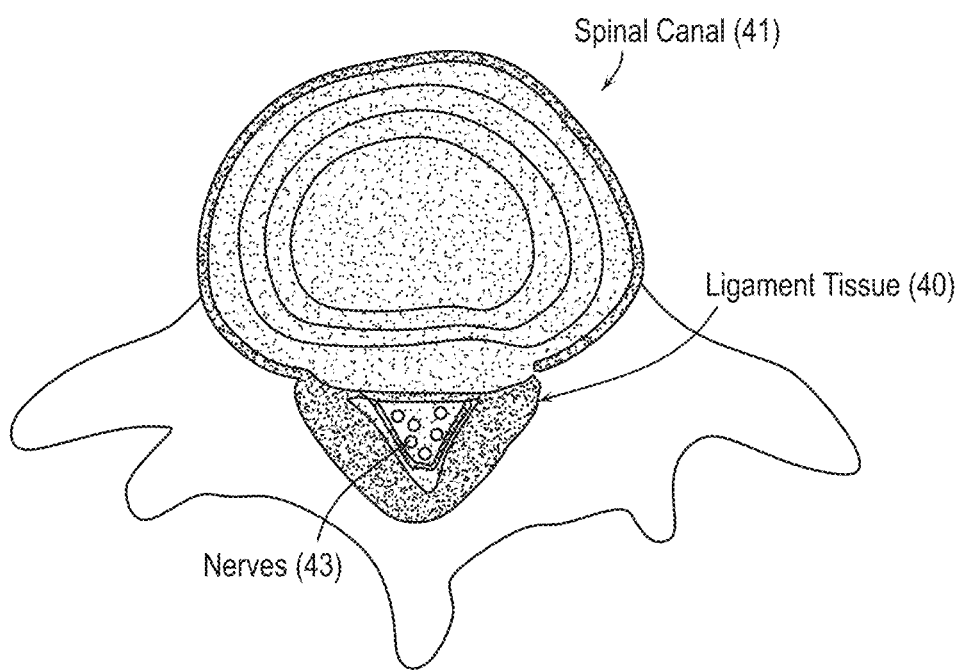
FIG. 4 schematically depicts spinal stenosis.

With aging the degenerative changes lead to bone overgrowth, and can cause soft issue overgrowth into the spinal canal 41 causing significant narrowing of the spinal canal. Some important causes of spinal stenosis include bone overgrowth, ligamentum overgrowth or disc herniation. FIG. 4 schematically depicts an example of spinal stenosis.

When there is significant narrowing of the size of the spinal canal 41 the important nerve 43 structures get pinched and their blood supply is compromised. This condition is called spinal stenosis. This leads to back and leg pain on standing and walking. If the symptoms are severe surgery is often required to create more space which is usually done by removing the bone in the back.

In FIG. 4, the cause of spinal stenosis is ligament tissue 40 overgrowth. It is clear from this figure that to remove the stenosis the overlying tissue 40 will need to be removed surgically. However there is another option of threading a laser device to the area and removing the overgrown tissue 40 and bone as necessary by vaporizing it. The small amount of debris can be absorbed by the body. The innovation in this device specifically pertains to access of the stenotic area, visualization of the region and safe ablation of the tissue 40.

Various invasive surgical methods are used when there is encroachment upon the spinal canal. For a disc herniation a discectomy can be done. The disc and some overlying bone and tissue are removed. When there is significant surgery, additional screws and plates may also be placed to fuse the bones and maintain stability of the spine. In a further embodiment removal of a disc can also be done endoscopically through a rigid tube greater than 5 mm in diameter. Epidural scopes that are smaller than 5 mm can be used for ablation of a disc, however, poor visualization has prevented such procedures.

Various minimally invasive methods are also available for the treatment of spinal stenosis. Minimally invasive lumbar decompression involves manual removal of ligamentum flavum under X-Ray visualization with rigid instruments, but is done without direct visualization.

Other methods depend on altering the biomechanics of the spine by opening up the space between the vertebra using rigid instruments such as the X-Stop® that is available from Paradigm Spine LLC, New York, NY Another minimally invasive method for diagnosis and treatment of spine conditions via the epidural space is epiduroscopy using a device called the epiduroscope. The epidural space can also be accessed with a needle.

Figure 5:
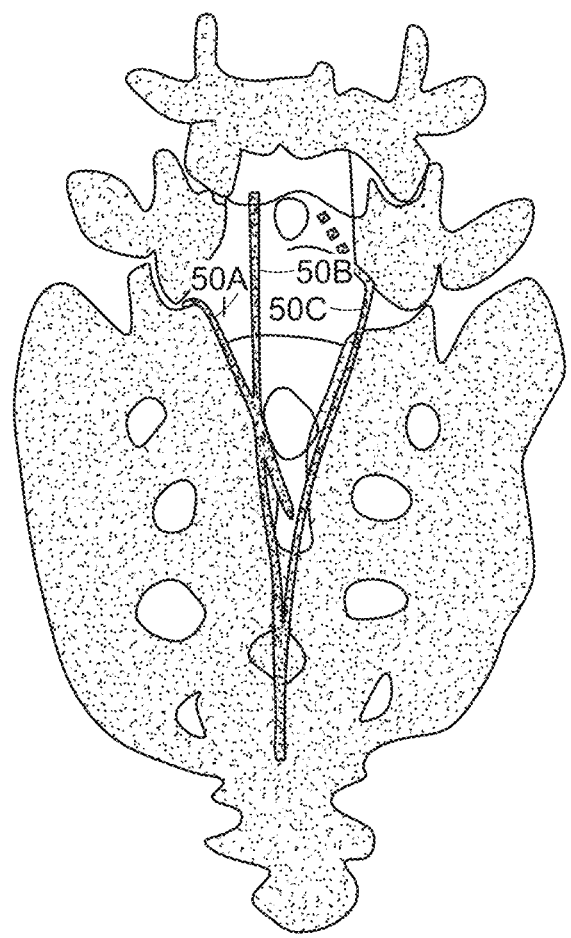
FIG. 5 schematically depicts the caudal approach for epiduroscopy.

The epidural space ends at the sacrum. The last sacral bones fail to join in the midline leaving an opening covered by skin and soft tissue. A needle may be placed through this opening to enter the epidural space, "the caudal approach" as depicted in FIG. 5. This approach is used for epiduroscopic procedures in accordance with preferred embodiments of the present invention.

For example, the epidural space and epiduroscopy may be performed by the sacral hiatus approach. Wire 50A is directed into the neural foramen for this method. Wire 50B can be directed posteriorly in the epidural space for the approach for ligamentum flavum resection for treatment of spinal stenosis. Wire 50C can be directed into the front and this approach is appropriate for removal of a herniated disc.

As an example, a needle is first inserted into the sacral hiatus at the opening at the bottom of the spine. The epidural space can be identified by loss of resistance technique. A wire can then be threaded into the epidural space. A curved wire is preferred to aid in navigation to the desired location. The semi-rigid wire (0.5 mm-2 mm in diameter) is slowly advanced by gentle direct force. The tip is directed to reach the correct compartment of the epidural space. The access device or a working channel of the epiduroscope or tubular visualization device may be then threaded over the wire to reach the area of pathology. In case of difficulty, the wire may expand by inflating like a balloon to dilate the track. Similarly dilators of different sizes may also be used sequentially to thread over the wire to create space for the access device or epiduroscope. The dilators are made of plastic or metal with variable rigidity and diameter. These may be threaded over the wire in a sequential fashion to create space for the epiduroscope, for example, when difficulty arises in threading the epiduroscope.

A probe with a working channel can be placed initially instead of the scope. Once it is threaded over the wire to the correct location the epiduroscope can slide into position within the working channel for example. Thus the diameter of the working channel can be such as to accommodate the access device or epiduroscope within it. The probe with the working channel can be flexible or semirigid with a soft rounded tip formed by a stylet placed within it. The soft rounded distal tip may be soft or semi rigid and can be shaped to facilitate displacement of the epidural membrane for a specific application. In another instance the tip of the stylet may be inflatable to dilate the tract, or distal region, within the epidural space when needed. The stylet can thus be used to initially deflect the membrane adjacent to the structure to be ablated and thereby enable visualization and treatment. As the distal end of the stylet is retracted into the working channel, the distal tip of the working channel can be translated to maintain separation of the membrane from the adjoining structure. In a further embodiment, the access device has individual lumens for imaging, laser light delivery, illumination, suction, coolant flow, fluid delivery and components may be placed in lumens individually as needed during a surgical procedure.

Figure 6:
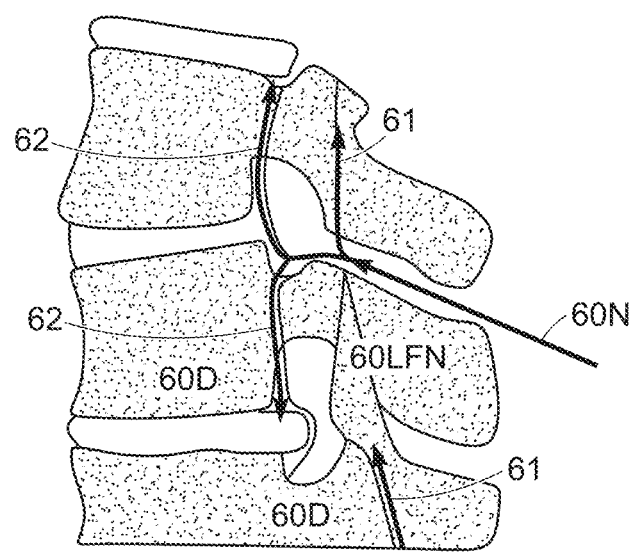
FIG. 6 schematically depicts the interlaminar approach for epiduroscopy.

The epidural space may be accessed with a needle placed in the interlaminar space and thus enters between the bones, referred to herein as "the interlaminar approach" as depicted in FIG. 6. For example, the wire is inserted into the epidural space from the back. It may then be advanced in the posterior compartment 61 of the epidural space (appropriate approach for spinal stenosis), or in the anterior compartment 62 (appropriate approach for disc herniation). The dotted line is the duramater 60D, the shaded area is the hypertrophied ligament 60LFN and the needle is represented by letter 60N.

As another example, the epidural space can be reached by threading a needle from the back. The needle may be straight or curved. The epidural space is identified by loss of resistance technique. A wire may then be threaded into the epidural space. A curved wire is preferred to facilitate proper guidance. The semi-rigid wire (0.5-2 mm in diameter) is slowly advanced by gentle direct force. The tip is directed to reach the correct compartment of the epidural space. The tip may be directed towards the head or the foot based upon where the narrowed area to be treated is located. The device or the epiduroscope can then be threaded over the wire to reach the area of pathology. In case of difficulty, the wire may expand by inflating like a balloon to dilate the track. Similarly, dilators of different sizes may also be used sequentially to thread over the wire to create space for the device.

Figure 7:
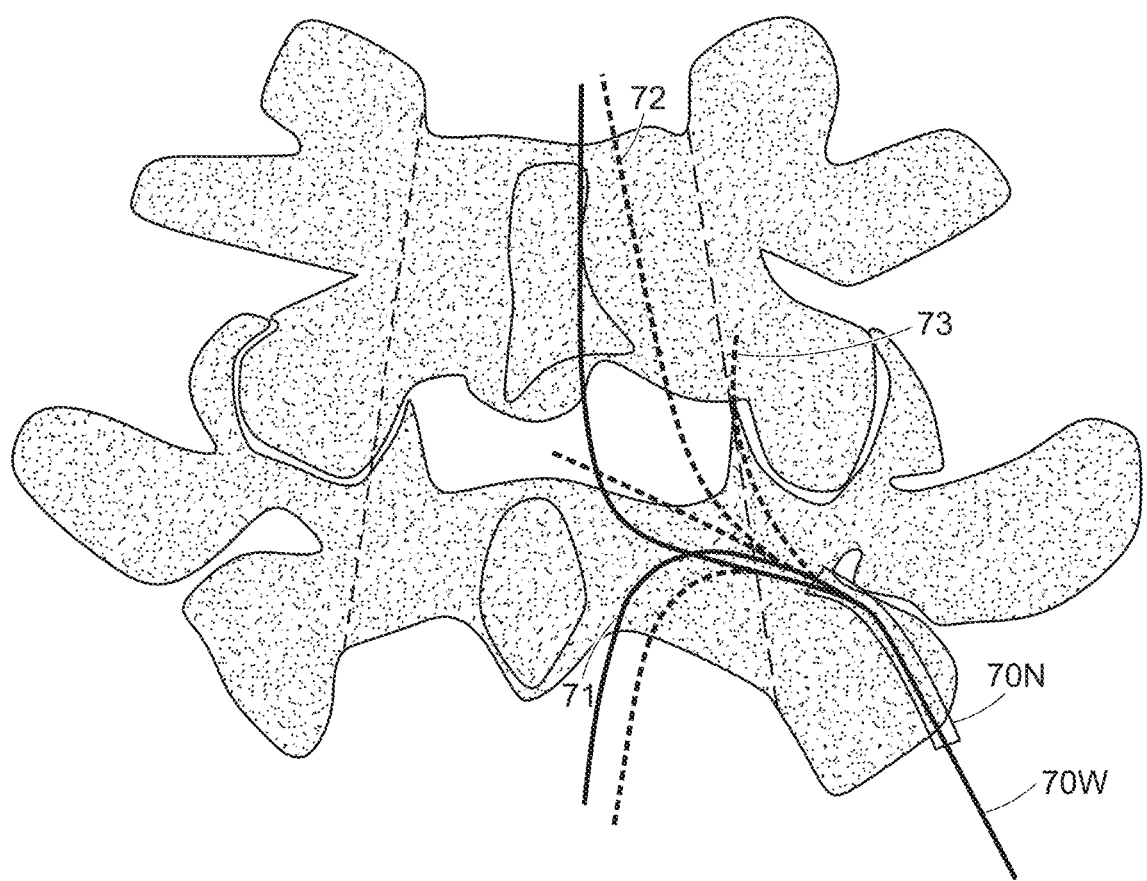
FIG. 7 schematically depicts the transforaminal approach for epiduroscopy.

On the side of the spine is an opening called the intervertebral foramen. A needle may be placed directly in the epidural space through this opening, the "transforaminal approach" as depicted in FIG. 7 which is a view from the back of the spine. The curved needle 70N is placed into the foramen from the side and the wire 70W (thick line) is advanced into the posterior epidural space 71, appropriate for ligamentum decompression or the anterior epidural space, dotted line 72 appropriate for disc herniation or the foramen, and the lateral epidural space 73 appropriate for disc herniation and foraminal decompression.

As an example, a curved needle is placed into the side opening in the spine where the nerves emerge known as the intervertebral foramen. Once the needle is placed a wire is threaded into the epidural space. Needle adjustment may be needed until the wire can be threaded. A wire may then be threaded into the epidural space. A curved wire is optimal. The semi-rigid wire (1-2 mm in diameter) is slowly advanced by gentle direct force. The tip is directed to reach the correct compartment of the epidural space. The tip may be directed towards the head or the foot based upon where the narrowed area to be treated is located. The device or a working channel may be then threaded over the wire to reach the area of pathology. In case of difficulty, the wire may expand by inflating like a balloon to dilate the track.

FIG. 8 schematically depicts various methods of entering the epidural space superimposed over a spine model. 81 represents sacral hiatus insertion, 82 represents sacral hiatus to foramen, 83 represents sacral hiatus to epidural space, 84 represents transforaminal approach to epidural space, 85 represents an interlaminar approach, 86 is a diagram of an epiduroscope in the dorsal epidural space reflecting the duramater.

During epiduroscopy semi rigid or flexible tubing with an inbuilt camera and a working channel may be used for diagnosing and treating spine conditions. It is most frequently used for removing adhesions that may form after spine surgery. The diagnostic and therapeutic utility of the method is limited and is not currently considered a part of standard treatment method and is employed infrequently. The problems relating to visualization and safe ablation continue to be problematic.

The present invention is described and made to deliver a flexible device by the interlaminar, transforaminal, or sacral route to the area of encroaching pathology in conditions such as spinal stenosis and disc herniation. The instruments and methods for accessing the area of pathology, for visualizing the pathology, protection of vulnerable tissue and removal of the pathology of concern are described in greater detail. The devices enable minimally invasive surgery of the spine by solving the problems of visualization and safety while also realizing effective decompression.

The present invention is designed to access the area of pathology in all areas of the spine, including the back and the neck. The device may be placed into the epidural space using interlaminar (back), caudal (tail bone) or transforaminal (side) approach at any level of the lumbar, thoracic and cervical spine. The device may be advanced in the anterior (front) or lateral (side) or epidural posterior (back) epidural space for pathology such as disc herniation or spinal stenosis.

Figure 9:
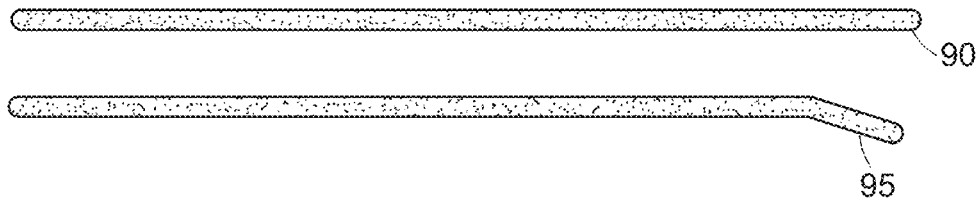
FIG. 9 depicts a straight needle and a curved needle according to an embodiment.

The epidural space may be accessed with a straight or curved needle or cannula by the interlaminar, transforaminal, or sacral route. FIG. 9 schematically depicts a straight needle 90 and a curved needle 95 according to an embodiment. Metallic needles may be used. The needles can be hollow to enable introduction of flexible tubular bodies.

Figure 10:
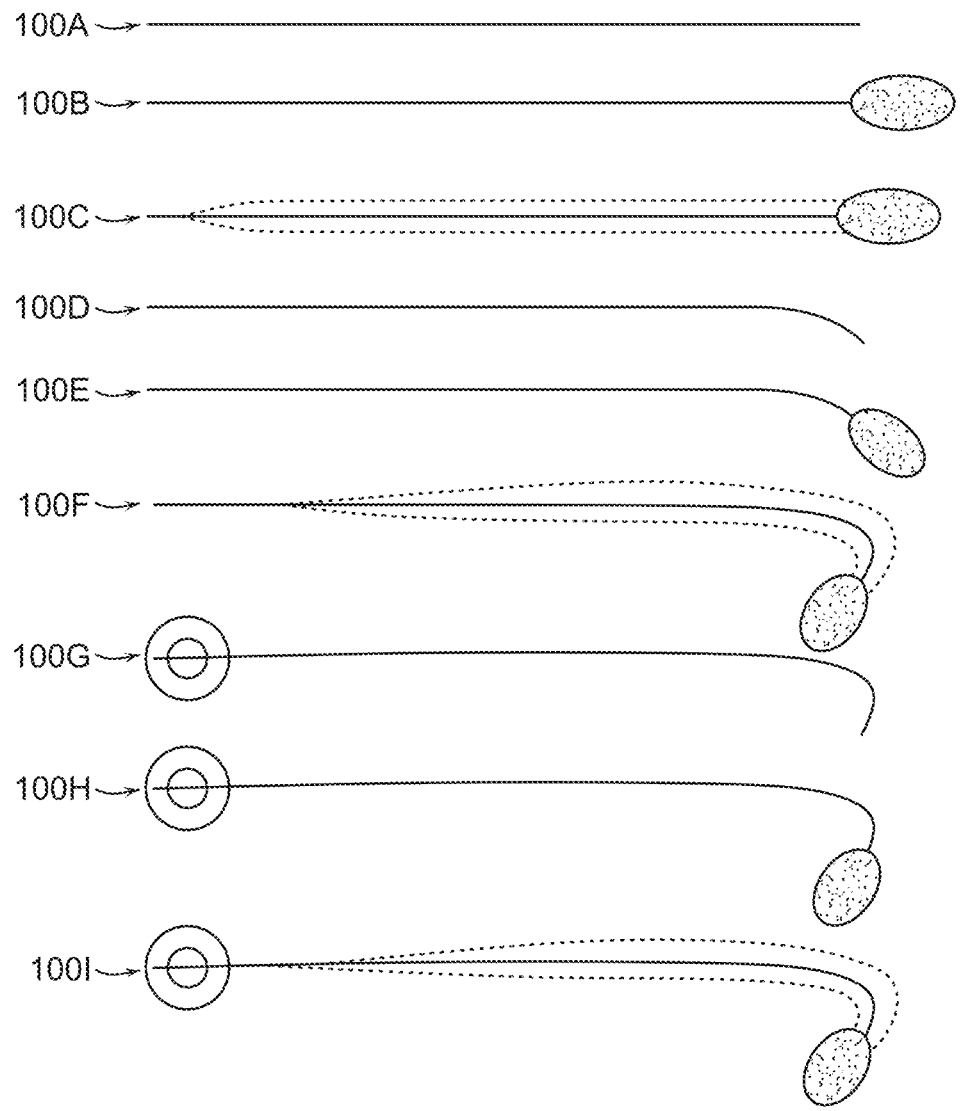
FIG. 10 schematically depicts a wire according to multiple embodiments.

A wire may then be threaded through the needle tip. FIG. 10 schematically depicts a wire according to multiple embodiments. Wires 100A-C represent straight wire. Wires 100D-F represent curved wires pre-bent or with a hollow core in which a curved stylet may be placed and appropriately curved. Wires 100G-I represent wires in which the curvature may be increased or decreased using a plurality of joints.

Wires 100A, 100D, 100G have no dilation tools. Wires 100B, 100E, and 100H have a dilation tool at the tip such as an inflatable balloon tip or a balloon may be advanced through the wire core and inflated at the tip. The tip may be wrapped in an inflatable membrane that can be inflated from outside. For wires 100C, 100F, 100I the entire wire or portions of thereof may be inflatable aiding the dilation of the space for allowing an epiduroscope or access device to pass. The wire may be wrapped in an inflatable membrane that can be inflated from outside. The membrane may have compartments allowing for segmental inflation. The wire may be solid or with hollow core. The wire may have straight or curved tip. The curved wire can assist in controlling wire tip motion. The curve may be attained by using a curved stylet or a pre-bent wire. By using the curve the wire may be advanced into the intended area under X-Ray visualization or other methods of control such as ultrasound, or other neuro-navigation tools.

The wires range from 0.5-2 mm, may be hollow or solid, and are made from metal or plastic. Curved wires may have a pre-bent tip or a hollow core into which a curved stylet may then be introduced. The wire may also have an adjustable curve, via a plurality of joints to allow for precise navigation in the epidural space. The epidural wires may also have an inflatable balloon tip to allow for creation of space when there is difficulty in navigation and to avoid puncturing the dura. The tip itself may be covered by an inflatable membrane or a balloon that can be introduced through the hollow core for this purpose. The entire wire or parts of the wire may be covered by an inflatable membrane to allow for dilation of the epidural space and for easy passage of the epiduroscope or the access device.

Figure 11:
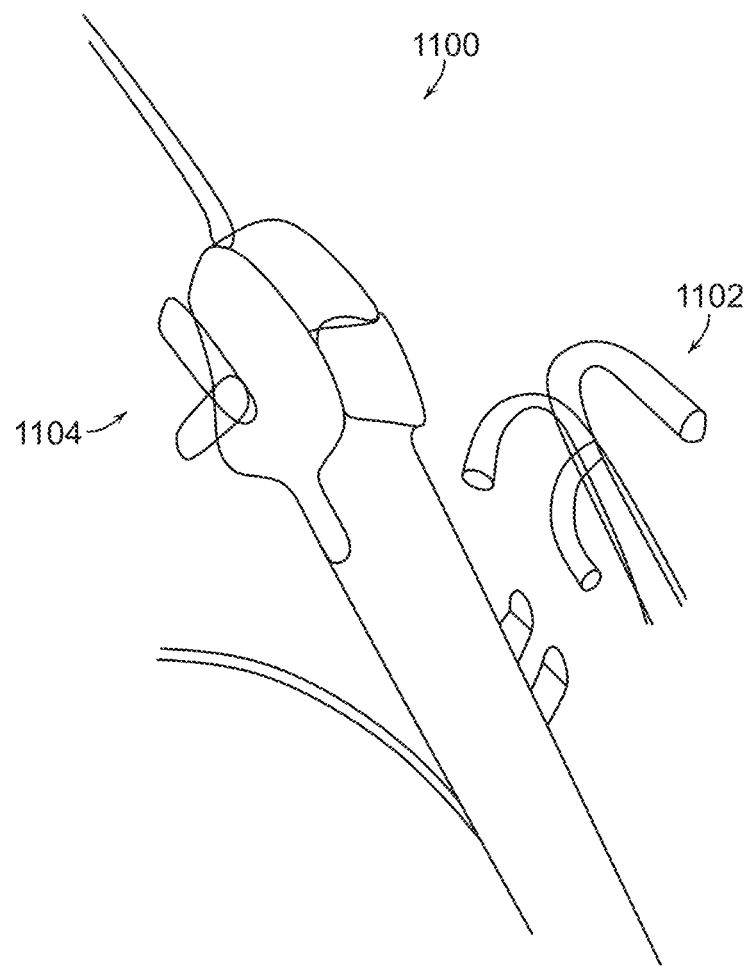
FIG. 11 schematically depicts a tip of an epiduroscope according to an embodiment.

FIG. 11 schematically depicts a tip of a working channel device or epiduroscope 1100 according to preferred embodiments. Note that the access device can comprise an epiduroscope or a combination with other components as described herein. In some embodiments, the wire tip curvature 1102 may be variable and controlled by the operator for greater precision. The curvature may be modulated by employing a plurality of joints. In some embodiments, the device tip can have a balloon to distend the area if unable to navigate. In some embodiments, device tip can have a stylet to form smooth passage for the device. A balloon or membrane can be inflated to distend the passage to enable visualization. The tip 1104 of the working channel device may be rotated or bent in different planes using wires that lie in the body of scope and are attached to the tip. The membrane can also serve to deflect tissue away from the surgical region and thereby prevent damage during therapy.

The sub 5 mm device with a stowed expandable tip may then be advanced over the wire. In another embodiment, the device tip can be non-expandable. The tip of the device may be moved in 1 or 2 or multiple planes employing a plurality of joints. The tip of the device has metallic strips interspersed with transparent plastic.

FIG. 12A schematically depicts unstowing and stowing of the tip of the device according to an embodiment. The tip of the device is covered circumferentially by a sleeve at the tip only or a circumferential outer tube throughout the length of the scope. When in the appropriate area, the sleeve or the outer tube is withdrawn to allow deploying of the tip. After exposure, the tip of the device can be unstowed by using a plurality of joints. The tip may be again stowed by advancing the outer tube or sleeve back over it.

The tip is covered by a sleeve 1201 that may extend the entire length of the device or just at the tip 1200A. The inner tube tip is in a stowed position. The outer sleeve is withdrawn using a trigger or other actuation mechanism in the handle of the scope 1200B. The tip may then be unstowed or dispensed for use. In this particular instance the tip is unstowed by tugging on the wires 1202 attached to the tip 1200C. Note that only the dural half of the tip can be moveable. This is accomplished by pulling a lever in the handle. The tip may be unfurled into a spherical configuration 1200S or more of a rectangular configuration 1200R as seen in FIG. 12B. The tip can be beveled (or not beveled) and the longer edge is optionally color coded red, for example. The device tip can be non-beveled and the dural edge, that is, the tip portion that engages and moves the durameter can be identified with a radio-opaque marker. The forward facing laser beam is centered at a point that can be (or not be) offset towards the receding edge. Other portions of the tip can also be radio-opaque to provide for appropriate recognition under fluoroscopy. The outer tube or sleeve maybe advanced back over the tip to stow it and the scope navigated into another area as needed. In preferred embodiments, only a portion of the distal circumference serves to displace the membrane to form a three dimensional visualization and ablation space. The various embodiments herein can incorporate this feature. Note that the base of the access device or epiduroscope can be enclosed or covered with an inflatable membrane to enable controlled movement in the anterior posterior plane.

Figure 13B:
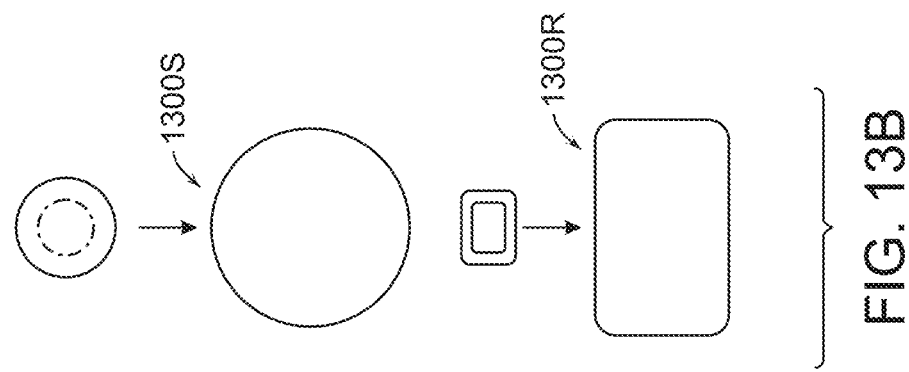
FIGS. 13A-13B schematically depict unstowing and stowing of the tip of the epiduroscope when the tip is made of nitinol in an expanded shape according to an embodiment.
Figure 13A:
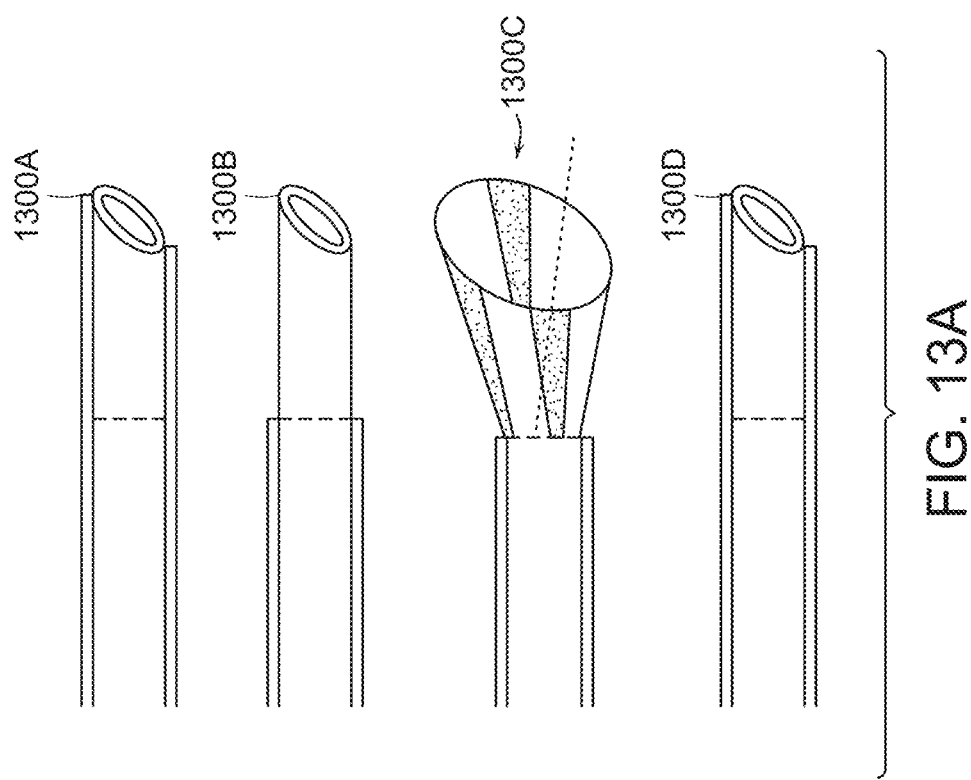

FIG. 13A schematically depicts unstowing and stowing of the tip 1300A-1300D analogous to 1200A-1200D of the epiduroscope when the tip 1300C is made of nitinol in an expanded shape according to an embodiment. In this embodiment, the tip is made of metal strips such as nitinol in an expanded shape. This is kept stowed by the outer tube which can be moved back and forth to enable rapid stowing and unstowing. As the outer tube is withdrawn, the inner stowed tip unfurls or moves into the preformed shape. As depicted in FIG. 13B in circular 1300S rectangular 1300R or other shape described herein. The outer sleeve or tube slides back on and the tip is again stowed allowing for further endoscope motion.

Figure 14B:
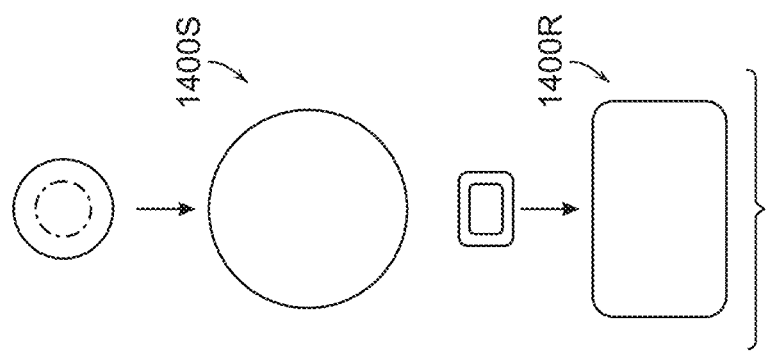
FIGS. 14A and 14B schematically depicts unstowing and stowing of the tip of the epiduroscope when the tip is unstowed with a balloon according to an embodiment.
Figure 14A:
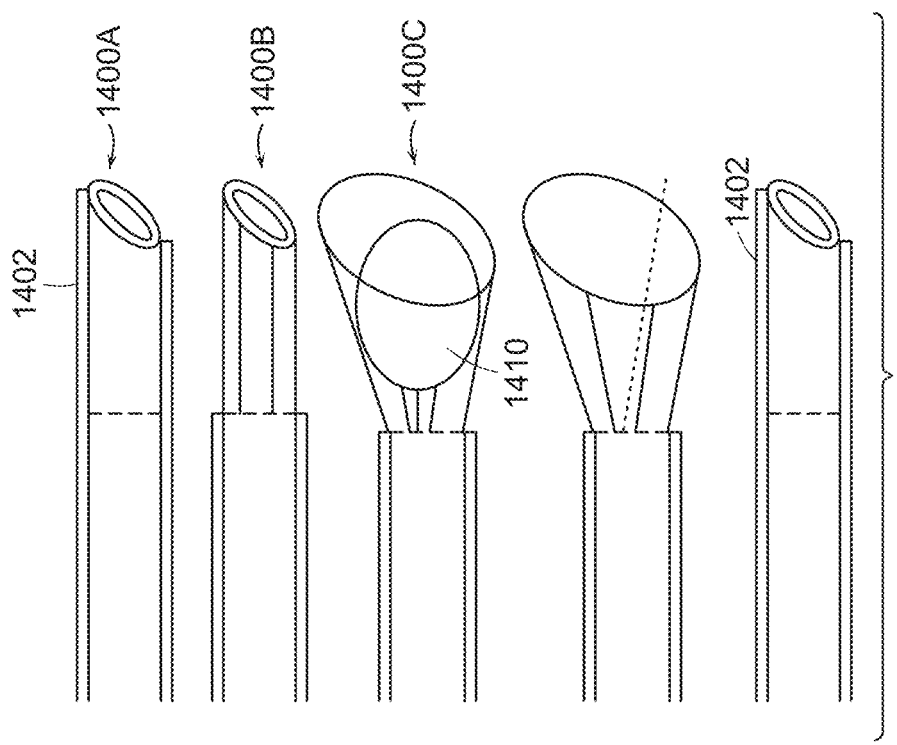

FIG. 14A schematically depicts unstowing and stowing of the tip of the device when the tip is unstowed with a balloon according to an embodiment. After exposure, the tip 1400C of the epiduroscope may be unstowed by deploying a balloon 1410 that is inserted through the working channel. The tip may be again stowed by advancing the outer tube or sleeve back over it. The metal strips or wires in the tip prevent spontaneous collapse. The sleeve or outer tube 1402 may be moved backwards and forwards using a lever at the proximal end and thus accomplishing opening and closing of the unstowed tip. Once the tip is stowed the scope can be mobilized in the epidural space again. The shape of the deployed structure is illustrated in FIG. 14B.

Figure 15:
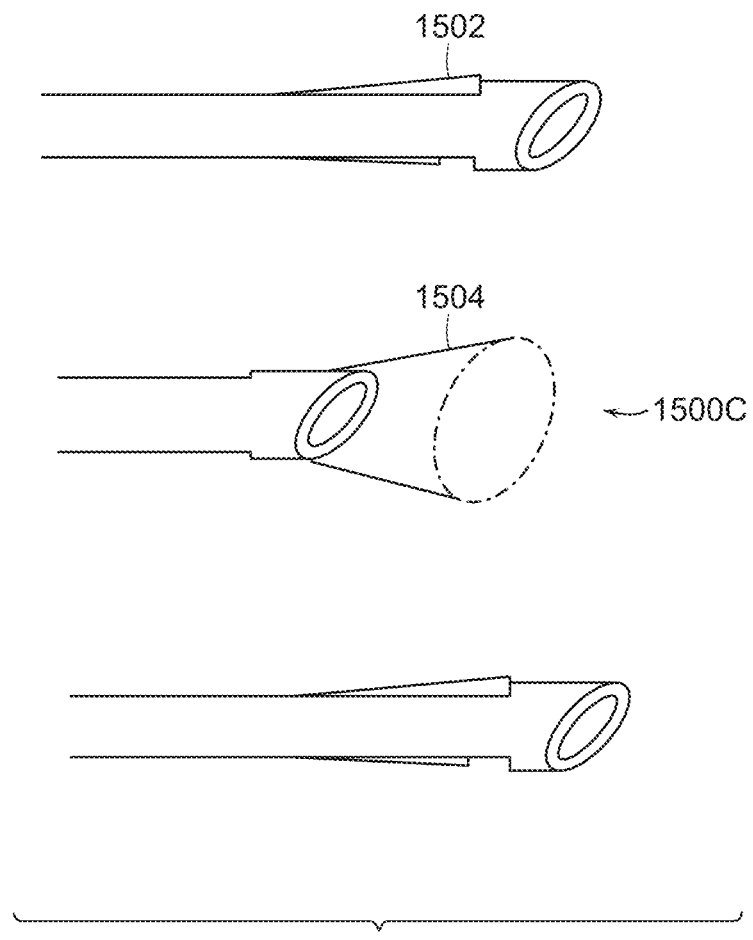
FIG. 15 schematically depicts unstowing and stowing of the tip of the epiduroscope when a stowable sheath is behind and external to the tip according to an embodiment.

FIG. 15 schematically depicts unstowing and stowing of the tip 1500C of the device when a stowable sheath 1502 is behind and external to the tip according to an embodiment. The stowable sheath 1502 is behind and external to the distal end of the scope. As the tip 1500C is retracted this deploys the sheath. As the tip is advanced the sheath is stowed. The distal edge of the outer tube overlies the proximal edge of the inner tube. As the inner tube is withdrawn it flays metal strips 1504 on the outer tube creating a funnel or rectangular shaped shield that displaces the dura mater allowing greater visualization through the inner tube. The inner tube is pushed distally collapsing the shield. The tip maintains shape from natural plasticity of inserted metallic strips.

The scope has a proximal and distal end. The proximal end can have a lever allowing motion of the tip through inbuilt control wires that extend along the length of the tubular scope. The handle has an intake for the light source, video output from the CMOS or CCD sensor, or fiber optic channel, a port for a laser, and two working channels. The laser channel is adaptable to all lasers suitable for the ablation procedure (e.g., Nd:YAG or Ho:YAG) but a preferred embodiment utilizes $CO_2$ laser delivery. Such lasers can operate at a wavelength of 10,600 nm and have output powers in a range of 40-100 watts that can be operated in a pulsed mode using pulse width modulation. The scope may be of variable length based upon the particular application such as whether to be used in the back or the neck. In some embodiments, the scope has a width of approximately in a range of 3-7 mm, and preferably at about 5 mm or less.

The tubular body can possess varying degrees of flexibility. The body can be a double tube or a single tube with a coaxial external tip at the distal end. The outer tube the distal tip can be retractable to deploy and stow the expandable tip. The handle has levers for mobility of the distal tip in one or more planes.

A balloon can be advanced through the working channel and inflated at the tip to allow for smooth distal tip to allow navigation and decrease risk of dural puncture. In embodiments where the expandable tip is activated by wires there is a lever for stowing and retracting the tip as well as a lever for sliding the sleeve or the outer tube. In embodiments where the expandable tip is composed of a material with metal memory such as nitinol, there is a lever in the handle for actuating the outer sleeve or tube of the scope that leads to opening and closing on the tip. In embodiments where the expandable tip is actuating by a balloon, the balloon can slide through the working channel and expand the tip. A lever retracts the outer tube. The outer tube can slide back over the expanded tip to be stowed. In embodiments the outer tube or the distal tip can have a hinged end such that pulling the inner tube deploys the outer tube or outer distal tip to allow visualization in this manner.

The stowable tip is slightly oblong with the longer side color coded and directed to the dura mater. At the distal end of the tip is the laser beam aperture, two working channels and a camera sensor. The forward facing laser can be directed slightly off center towards the closer portion of the target material.

In an embodiment, only the access channel device is initially introduced. It has the stowable tip that can be deployed using any of the methods described above. Once it is deployed the device with a laser emission port, one or two working channels, and a camera can then be introduced to reach the distal end of the stowable tip of the working channel.

In an embodiment, the epiduroscope or access device can be semi-rigid or rigid with a flexible tip. In some embodiments, the access device or the cannula and stowable tip can be tubular structure or have of a substantially rectangular or ellipsoid cross section or profile.

In an embodiment a wire with an inflatable hood may be advanced through the working channel and advanced over the intruding pathology providing a safety wall to the spinal sac distally. In an embodiment, a color shield or balloon may be introduced from the opposite side to provide a barrier and an end point to the firing laser.

The distance of the laser tip from the pathology is radiologically and visually ascertained. A measuring tool such as a rigid wire or rod can be advanced from the distal tip to contact the pathology or tissue/material to be removed. This can include a sensor that indicates the distance to the target region, computes and indicates the spot size and communicates the power requirements and can automatically set the illumination parameters. The laser can be operated in a continuous mode, a pulsed mode, or super pulsed mode. When the disc is at an optimal distance from the pathology and the safe side of the cannula is placed toward the bone the $CO_2$ laser is fired. The laser emission is adjusted based upon radiological measures so that damage is restricted to the target and not beyond. The laser is fired under continuous visual monitoring. The tip is stowed and the cannula moved slowly as and when needed. Saline flush or other fluid or gas flow can optionally be used for removal of the vaporized tissue. The ablation process continues until all the area of pathology is ablated visually as well as determining the status radiologically by x-ray, ultrasound, or computed tomography (CT) imaging procedures. A wire can also be extended to form the distal tip for distance measurement.

Figure 16A:
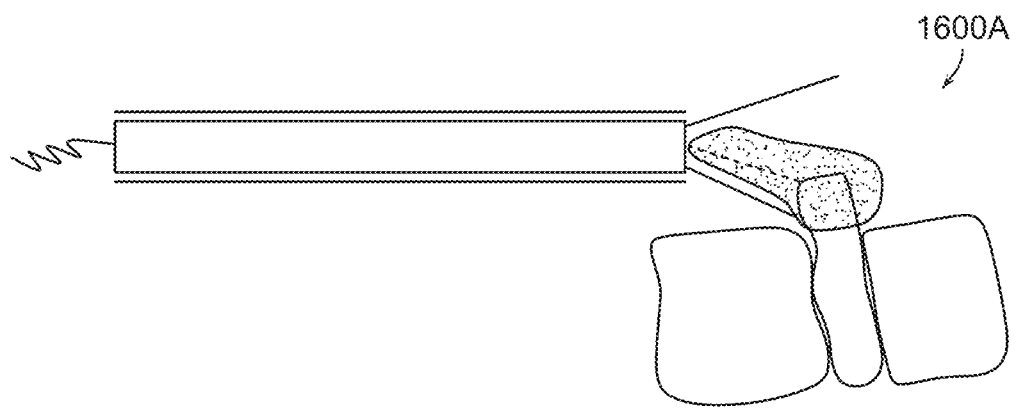
FIG. 16A schematically depicts a balloon distally advanced over a herniated disc according to an embodiment.
Figure 16B:
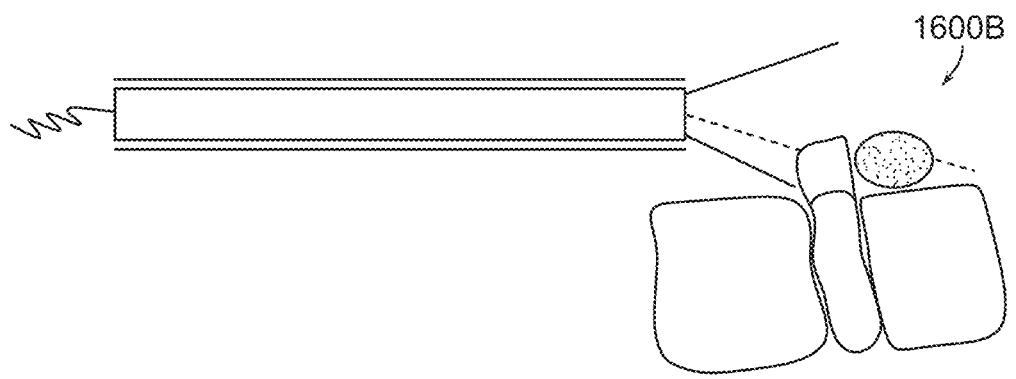
FIG. 16B schematically depicts a balloon proximally advanced over a herniated disc according to an embodiment.

FIG. 16A schematically depicts a balloon 1600A distally advanced over a herniated disc according to an embodiment. This provides a distal shield as well as indicator for procedure completion. FIG. 16B schematically depicts a balloon 1600B proximally advanced over a herniated disc according to an embodiment.

Figure 17A:
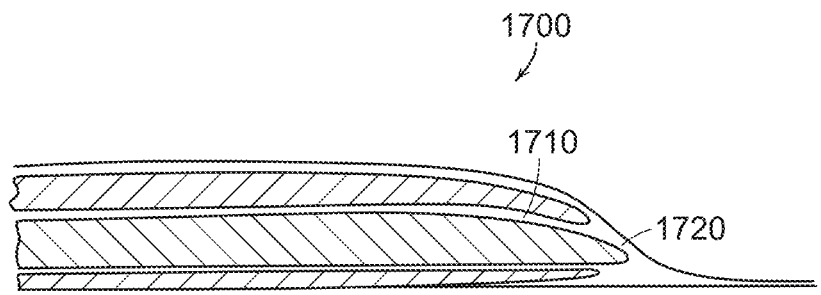
FIG. 17A schematically depicts an epiduroscope moving between a membrane and a spinal bone according to an embodiment.

FIG. 17A schematically depicts a stylet for introducing an epiduroscope 1700 moving in an epidural space between a membrane and a spine according to an embodiment. The epiduroscope comprises a working channel 1710. Within the working channel 1710 is a stylet 1720. The working channel 1710 is shaped to smoothly move under membranous tissue without tearing the membrane. Additionally, the shape of the working channel 1710 allows for extension and withdrawal of the stylet 1720 without inhibiting the movement of the stylet 1720. The distal tip of the stylet 1720 is marked, dyed, coated, or otherwise manufactured to be visible via x-ray, fluoroscopy, or other diagnostic tool. In some embodiments, the distal tip may be fluorescent. The distal tip of the stylet 1720 is a domed, blunt nose that deflects the membrane around the sides of the tubular body of the stylet 1720. Note that the distal tip of the stylet can include an inflatable device or membrane to gently form a cavity in case of an obstruction, scar tissue, or adhesions.

Figure 17B:
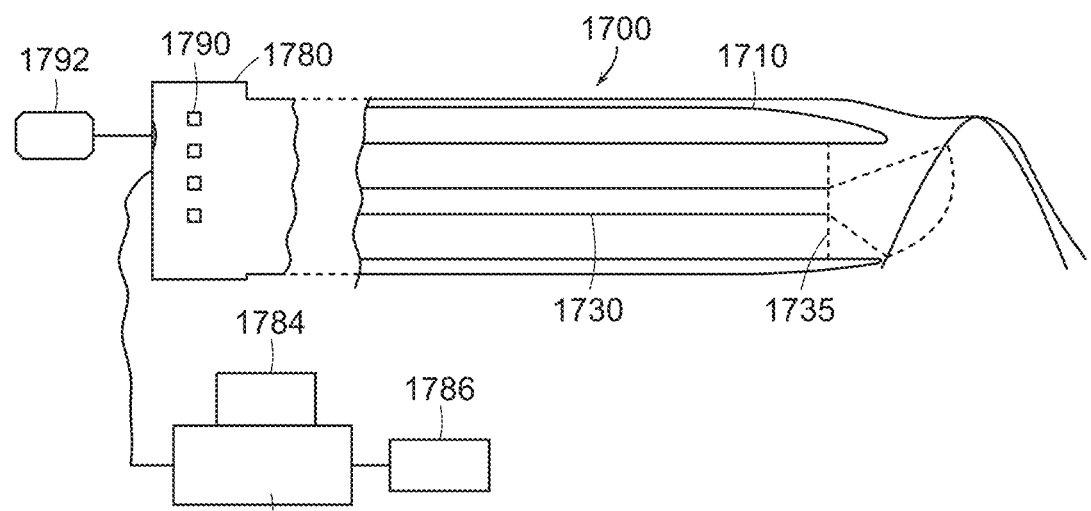
FIG. 17B schematically depicts an epiduroscope approaching an intruding pathology according to an embodiment.

FIG. 17B schematically depicts an epiduroscope 1700 approaching an intruding pathology according to an embodiment. Upon reaching the pathology, the stylet 1720 can be withdrawn. In some embodiments, the stylet 1720 is withdrawn by twisting the stylet 1720 and pulling the stylet 1720 away from the pathology. A laser 1730 is then positioned at a predetermined position 1735 within the working channel 1710. Specifically, the laser 1730 is positioned in a position 1735 at a distance from the pathology wherein the laser 1730 is able to ablate the pathology.

Figure 17C:
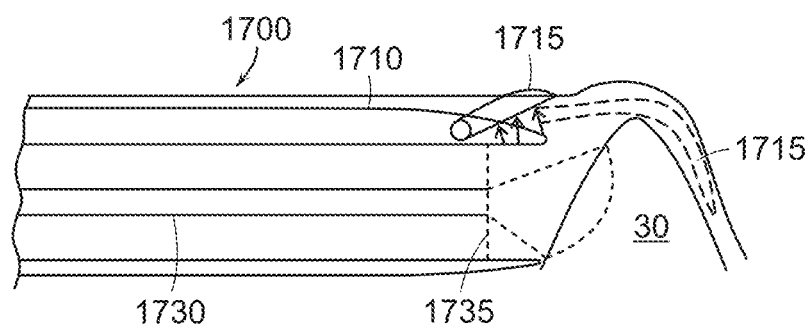
FIG. 17C schematically depicts an epiduroscope with a hinged member according to an embodiment.

FIG. 17C schematically depicts an epiduroscope 1700 with a moving member attached to a distal end such as a hinged member 1715 according to an embodiment. As the stylet 1720 is withdrawn, a hinged member 1715 on the distal end of the working channel 1710 moves forward to maintain an opening to view and treat the surgical site. The hinged member 1715 maintains an opening for the laser 1730 to ablate the intruding pathology. The member 1715 can also extend to the opposite side of the material 30 such that the light that is used to ablate tissue 30 does not fully penetrate and thereby damage the epidural membrane. Alternatively, a second probe can be percutaneously inserted from a different location on the opposite side of tissue 30 that is positioned to absorb or reflect light from the laser that would otherwise be directed onto the inner surface of the membrane or other adjacent tissue. Note that the devices described herein can include handle enabling manual manipulation and actuation of electronic components. The handle 1780 can be connected to computer 1782, image display 1784, and data storage 1786 devices. The handle 1780 can have manual actuators 1790 to trigger the laser that is located in the handle or in an external laser light source such as $CO_2$ laser 1792 which can be coupled into the handle by rigid waveguides, flexible hollow fiber as described herein or free space lens assembly, imaging devices, LED illumination, target illumination, and distance measuring element. The handle can include imaging sensors coupled to fiber optics, light sources for illumination, and a control processor connectable to an external computer and network.

Figure 17D:
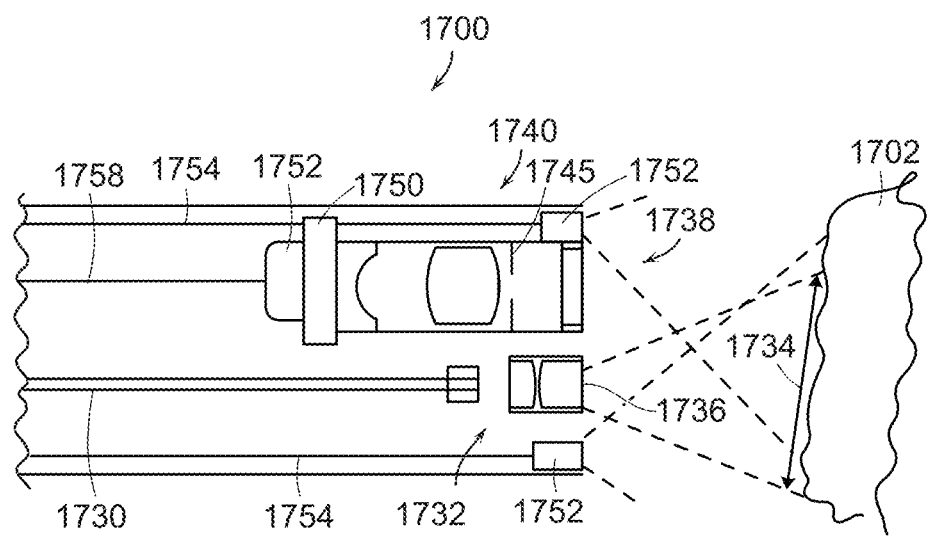
FIG. 17D schematically depicts a laser, lenses, and a digital imager of an epiduroscope according to an embodiment.
Figure 17E:
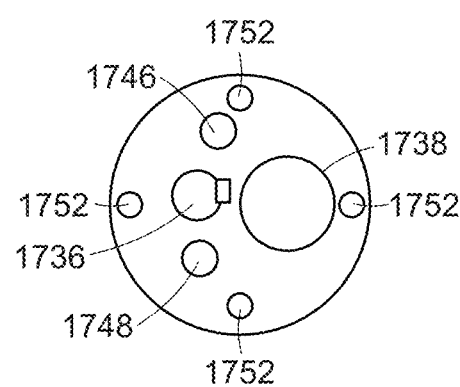
FIG. 17E schematically illustrates a cross sectional view of the device depicted in FIG. 17D.

FIGS. 17D-17G depict embodiments that can be inserted into the working channel of FIG. 17A or can be used as integral units having the dilating elements described generally herein. FIG. 17D schematically depicts a distal end of a preferred epiduroscope including an optical fiber or bundle of optical fibers 1730 to deliver light onto an area 1734 of tissue 1702 to be removed. The lenses 1740, aperture stop 1745 and a digital imager 1750 of the epiduroscope 1700 enable visualization of the tissue 1702. After withdrawing the stylet 1720, for example, the tissue visualization and ablation device is inserted through the working channel 1710. The surgeon first illuminates the tissue to visually identify the area to be ablated and positions the device to direct a beam of light onto a spot 1734 of a tissue surface. The lenses 1740 receive light from the field of view, including the tissue 1702 to be removed. The resulting image is detected by the digital imager 1750. In some embodiments, the digital imager 1750 is a CMOS sensor. In some embodiments, the digital imager 1750 is a charge-coupled device (CCD). The digital imager 1750 preferably has at least 50,000 pixels and preferably 300,000 pixels for high resolution imaging at video frame rates. For embodiments employing a lower resolution camera, the number of pixels in the digital imager 1750 can be at least 30,000 or at least 10,000. A small diameter imaging device such as that described in U.S. application Ser. No. 15/051,265 filed on Feb. 23, 2016 can be used, the entire contents of the above application being incorporated herein by reference. The digital imager 1750 transmits a digital image data to a computer for processing and display. The imaging device can include a processor 1752 that processes the image data and transmits the data through conductive connector or wire to the proximal end of the endoscope. As seen in FIG. 17E, the distal ends of the fibers or the LEDs 1752 can be arranged in an annular array within the tubular body 1747 to more evenly illuminate the field of view. The imaging aperture 1738 and the light emission aperture 1736 for the removal of tissue are preferably aligned upon a central axis of the tubular body 1700. The field of view can be illuminated by one or more light emitters 1752 which can be optical fibers, optical fiber bundles or light emitting diodes (LEDs) mounted at the distal end of the endoscope. The visualization and ablation device can optionally include a suction channel 1746, a fluid delivery channel 1748, an instrument channel, or a balloon sheath.

Figure 17F:
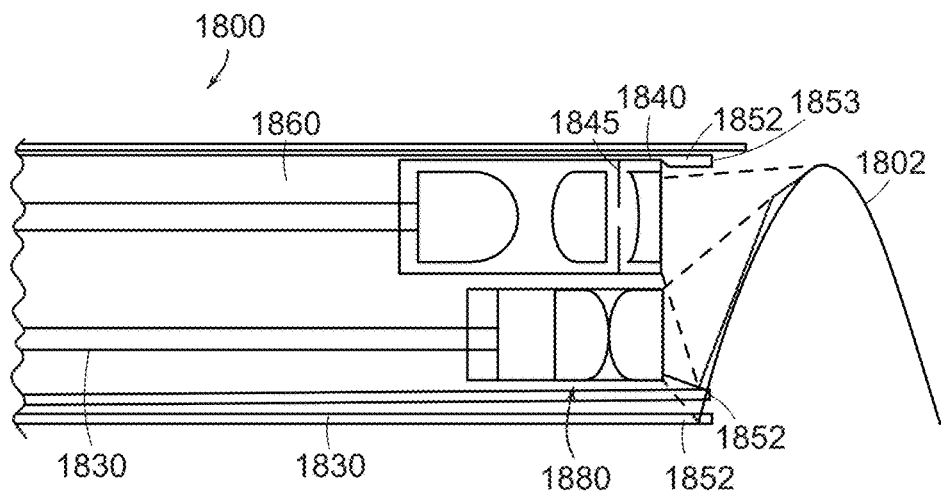
FIG. 17F schematically depicts a laser, lenses, and a fiber optic imaging channel of an epiduroscope according to an embodiment.

FIG. 17F schematically depicts an optical fiber 1830 to deliver light for ablation of tissue in which, lenses 1880, evenly distribute the light onto tissue 1802. A fiber optic imaging channel 1860 of an epiduroscope according to this embodiment couples the image to an image sensor at the proximal end. The lenses 1840 can be optically coupled to a distal end of a fiber optic imaging channel that can extend through the working channel 1710 to enable viewing of the region of interest. The fiber optic imaging channel 1860 preferably has at least 300,000 pixels, and preferably more than 1 million pixels for high resolution imaging at video frame rates. The fiber optic imaging channel 1860 transmits the image that is delivered to a detector which generates digital image data to a computer for processing and display.

As shown in FIGS. 17D and 17F, the digital imager 1750 or the fiber optic imaging channel 1860 can be mounted within a second tubular body in which a laser light delivery system can also be mounted such that the digital imager 1750 or the fiber optic imaging channel 1860 and related optical elements are arranged to view the illuminated region of tissue. A second white light source such as a light emitting device (LED) can be used to provide illumination of the small surgical field of view.

Preferred embodiments of the invention relate to the use of light sources emitting at wavelengths that will ablate or vaporize tissue to be removed from a surgical site for treatment of spinal injury or conditions that impair movement and/or cause pain. A $CO_2$ laser can be used to emit a beam of light that is coupled into a waveguide of an endoscope or epiduroscope for delivery to a location within the epidural space.

Figure 17G:
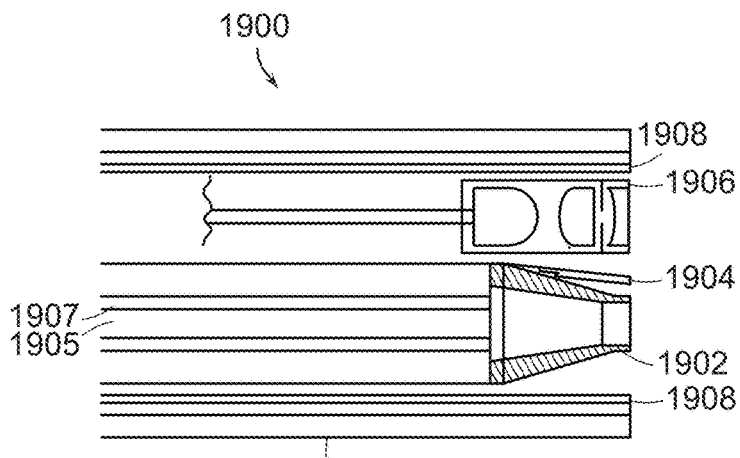
FIGS. 17G and 17H illustrate preferred embodiments of a tissue ablation device in accordance with preferred embodiments of the invention.
Figure 17H:
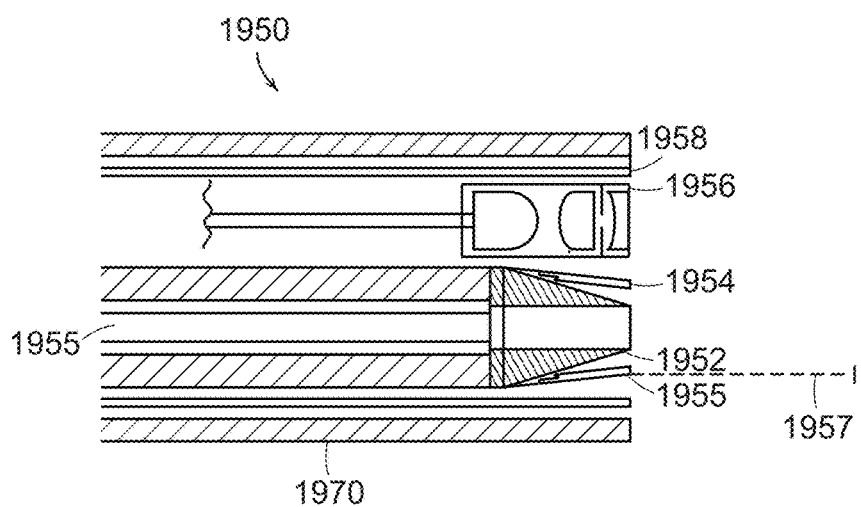

In FIG. 17G, a probe body 1920 has been inserted into the epidural space. The body 1920 can be a flexible tubular member that is inserted into the epidural space using procedure described in the present application. Light from a $CO_2$ laser is coupled into waveguide 1907 to couple light into distal beam shaping element 1902 waveguide 1907 can be flexible and use silica and silver layers such as those available from Laser Engineering Inc. in Milford, MA An optical fiber 1904 can be used to illuminate the spot that is to be ablated by the light emitted from element 1902. Note that a hard ceramic can be used at the distal tip of the waveguide. Fluid aspiration can be used to clean the tip during the procedure. The spot generated by optical fiber 1904 is pre-aligned with the spot illuminated by element 1902 so that a user can see the tissue region to be ablated by one or more laser pulses emitted from the distal aperture of element 1902. Visualization channel 1906 is positioned for viewing tissue to be ablated at a distance from the distal end of the device. Annular light emitting elements 1908 are used to illuminate the entire field of view to enable steering of the targeting light spot provided by fiber 1904. Alternatively, a beam of visible light can also be coupled into channel 1905 of waveguide 1907 using a mirror and a further LED light source. FIG. 17H shows a second beam shaping element 1952 that projects a spot having a different size onto the defect to be treated. The emission aperture can be open and can use a fluid such as a gas flow to maintain the waveguide free of body fluids or debris. Alternatively the emission aperture can be covered or enclosed with a light transmissive cap or window at the wavelengths of the $CO_2$ laser. A probe element 1955 can be extended distally to contact material to be ablated and thereby determine a distance 1957 from a distal end of the device in the present and previously described embodiments. This distance can be used to automatically compute ablation laser parameters based on spot size.

Figure 17I:
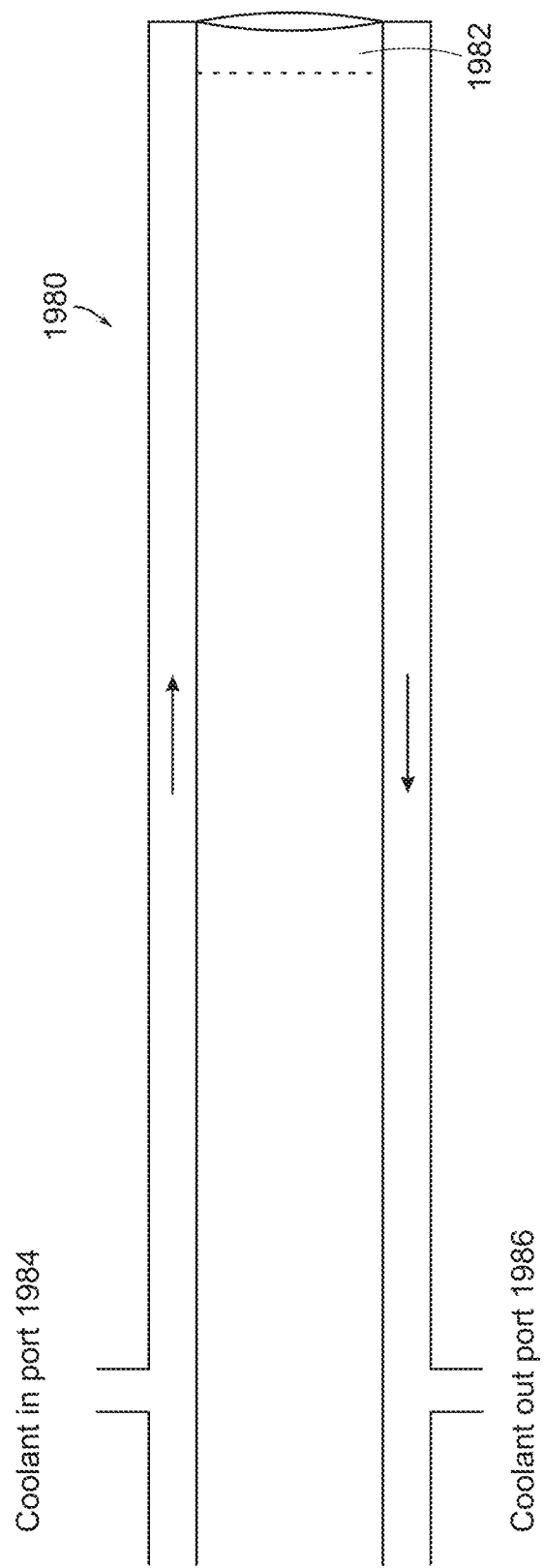
FIG. 17I illustrates an embodiment having a cooling fluid.

As shown in FIG. 17I a coolant can be introduced into the catheter or endoscope body 1980 where fluid is directed through port 1984 into one or more channels within the tubular body towards the distal end where in passes along a distal channel 1982 and reverses direction to exit port 1986. This embodiment can be used for application using continuous wave or longer pulse duration applications to ablate material for certain applications.

Figure 17J:
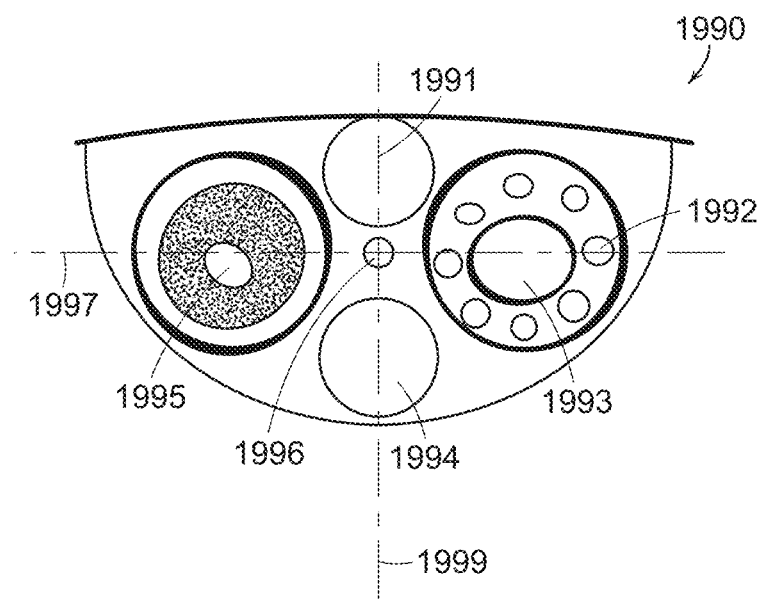
FIGS. 17J and 17K illustrate an embodiment having a distal surface that is displaced in one direction along a device axis 1991 that is orthogonal to device axis 1997.
Figure 17K:
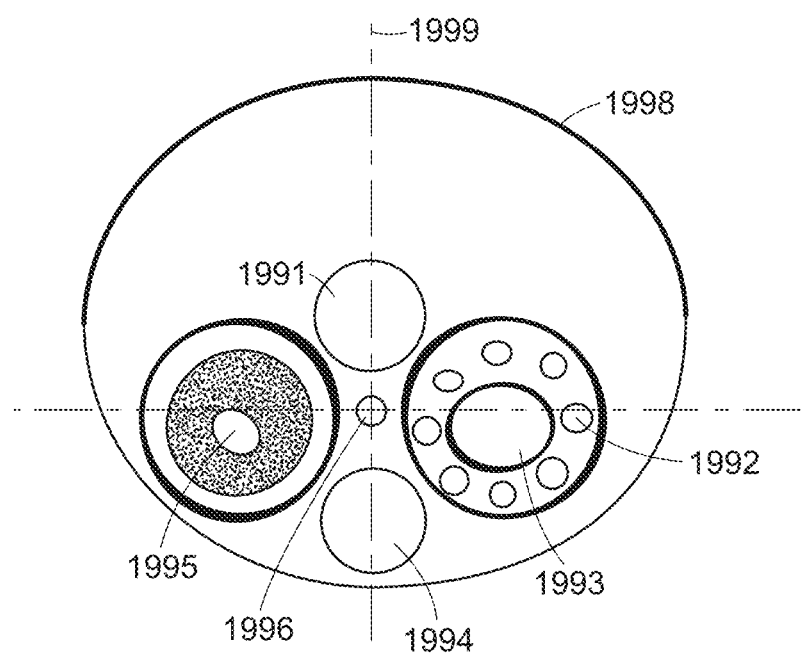

FIGS. 17J and 17K illustrate cross-sectional views of an embodiment having a first curved side 1990 that expands to a larger diameter 1998 to move the epidural membrane and thereby form the visualization and ablation of cavity.

Figure 18:
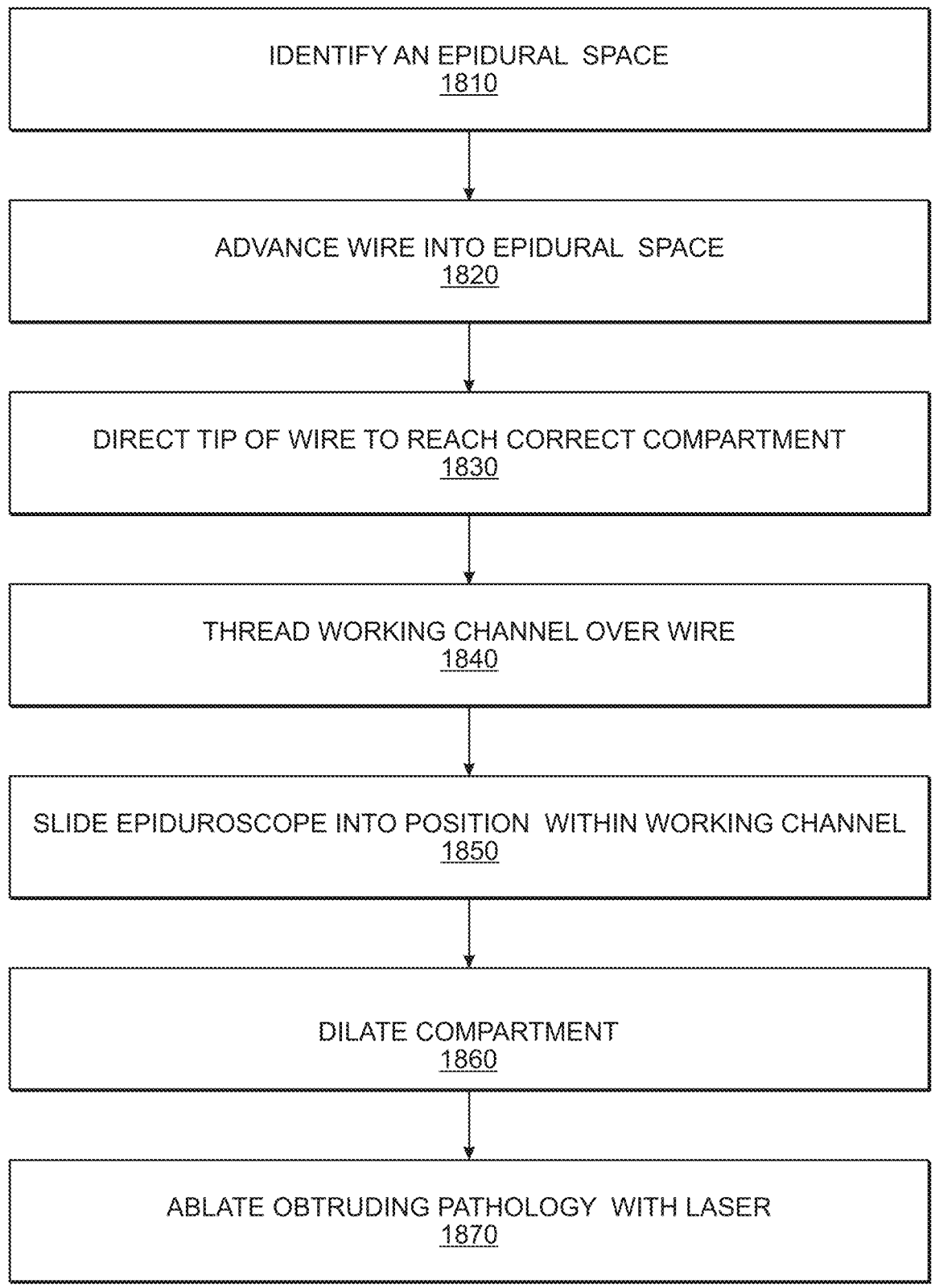
FIG. 18 depicts a method of removing an encroaching structure in an epidural space, according to an embodiment.

FIG. 18 depicts a method of removing an encroaching structure in an epidural space, according to an embodiment. The method begins when an epidural space is identified (Step 1810). The epidural space can be identified by loss of resistance technique. A wire is advanced into an epidural space (Step 1820). A curved wire is preferred to aid in navigation to the desired location. The wire may be semi-rigid (0.5-2 mm) and is slowly advanced by gentle direct force.

The tip of the wire is then directed to reach the correct compartment (Step 1830). A working channel is threaded over the wire (Step 1840). Once the working channel is threaded over the wire to the correct location an epiduroscope is slid into position within the working channel (Step 1850). If necessary, the compartment is dilated (Step 1860). Dilators of different sizes may also be used sequentially to thread over the wire to create space for the epiduroscope. The dilators are made of plastic or metal with variable rigidity and diameter. These may be threaded over the wire in a sequential fashion to create space for the epiduroscope when difficulty arises in threading the epiduroscope.

Then, intruding pathology is ablated with a laser (Step 1870). The laser may be a $CO_2$ laser. In an embodiment a wire with an inflatable hood may be advanced through the working channel and advanced over the intruding pathology providing a safety wall to the spinal sac distally. In an embodiment, a color shield or balloon may be introduced from the opposite side to provide a barrier and an end point to the firing laser. In other embodiments, alternative energy sources such as quantum molecular resonance, coblation, heat, or ultrasonic energy may also be used to ablate the tissue. In such cases, it may be desirable to advance the energy source under direct vision to contact the tissue to be ablated.

Figure 19A:
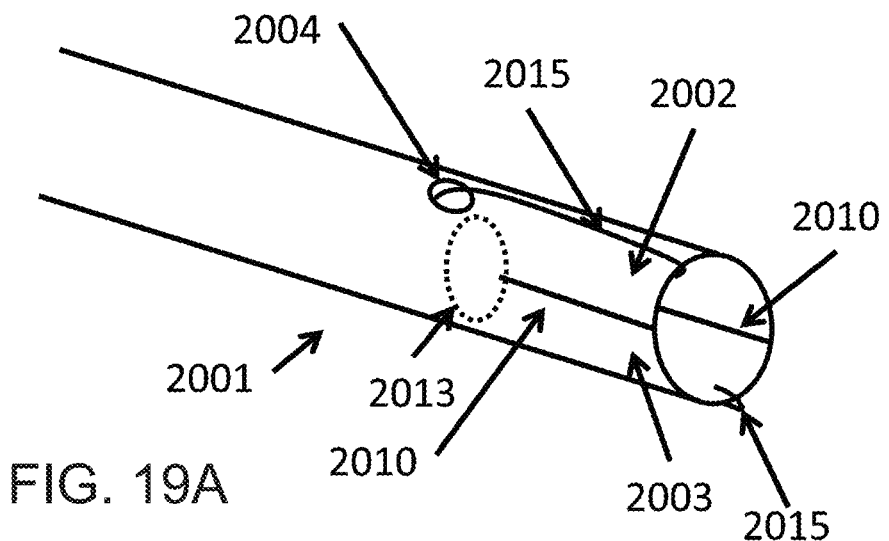
FIG. 19A illustrates a perspective view of a tubular body with one or more slits from the distal tip in accordance with various embodiments described herein.

FIG. 19A illustrates a perspective view of a tubular body 2001 with one or more slits 2010 from the distal tip in accordance with various embodiments described herein. In various embodiments, it is advantageous to enable the tubular body 2001 to expand distally to, for example, hold back issue and to create an open space to perform imaging and ablation of tissue. By providing a slit 2010, the distal tip of the tubular body is split into a first section 2002 and, optionally, a second section 2003 that can bend independently of one another and, more particularly, away from a longitudinal axis of the tubular body 2001 or one other. As will be described in greater detail below, an actuating mechanism may be used to cause the first section 2002 and the second section 2003 to move apart to dilate tissue or to create a larger clear working volume for the imaging and ablation systems that enter into the tubular body working channel. In one example, the actuating mechanism can be a wire 2015 that passes from an interior of the tubular body 2001 through an aperture 2004 to the exterior of the tubular body 2001. When the wire 2015 is pulled taut, the wire 2015 exerts a force on the first section 2002, for example, and causes the section to flex outwardly. Alternatively, the wire 2015 can be embedded in the wall of the tubular body 2001 throughout and attached to the distal tip of the tubular body 2001 such that when the wire 2015 is pulled taut, the first section 2002 and/or second section 2003 is flexed outward by virtue of force exerted at the base of the slit. In some embodiments, the wire 2015 may be a ribbon to minimize thickness.

Optionally, the slit 2010 of the tubular body 2001 can terminate distally at a through hole 2013 that passes through the wall of the tubular body 2001. One or more through holes 2013 can be formed in the tubular body 2001 to create a thin portion of the tubular body that acts as a hinging mechanism. In other words, bending of the tubular body 2001 during flexing of the first section 2002 or the second section 2003 will preferentially occur at the hinging mechanism (e.g., flexion point) formed by the removal or thinning of material at the through hole(s). In some embodiments, through holes 2013 are placed on opposite sides of the tubular body 2001. In some embodiments, the though hole 2013 can be formed by boring, coring, or drilling through the tubular body 2001.

Figure 19B:
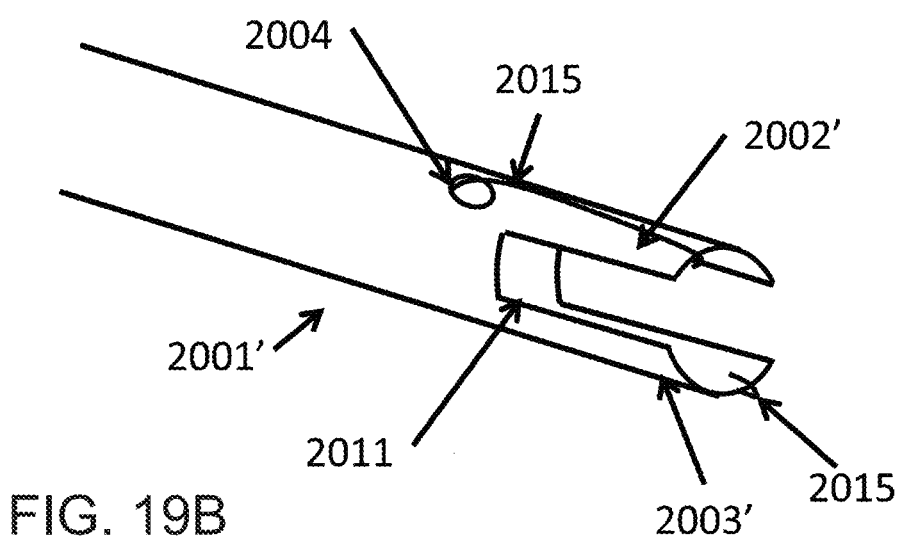
FIG. 19B illustrates a perspective view of a tubular body with an open end design at the distal tip in accordance with various embodiments described herein.

FIG. 19B illustrates a perspective view of a tubular body 2001' with an open end design at the distal tip in accordance with various embodiments described herein. In FIG. 19B, the tubular body 2001' includes a cutout 2011 that causes the distal tip of the tubular body 2001' to form a first section 2002' and a second section 2003' as protruding blades or paddles. Because the first section 2002' and the second section 2003' are unconnected to neighboring segments of the tubular body along the length of the cutout 2011, the first section 2002' and the second section 2003' are able to flex when actuated to dilate surrounding tissue.

In some embodiments with a slit 2010 or cutout 2011, the tubular body 2001, 2001' or a portion thereof can be formed of a plastic or shape memory material such as nitinol. In some embodiments, the first section 2002, 2002' and the second section 2003, 2003' can be color-coded (e.g., different colors are used for different sections to allow visual identification. The first section 2002, 2002' and the second section 2003, 2003' can be radiopaque in some embodiments. In some embodiments, a length of the first section 2002, 2002' can be longer than a length of the second section 2003, 2003' to allow the sections to be distinguished in, e.g., x-ray images and can also aid in selecting a direction for the illuminating beam or viewing angle.

Figure 20A:
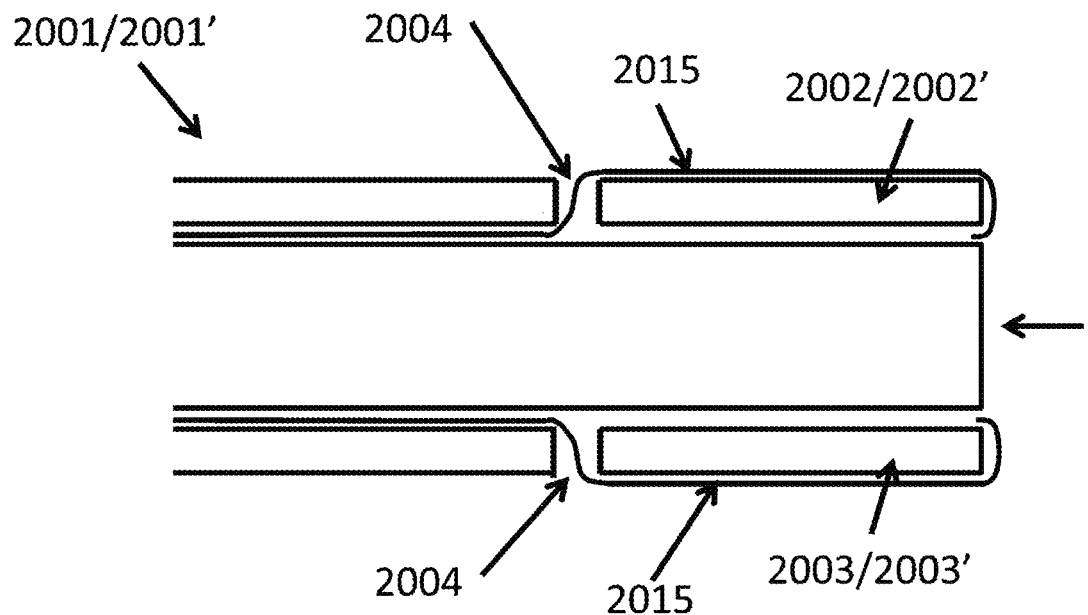
FIGS. 20A and 20B illustrate cross-sectional views of a tubular body with a wire actuator in the stowed and unstowed positions, respectively, in accordance with various embodiments described herein.
Figure 20B:
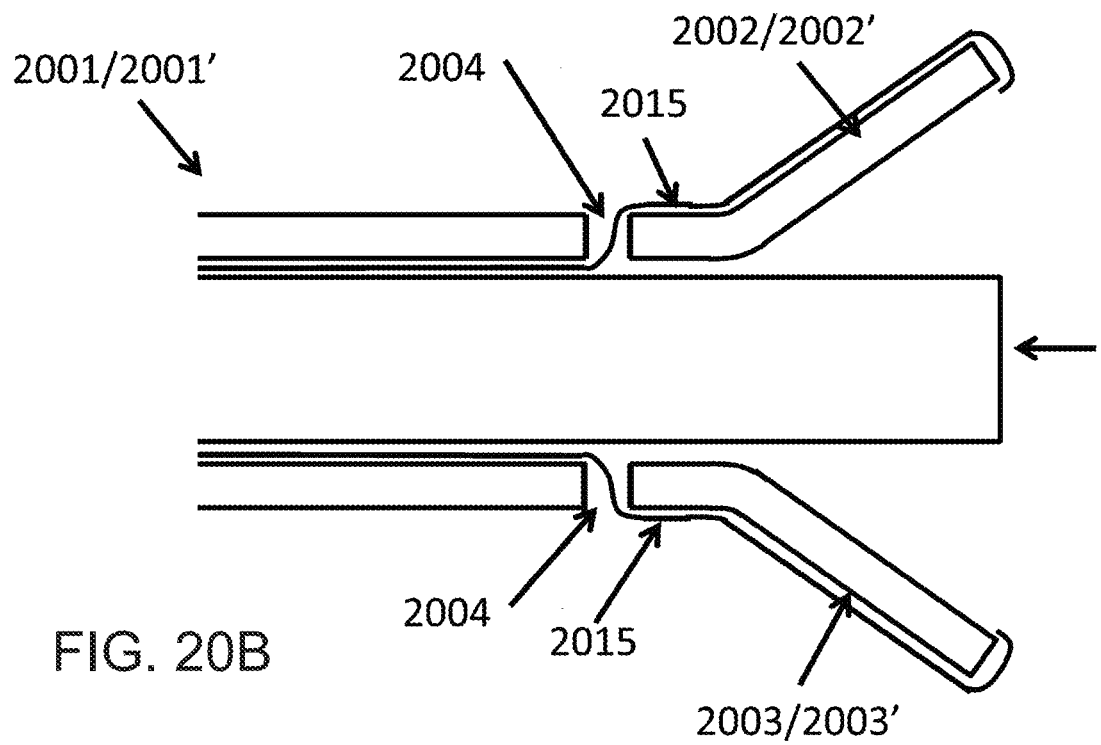

FIGS. 20A and 20B illustrate cross-sectional views of the tubular body 2001, 2001' with a wire 2015 actuator in the stowed and unstowed positions, respectively, in accordance with various embodiments described herein. The wire 2015 can pass from the interior of the tubular body 2001, 2001' through the aperture 2004 to the exterior of the tubular body 2001, 2001'. In some embodiments, the aperture 2004 can include a sealing mechanism such as an O-ring that produces a fluid-tight seal around the wire 2015. In some embodiments, the wire 2015 is embedded in the wall of the tubular body 2001, 2001' throughout to the tip and motion of the first section 2002, 2002' and/or second section 2003, 2003' occurs by pulling the wire taut causing the hinge point to give out and flexing the sections outward.

The wire 2015 can curve over the distal tip of the tubular body 2001, 2001' in some embodiments. In some embodiments, the stiffness of the wire 2015 can hold the wire in place over the lip of the distal tip. In some embodiments, the wire 2015 can be affixed to the interior of the tubular body using, for example, welding, soldering, embedding, or adhering. The wire 2015 can be affixed to a distal surface of the distal tip in some embodiments. The wire 2015 can be affixed to an exterior of the tubular body 2001, 2001' in some embodiments. If the wire 2015 is affixed sufficiently distally on the exterior of the scope, pulling the wire 2015 can still urge the first section 2002, 2002' and second section 2003, 2003' away from one another. Although the wire 2015 is depicted in FIGS. 20A and 20B as running external to the tubular body, 2001, 2001', the wire 2015 can be disposed in a channel along the exterior of the tubular body in some embodiments. In this way, the wire 2015 is less likely to irritate surrounding tissue as the tubular body is inserted.

Figure 21A:
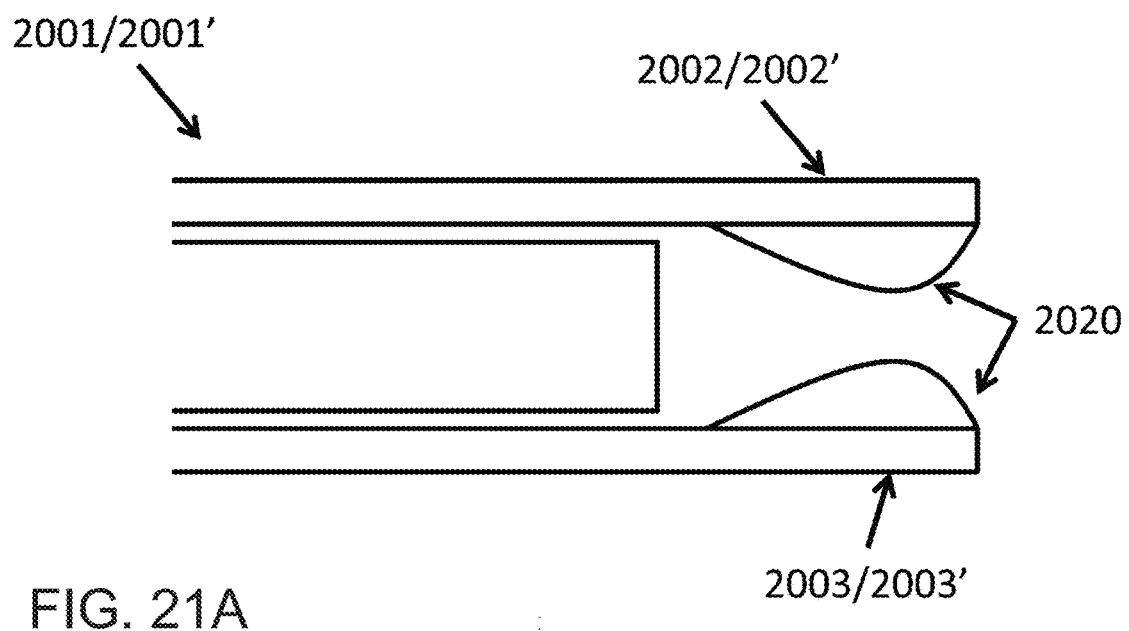
FIGS. 21A and 21B illustrate cross-sectional views of a tubular body with protrusions in the stowed and unstowed positions, respectively, in accordance with various embodiments described herein.
Figure 21B:
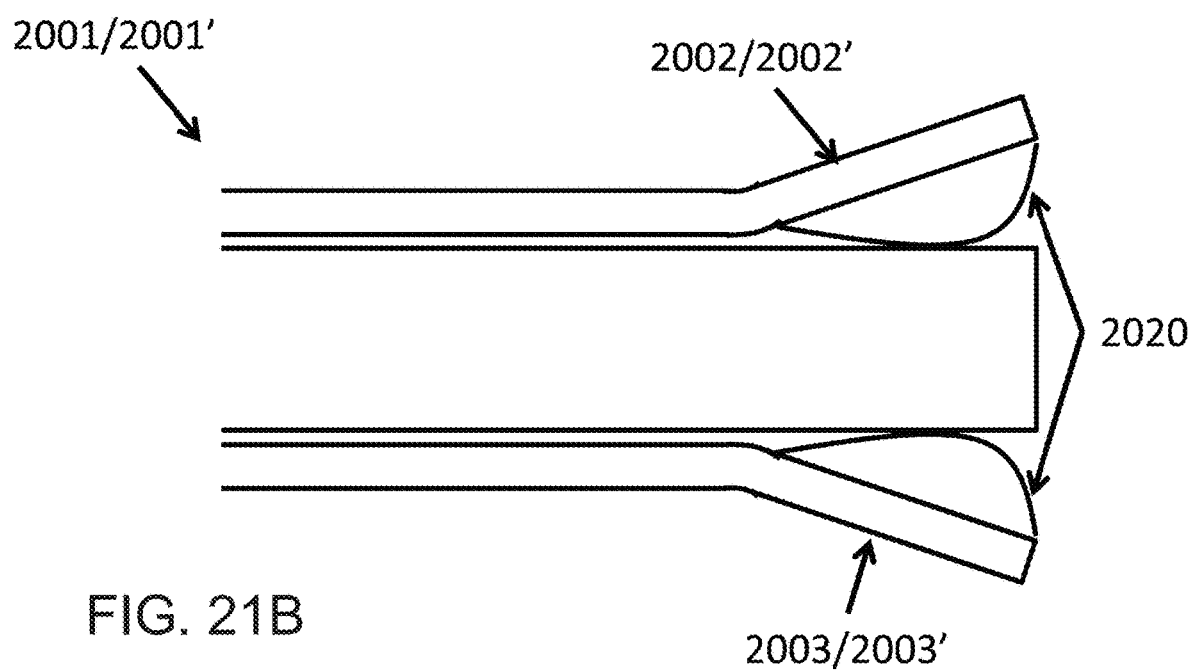

FIGS. 21A and 21B illustrate cross-sectional views of the tubular body 2001, 2001' with protrusions 2020 in the stowed and unstowed positions, respectively, in accordance with various embodiments described herein. As shown, the tissue visualization and/or ablation device can be advanced through the interior of the tubular body 2001, 2001'. As the tissue visualization and/or ablation device advances, it begins to push against the sloped edge of the protrusion 2020. The force applied to the protrusion 2020 by the tissue visualization and/or ablation device causes the first section 2002, 2002' and the second section 2003, 2003' to move apart.

The protrusions 2020 can be disposed on an interior surface of the tubular body 2001, 2001'. In various embodiments, the tubular body 2001, 2001' can include one, two, three, four, five, six, or more protrusions 2020. In the case of a single protrusion 2020, only one of the first section 2002, 2002' or the second section 2003, 2003' is actuated to divert outwardly. In some embodiments, the protrusions 2020 can be regularly spaced about the perimeter of the tubular body 2001, 2001'. In various embodiments, the protrusions 2020 are solid or fluid-filled. The protrusions 2020 can include a plastic material in some embodiments. The shape of the protrusion 2020 can be selected to cause a gentle flex motion in the first section 2002, 2002' or the second section 2003, 2003' rather than a sharp or immediate flex motion. One or more protrusions can have a concave shape so as to partially extend around the cylindrical shape of the tubular body (e.g., stylet) inserted into the working channel. Note that embodiments employing a stylet can use a stylet that is shaped to minimize or eliminate displacement of protrusions during removal. In various embodiments, the protrusions can be rigid or inflatable.

Figure 22A:
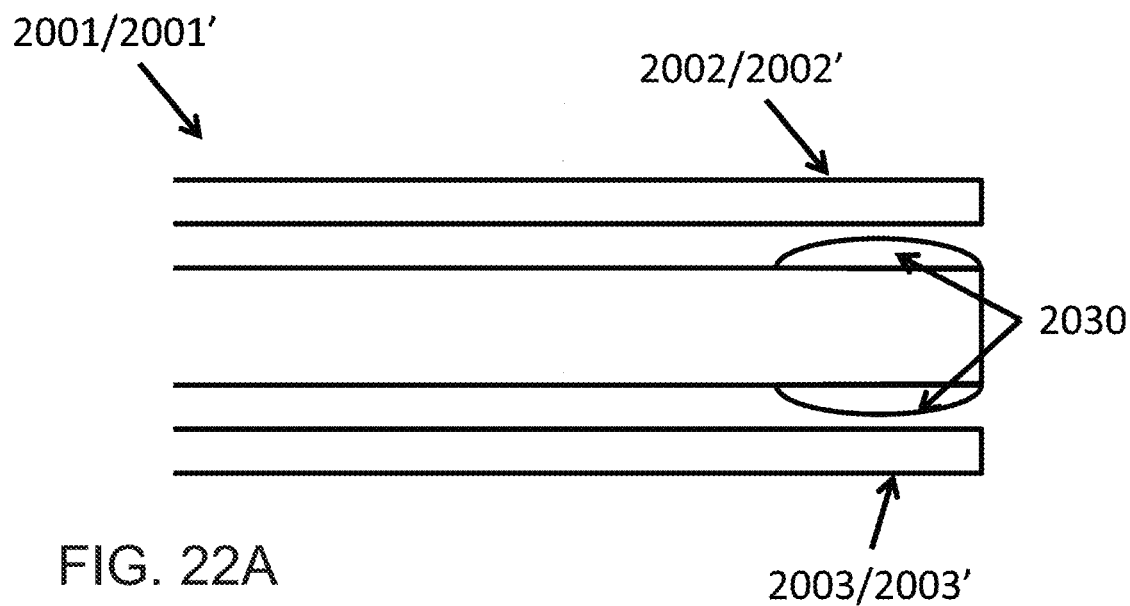
FIGS. 22A and 22B illustrate cross-sectional views of a tubular body actuated by an inflatable member in the stowed and unstowed positions, respectively, in accordance with various embodiments described herein.
Figure 22B:
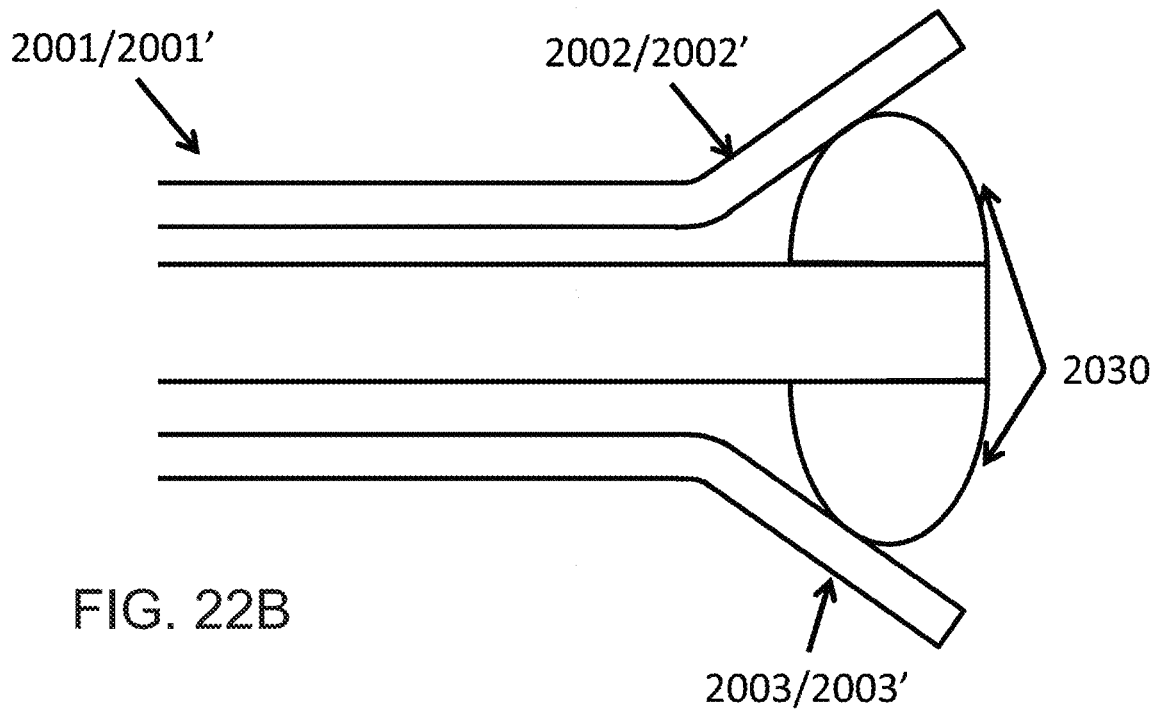

FIGS. 22A and 22B illustrate cross-sectional views of the tubular body 2001, 2001' actuated by an inflatable member 2030 in the stowed and unstowed positions, respectively, in accordance with various embodiments described herein. The inflatable member 2030 can be attached to the tissue visualization and/or ablation device and can be positioned on one side, two sides, or extend in an annular shape around the tube. When the inflatable member 2030 is activated, the inflatable member 2030 expands to apply force to the first section 2002, 2002' and/or the second section 2003, 2003' to urge the sections away from one another. The inflatable member 2030 can include a balloon that is inflated with liquid or gas in some embodiments. In some embodiments, the inflatable member 2030 can include a membrane containing a chemical that undergoes a reaction to produce gas when activated. The expanding gas can expand the membrane of the inflatable member 2030. In other embodiments, gas or liquid can be provided by a tube connected to the inflatable member 2030 from the proximal end of the tubular body 2001, 2001'. In some embodiments, the first section 2002' and the second section 2003' have sufficient stiffness/elasticity that they return to their original location (i.e., unflexed) after deflation of the inflatable member 2030.

Figure 23:
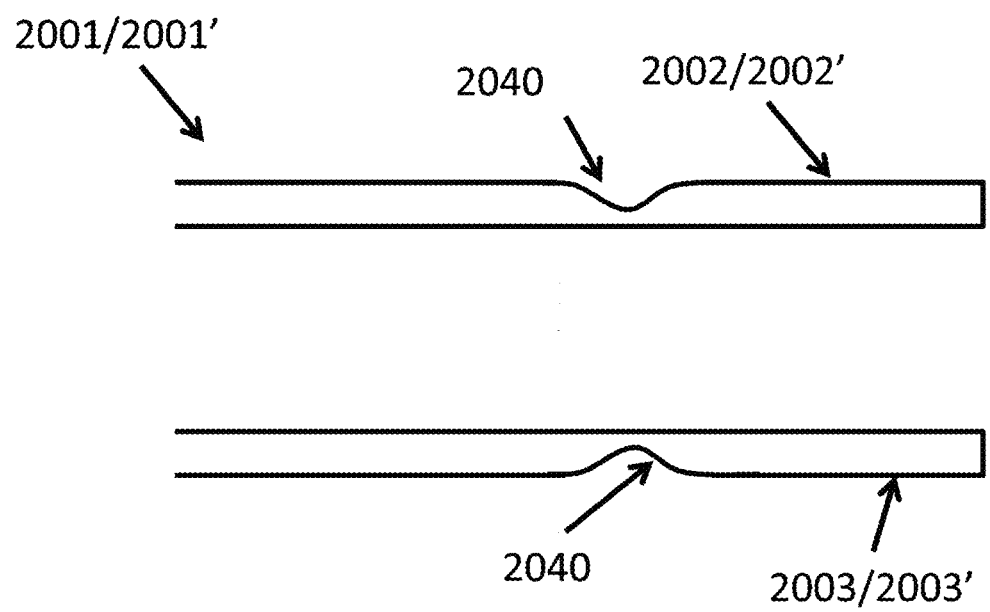
FIG. 23 illustrates a cross-sectional view of a tubular body with a thinned portion in the tube in accordance with various embodiments described herein.

FIG. 23 illustrates a cross-sectional view of the tubular body 2001, 2001' with a thinned portion 2040 in accordance with various embodiments described herein. The thinned portion 2040 provides a focus point for bending to occur thus providing predictable bending motion when the first portion 2002, 2002' or the second portion 2003, 2003' are flexed by the actuating mechanism. In some embodiments, the thinned portion 2040 can be substituted by other hinge mechanisms whereby the first section 2002, 2002' and the second section 2003, 2003' pivot about the hinge mechanism when flexed by the actuating mechanism. The point of the hinged mechanism or thinned portion 2040 may be narrow to improve the capability of the sections to flex.

Figure 24:
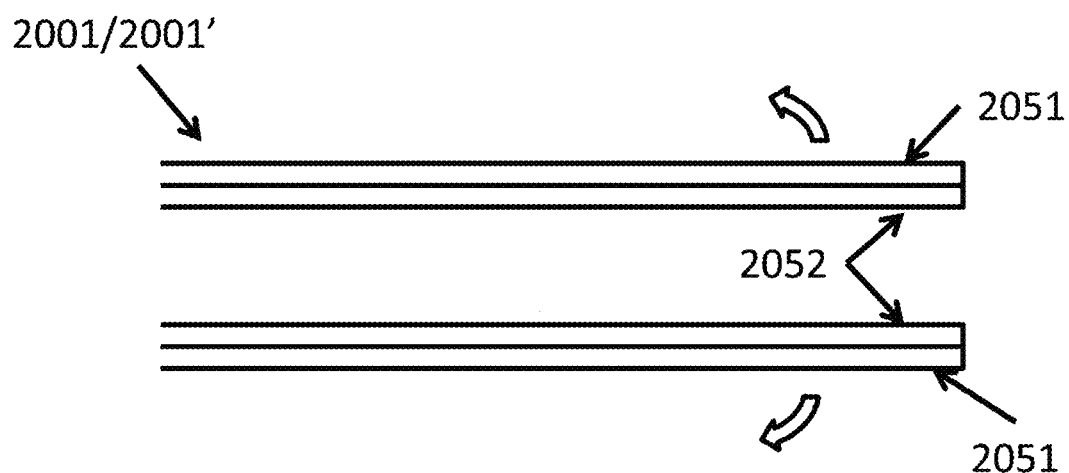
FIG. 24 illustrates a cross-sectional view of a tubular body with a tube composed of two materials with dissimilar stiffness in accordance with various embodiments described herein.

FIG. 24 illustrates a cross-sectional view of the tubular body 2001, 2001' composed of two materials with dissimilar stiffness in accordance with various embodiments described herein. The tubular body 2001, 2001' can include a first material 2051 having a first stiffness value and a second material 2052 having a second stiffness value. In some embodiments, the second stiffness value is greater than the first stiffness value. The first material 2051 and the second material 2052 can be cold-welded or co-extruded in some embodiments. When pressure is applied to the tube at the proximal end or at a selected position along the length thereof, the first section 2002, 2002' and/or the second section 2003, 2003' can preferentially flex outward due to the differential stiffness across the wall of the tubular body 2001, 2001'.

Previous embodiments described herein focused mainly on use of an inside approach to place the instruments (e.g., epiduroscope or tubular body) proximate to the tissue to be treated. However, systems and methods as described herein can also be deployed using an outside approach to the tissue. In this context, the outside approach represents a more direct approach to the tissue (e.g., ligamentum flavum) whereby the tissue can be ablated from a posterior position rather than from inside the patient. The outside approach may be contrasted to the inside approach as described previously wherein the epiduroscope is inserted into the epidural space anterior to the tissue to be ablated. The outside approach introduces a risk that the ablation tool will fully penetrate the tissue to be ablated and continue to the spinal canal where it may damage the nerves or other aspects of the spinal canal.

To mitigate the risks of accidental damage to the spinal canal, a shield can be deployed in some embodiments to protect the spinal canal from exposure to energetic ablation processes designed to remove or to reduce the volume of, for example, ligamentum flavum or vertebral discs that are compressing the spinal column. FIGS. 25A-32B illustrate a procedure for deploying a shield, ablating tissue using an external approach, and removing the shield. Although this application details the use of a shield with respect to an external approach to the ligamentum flavum, it is contemplated that the shield can be deployed as well to protect the spinal canal when an internal approach is used and no matter the tissue composition to be ablated (e.g., ligamentum flavum, vertebral disc, or other tissue).

Figure 25A:
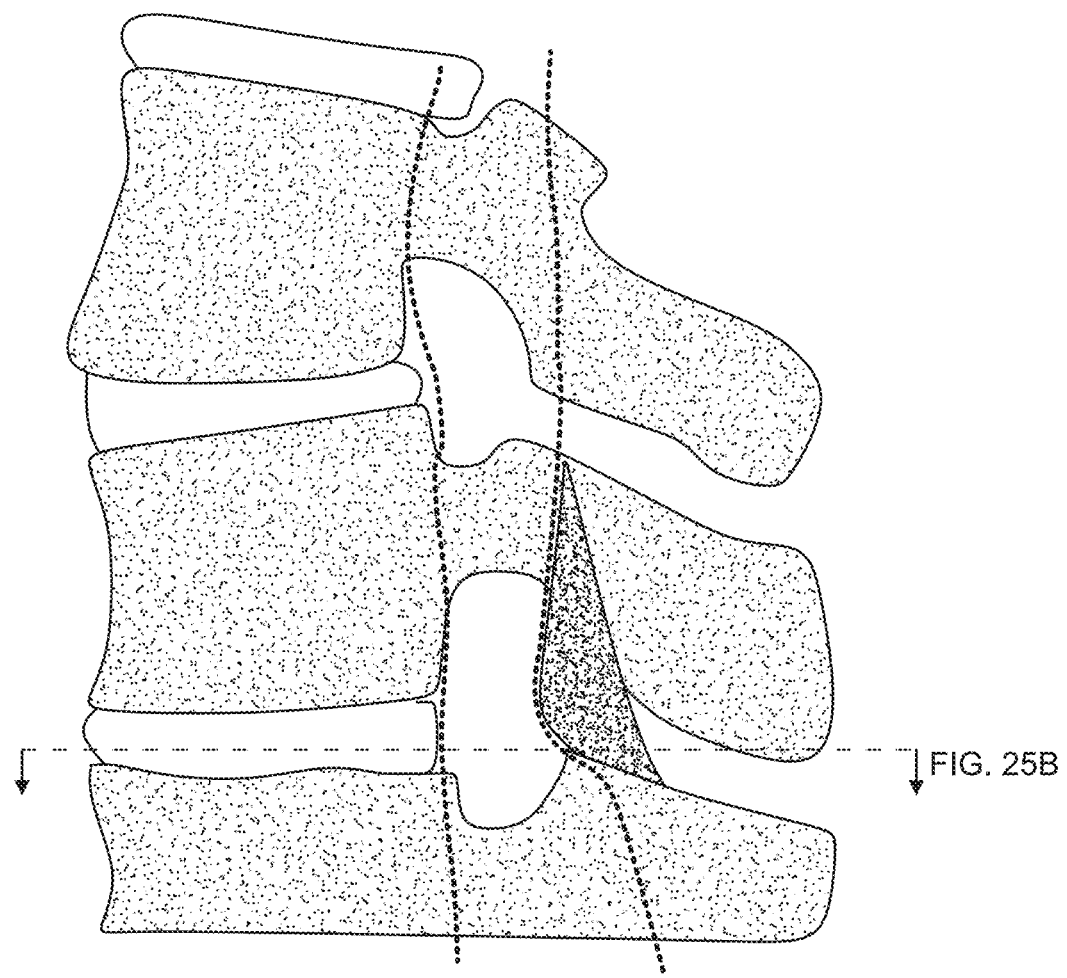
FIGS. 25A and 25B illustrate longitudinal and transverse views, respectively, of a portion of a spine having a stenosis.
Figure 25B:
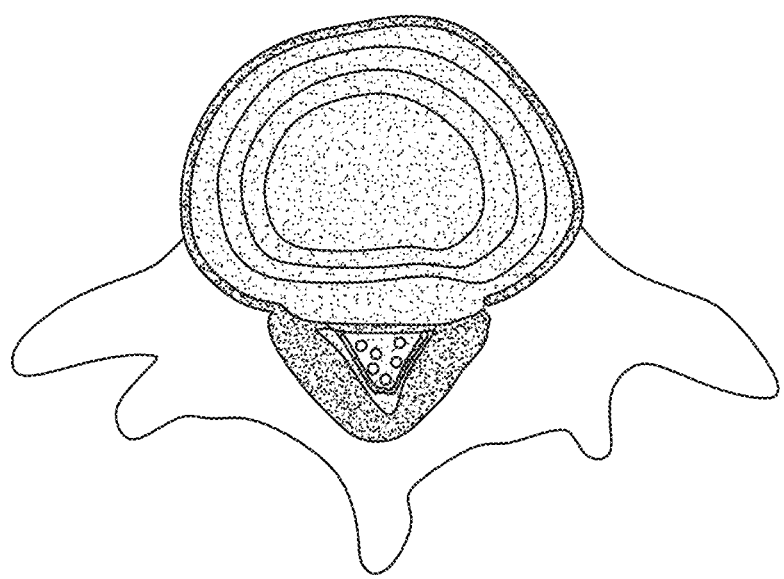
Figure 26A:
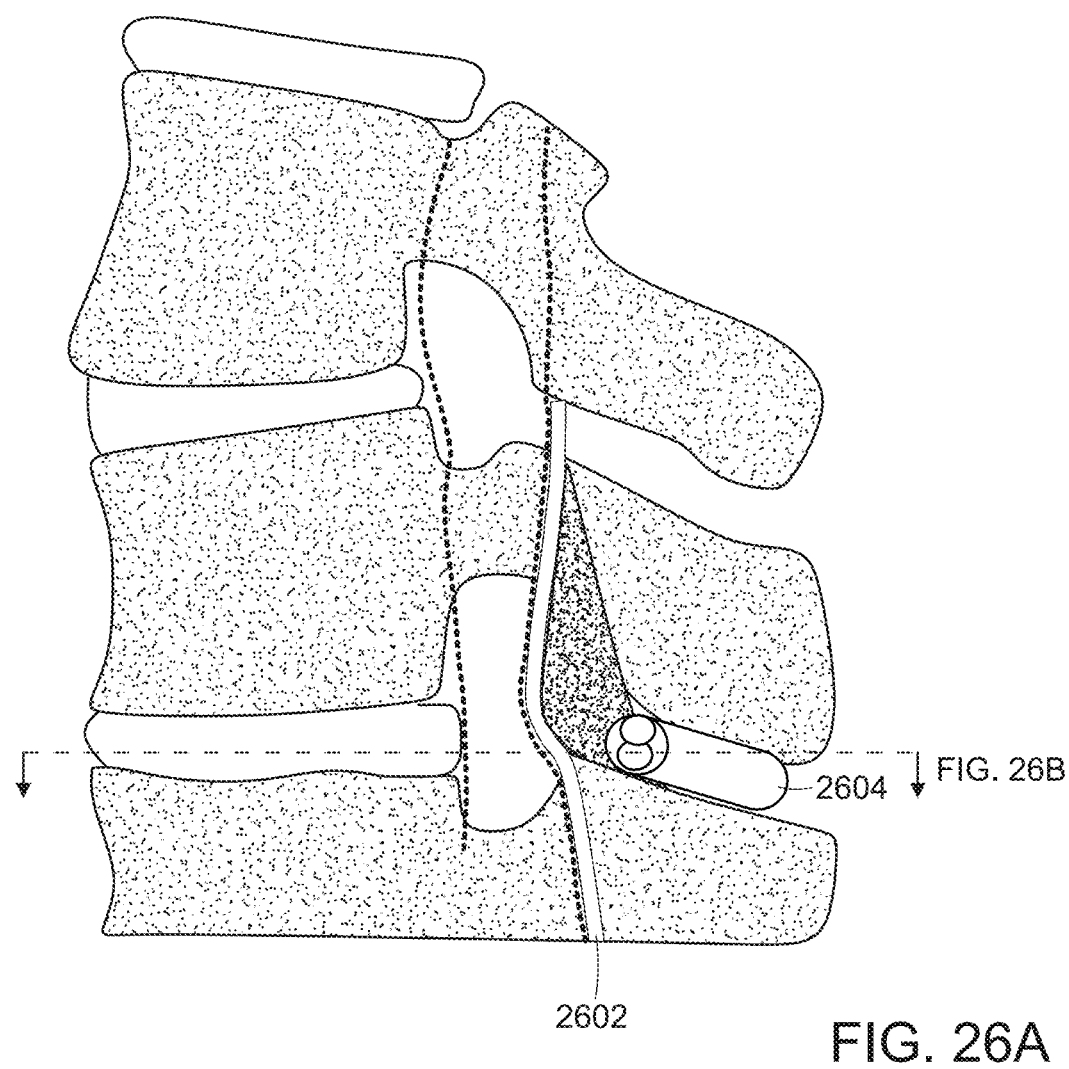
FIGS. 26A and 26B illustrate longitudinal and transverse views, respectively, of placement of a catheter in the epidural space between the ligamentum flavum and the spinal canal in accordance with various embodiments described herein.
Figure 26B:
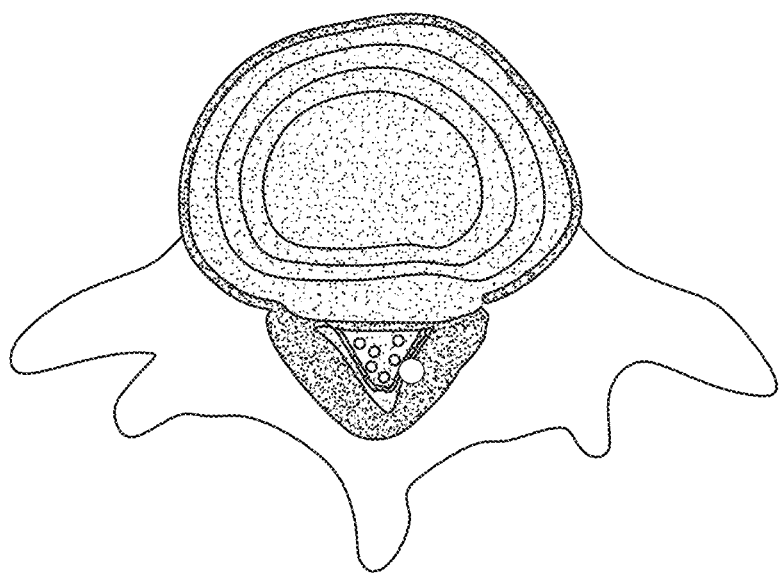

FIGS. 25A and 25B illustrate two views of a portion of a spine affected by spinal stenosis. In particular, the ligamentum flavum is enlarged and compresses the spinal column from a posterior position. FIGS. 26A and 26B illustrate two views of placement for a catheter 2602 that includes the shield and placement of the external scope 2604 for ablation of tissue using an outside approach. For example, the epiduroscopes 1700, 1800, 1900, 1950 and tubular bodies 2001, 2001', or other endoscopes (that could include posterior, anterior, or lateral approaches) described previously herein are suitable for use with this procedure. The external scope 2604 can provide both visualization of tissues and ablation (e.g., laser ablation) in a single instrument as described previously.

In some embodiments, the catheter 2602 can include a tube or tubular body having an outer diameter of less than 3 mm. In some embodiments, the catheter 2602 can have a circular or oval cross-section. An oval shape can have a diameter up to 5 mm wide and may be more shaped more advantageously geometrically for some situations. In one embodiment, the catheter 2602 can be introduced into the epidural space through the stenotic segment. Once the catheter 2602 has been placed, a shield 2610 can be deployed from inside the catheter 2602. For example, the shield 2610 can include a folded or coiled element that is retained within the catheter 2602 during catheter insertion. Then, an outer sheath of the catheter 2602 can be withdrawn and the shield 2610 can spread. In some embodiments, the shield 2610 spreads like a ribbon (eccentric or concentric). In some embodiments, the shield 2602 can include nitinol. In some instances the shield may be composed of membrane between two nitinol tines that gets deployed as the catheter is withdrawn as described below with respect to FIGS. 35A-35B. The shield 2610 can be made at least partially of a material resistant to mechanical energy, optical energy or heating. In this context, resistance indicates that the material does not allow optical energy to pass through and effectively dissipates light and heat energy. In some embodiments, the shield 2610 can be color coded and/or can be made of a radiopaque material.

The external scope 2604 can have an outer diameter of less than 5 mm in some embodiments. The outer diameter can be in a range from 3 mm to 10 mm in various embodiments. In some embodiments the external scope 2604 may have an ovoid shape. As described in relation to FIGS. 12A-16B and 19A-24, the distal tip of the external scope 2604 can include a slit or other structure that allows for dilation of the space at the tip of the external scope 2604 to increase the working field or field of view during or after placement of the external scope 2604. In some embodiments, the external scope 2604 may be rigid. In some embodiments, the external scope 2604 can include visualization channels, light emitting elements, and tissue removal devices (such as optical fibers) or other channels passing therethrough. For example, the visualization channel can include a CMOS camera that has a cross-sectional area of less than 2 mm in some embodiments. The external scope 2604 can ablate tissue using light from the optical fiber or can include other tissue removal devices such as hydrodissection, ultrasonic, coblation, and quantum molecular resonance (QMR) devices (e.g., the QMR probe from Parimed GmbH, Stansstad, Switzerland). The external scope 2604 can include one or more ports for irrigation and/or suction. In various embodiments, the visualization channel and the tissue removal device can be recessed with respect to the tip of the external scope. Because the tip can be hinged and expanded/dilated in some embodiments, the use of a recess creates an even larger field of view than if the imaging device or tissue removal device (such as an optical fiber) is even with the end of the tip. In some embodiments, an imaging device (e.g., camera) in the visualization channel can be located 2 cm away from the tissue at placement. In some embodiments, the optical fiber can be located 2 cm away from the tissue at placement. As described in greater detail below, the tissue removal device may be advanced directly to contact the tissue for ablation such as with hydrodissection, ultrasonic techniques, coblation and quantum molecular resonance while a distal end of the imaging device remains recessed within the external scope 2604.

Figure 27A:
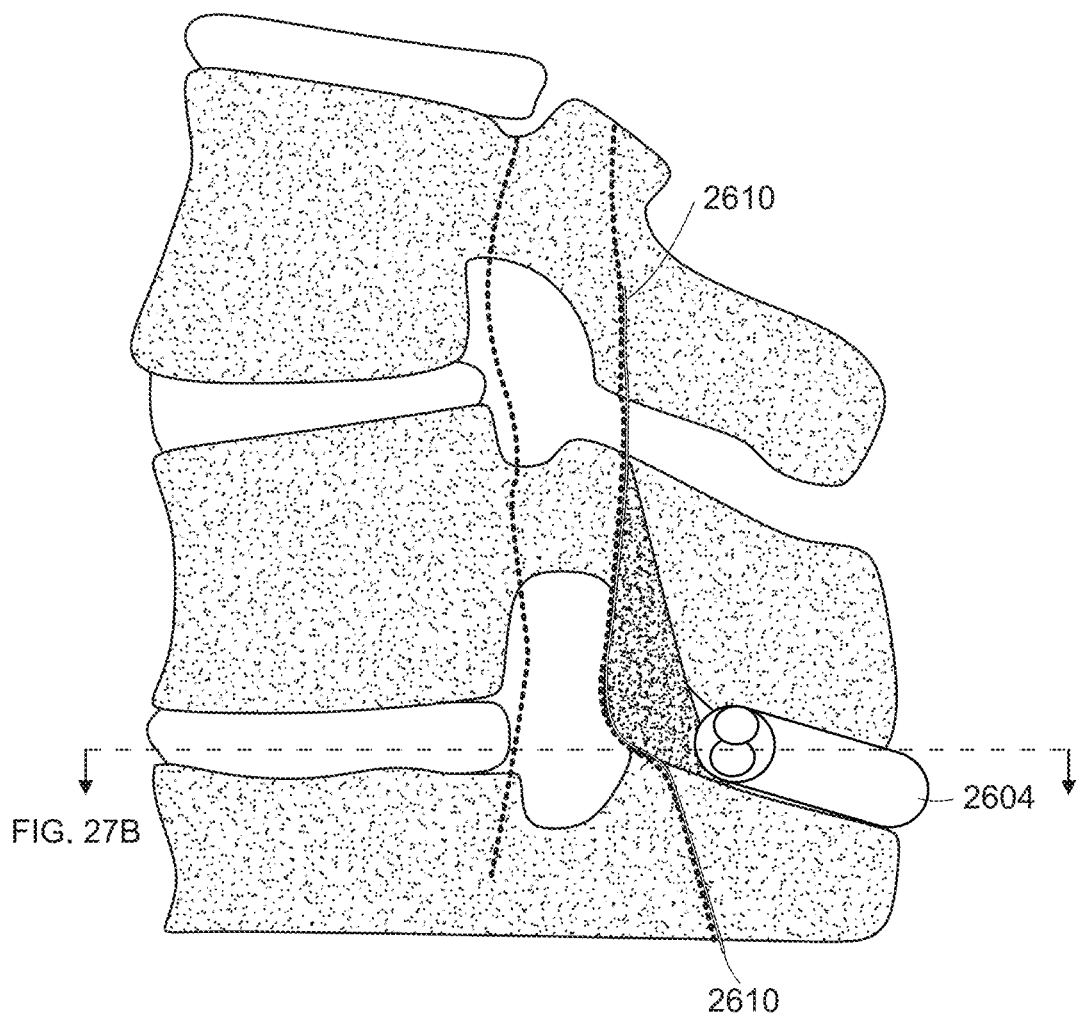
FIGS. 27A and 27B illustrate longitudinal and transverse views, respectively, of retraction of an outer sheath of the catheter and insertion of a tubular body using an outside approach in accordance with various embodiments described herein.
Figure 27B:
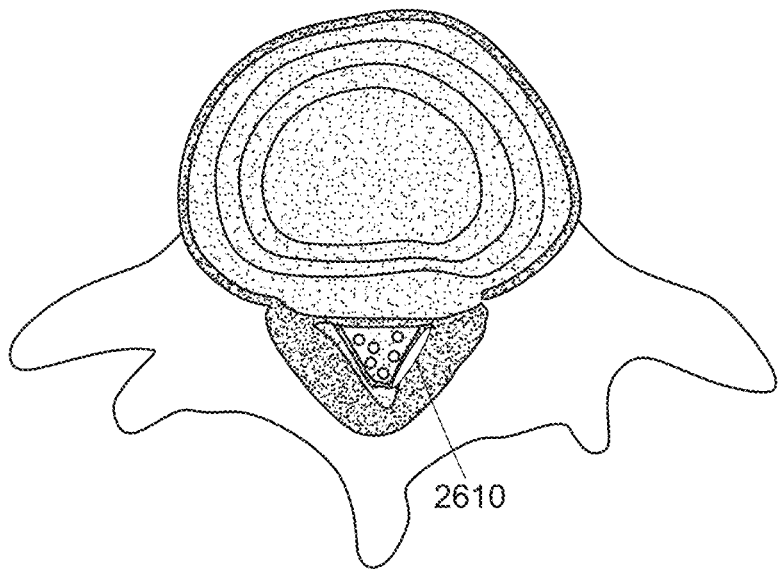

FIGS. 27A and 27B illustrate views of the resulting configuration after withdrawal of the catheter 2602 to allow the shield 2610 to expand. The shield 2610 protects the spinal canal from the energy of ablation. The shield 2610, in its unfolded state, can include a circular or rectangular element. In some embodiments, a diameter of the shield 2610 can be in a range from 1.5 cm to 5 cm. In some embodiments, a width of the shield 2610 may be in a range from 2 mm to 10 mm. In some embodiments, a length of the shield 2610 may be in a range from 2 cm to 10 cm. In some embodiments, a thickness of the shield 2610 may be in a range from 0.1 mm to 1.5 mm.

Figure 28A:
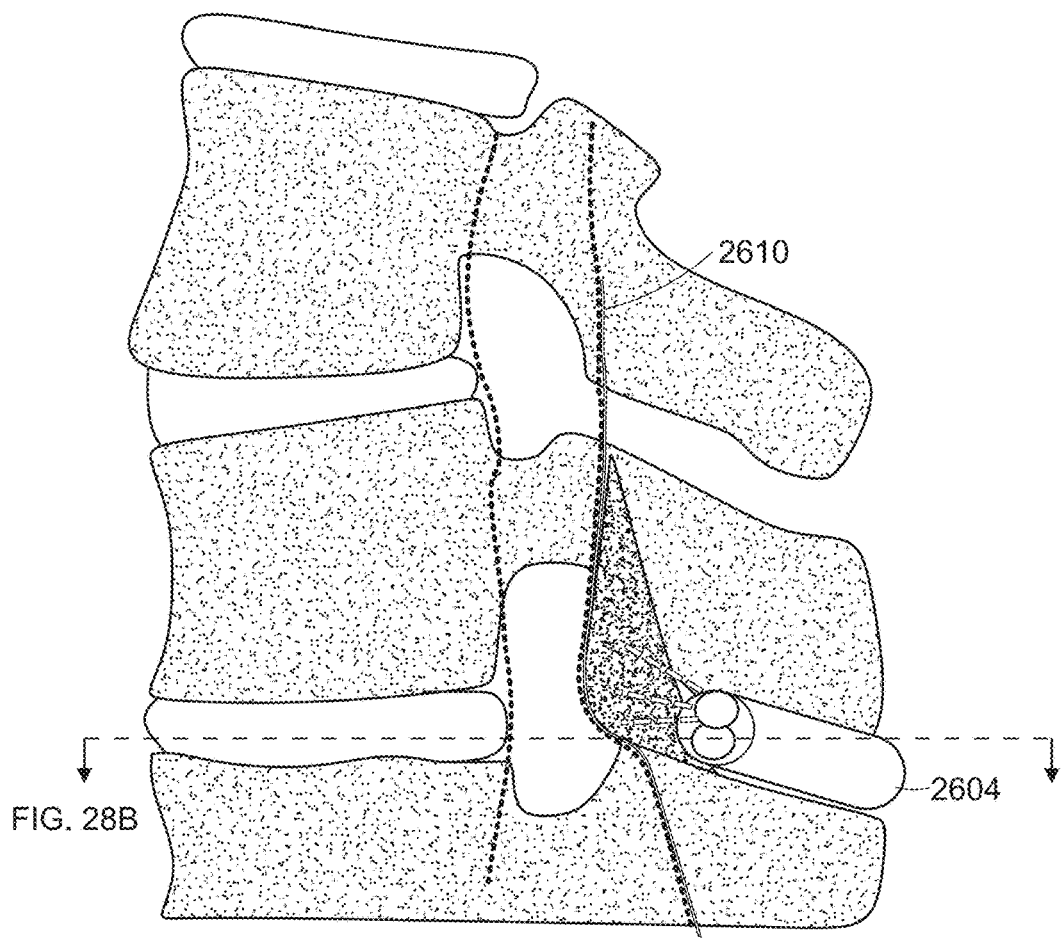
FIGS. 28A and 28B illustrate longitudinal and transverse views, respectively, of ablation of a portion of the ligamentum flavum using an energy source in accordance with various embodiments described herein.
Figure 28B:
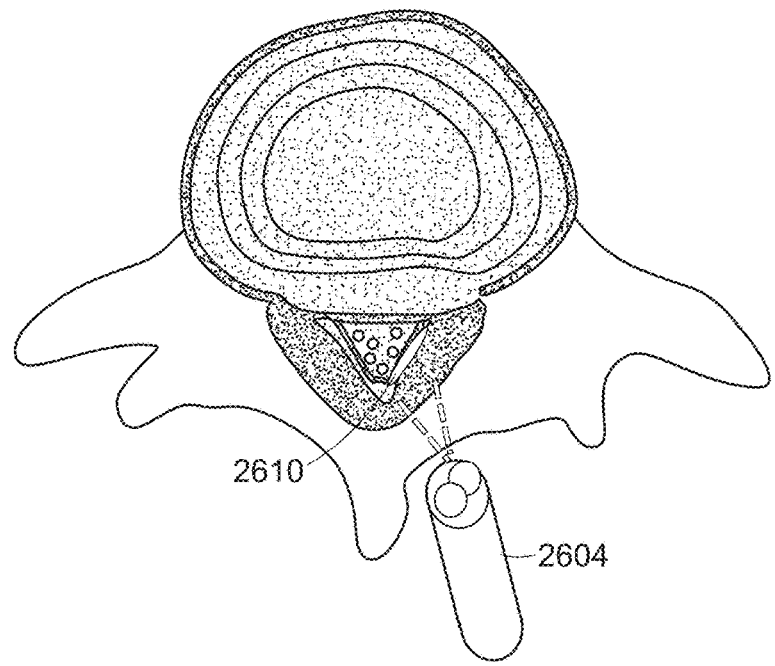

FIGS. 28A and 28B illustrate views of the process of laser ablation using light from an optical fiber in the external scope 2604. In some embodiments, the optical fiber can include a carbon-dioxide ($CO_2$) laser fiber with an outside diameter of 1.02 or 1.2 mm. The tip of the optical fiber can be formed of a metallic material in some embodiments to protect the optical fiber and improve efficiency. A relatively inert gas (e.g., helium or nitrogen) can be infused at a rate of 1-2 liters per minute through a central port to cool the laser. Depending upon the circumstances, higher or lower flows can be used. For ablation operations in the epidural space, $CO_2$ can be used although laser output energy will be diminished. In some embodiments, the $CO_2$ laser can be operated in super pulse mode to reduce charring and maximize ablation of the tissue. During ablation, a port or channel on the external scope can be used for suction to remove smoke and minute debris and/or irrigation to remove charring. The irrigation may be intermittent in some embodiments. The optical fiber can output 15W of power at the tip in some embodiments. At such a power level, one gram of ligamentum flavum can be reduced to half a gram after 2 minutes of ablation. In a typical procedure, the amount of ligamentum flavum to be removed for relief of spinal stenosis varies between 1 gram and 4 grams per level (i.e., per vertebra). Comparatively, one gram of vertebral disc can be reduced to half a gram after 1.5 minutes of ablation, and the amount of disc tissue that must be removed to relieve stenosis can be as low as one gram in some embodiments.

Figure 29A:
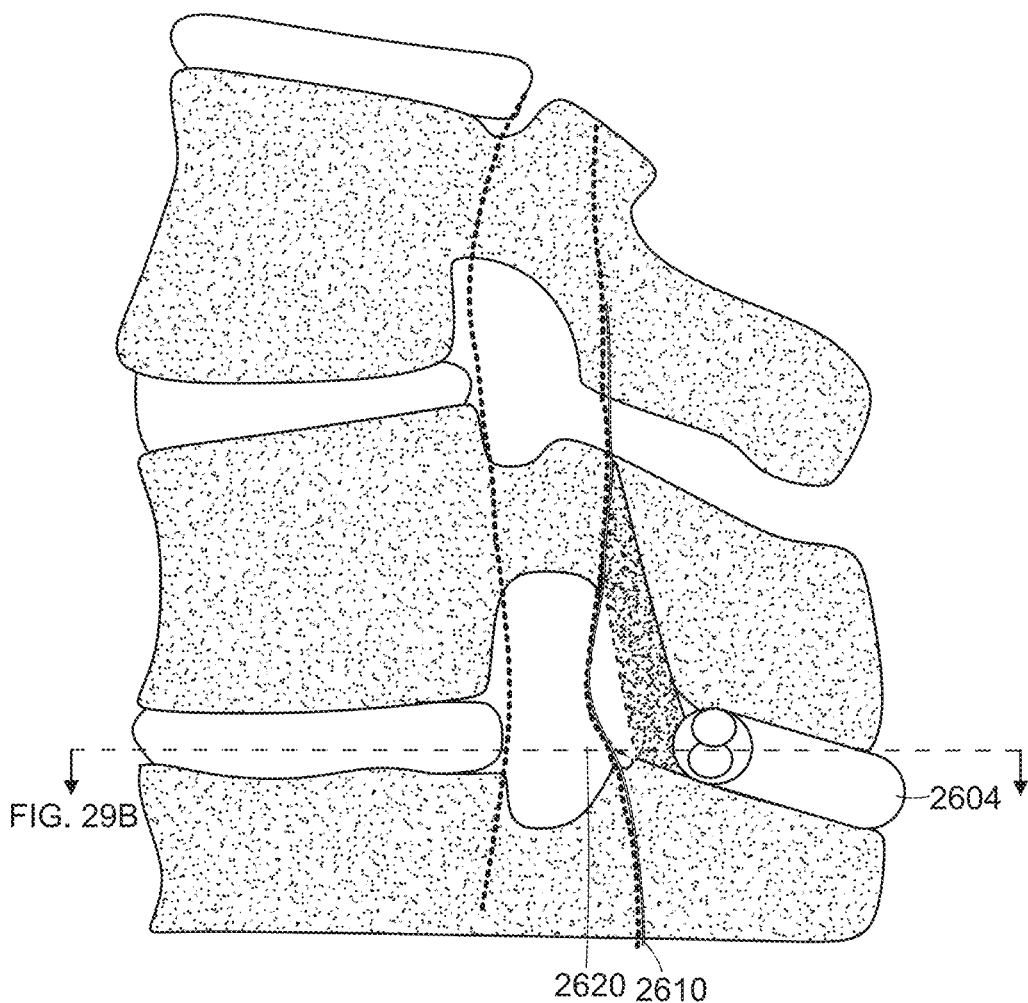
FIGS. 29A and 29B illustrate longitudinal and transverse views, respectively, of the ligamentum flavum after ablation in accordance with various embodiments described herein.
Figure 29B:
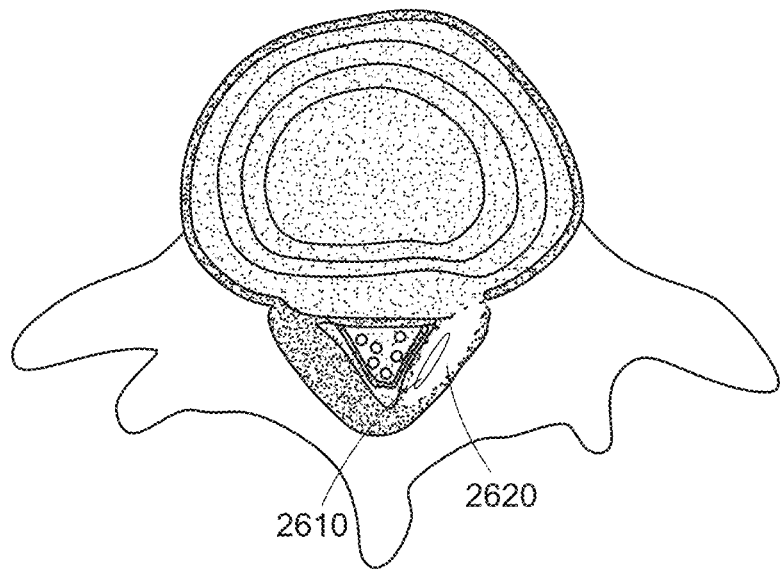
Figure 30A:
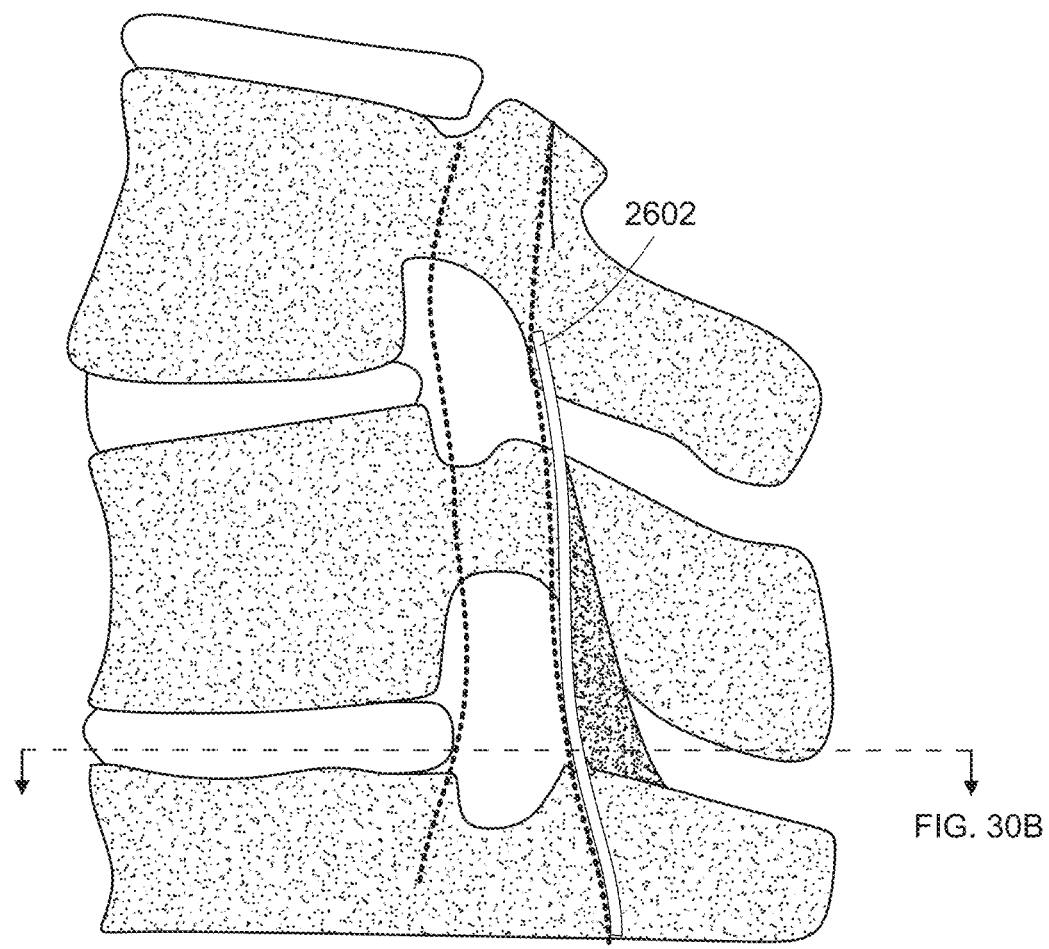
FIGS. 30A and 30B illustrate longitudinal and transverse views, respectively, of re-insertion of the catheter and removal of the tubular body in accordance with various embodiments described herein.
Figure 30B:
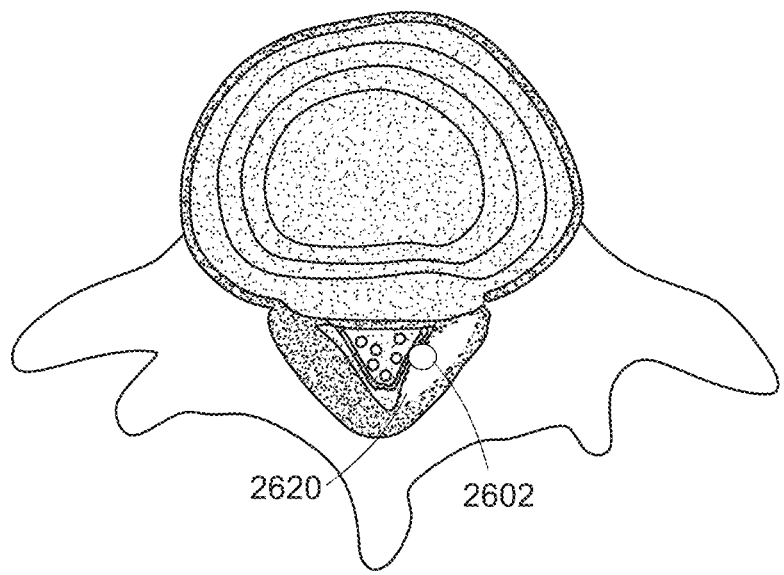
Figure 31A:
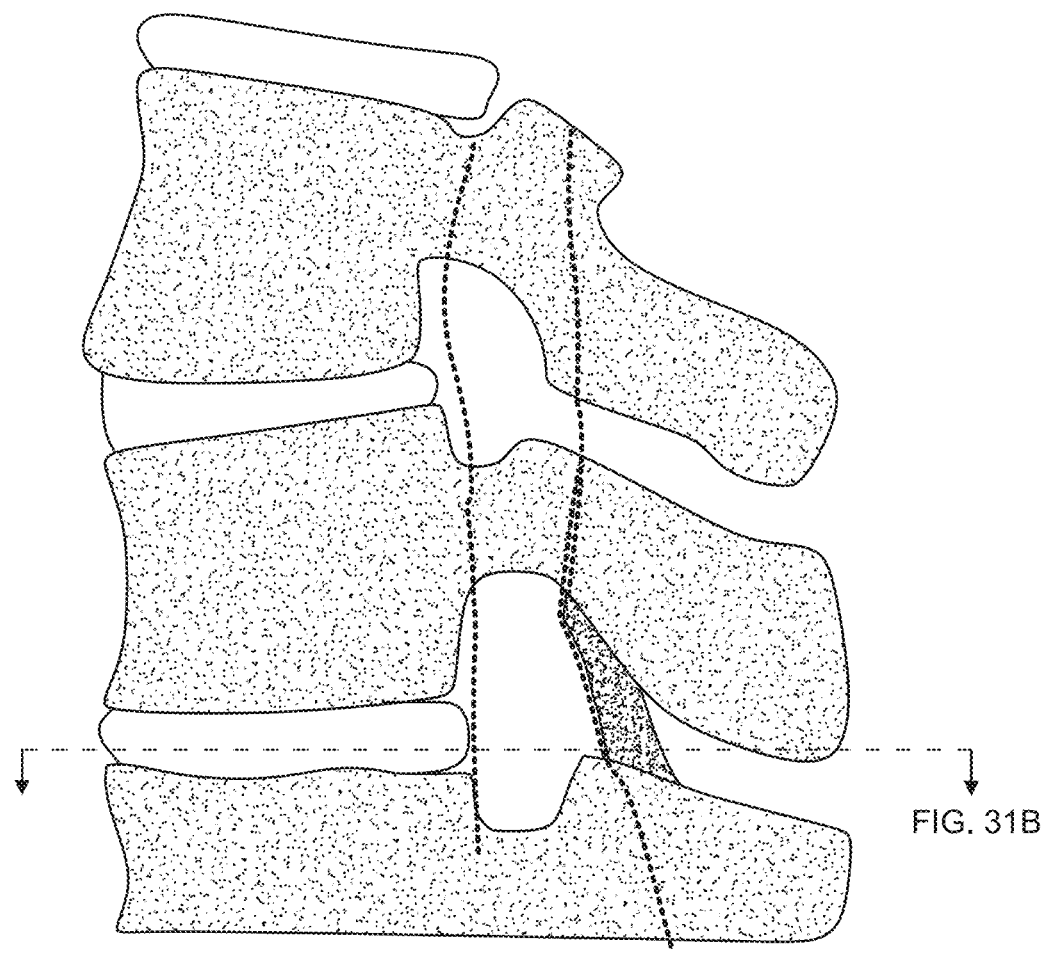
FIGS. 31A and 31B illustrate longitudinal and transverse views, respectively, of placement of the portion of the spine with alleviated stenosis.
Figure 31B:
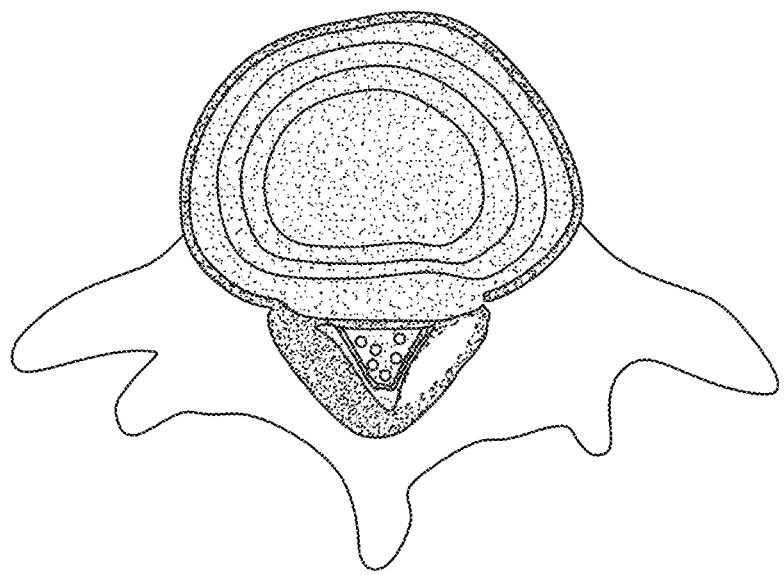

FIGS. 29A and 29B illustrate views of the spine at the end of the ablation process. The removed portion 2620 surround by a lightly dashed line indicates the extent of the bulging ligamentum flavum that has now been removed. FIGS. 30A and 30B illustrate views of the spine after the catheter 2602 has been advanced back over the shield 2604. In some embodiments, the construction of the shield 2610 is configured to promote folding or collapsing of the shield 2610 upon application of pressure from the advancing outer sheath of the catheter 2602. For example, the shield 2610 can include ribbing or other structural elements that cause the shield 2610 to fan out when the catheter is retracted and fold up when the catheter is advanced. Once the catheter has been replaced, the external scope 2604 and catheter 2602 including the folded or compressed shield 2610 can be removed from the body. FIGS. 31A and 31B illustrate views of the final anatomical configuration wherein stenosis caused by a bulging ligamentum flavum has been alleviated.

Upon completion of the procedure detailed in FIGS. 25A-31B, the catheter 2602 can be extended or relocated to a different position rather than removed. For example, the catheter and shield can be repositioned behind the ligamentum flavum on the same side or the opposite lateral side to facilitate removal of the ligamentum flavum on that side. Alternatively or in addition, the catheter 2602 can be advanced or retracted vertically (i.e., along the spinal canal) to facilitate removal of ligamentum flavum or other tissue at a different vertebra.

Although the procedure detailed in FIGS. 25A-31B describes removal of ligamentum flavum, it is contemplated that a similar procedure could be used for vertebral disc ablation as well as ablation of ligamentum flavum from within the epidural space (interior approach). In such a procedure, the catheter 2602 can be advanced into the posterior epidural space over the ligamentum flavum or the anterior epidural space over the herniated disc. The shield 2610 can be deployed by retracting the outer sheath of the catheter 2602. The external scope 2604 can be inserted using an interior approach and ablation can commence. After ablation has occurred, the shield 2610 can be stowed and the catheter 2602 and external scope 2604 withdrawn.

When using alternative ablation methods to laser ablation in the tissue removal device such as ultrasonic, hydrodissection, coblation or QMR, it may be desirable to provide continuous saline irrigation through the external scope 2604 rather than intermittent irrigation. In such cases, the tissue removal device can be mobile to directly contact the tissue.

Figure 32:
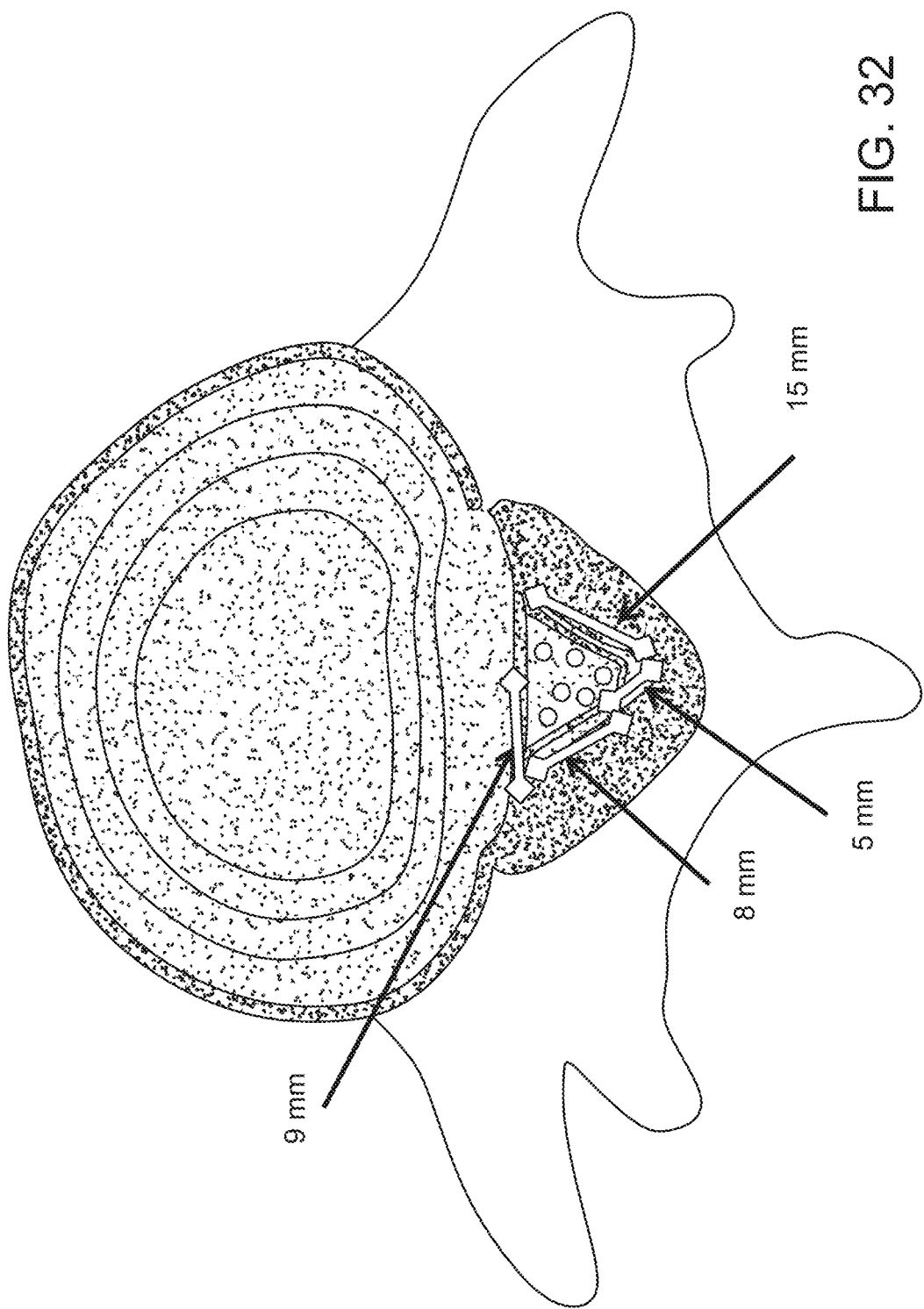
FIG. 32 illustrates anatomical measurements on a radiographic image to aid in determination of the appropriate shield size in accordance with various embodiments.

In some embodiments, more than one catheter and shield may be deployed to protect larger areas. In FIG. 32, measurements are obtained from a radiographic image of a spine to aid in a determination of the size of shield 2610 that is desirable to deploy. For example, the distance along the ligamentum flavum to the right of the spinal canal is about 15 mm. This could be covered by a single shield in some embodiments. In other embodiments, two shields of the same or dissimilar sizes could be deployed side-by-side or one-in-front-of-the-other. For example, the distance along the ligamentum flavum to the left of the spinal canal could be protected by two shields measuring 8 mm and 5 mm. Similarly, the half-distance along the vertebral disc anterior to the spinal canal measures about 9 mm in this patient. Thus, a single 18 mm shield could be deployed or, alternatively, two 9 mm shields could be deployed in various embodiments.

Figure 33A:
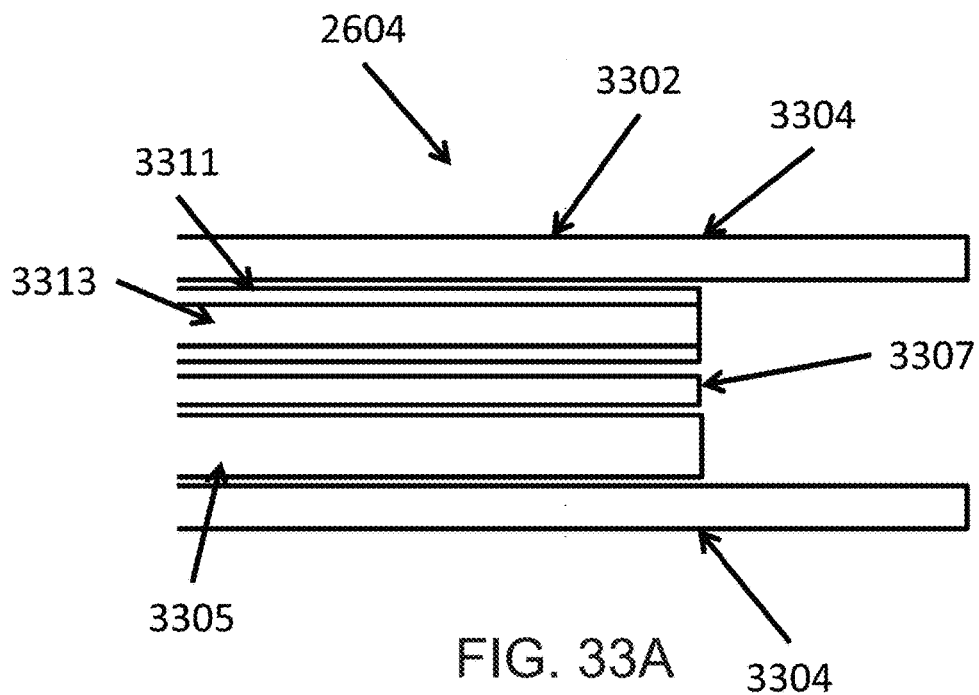
FIGS. 33A and 33B show cross-sectional views of an external scope before and after dilation of the distal tip, respectively.
Figure 33B:
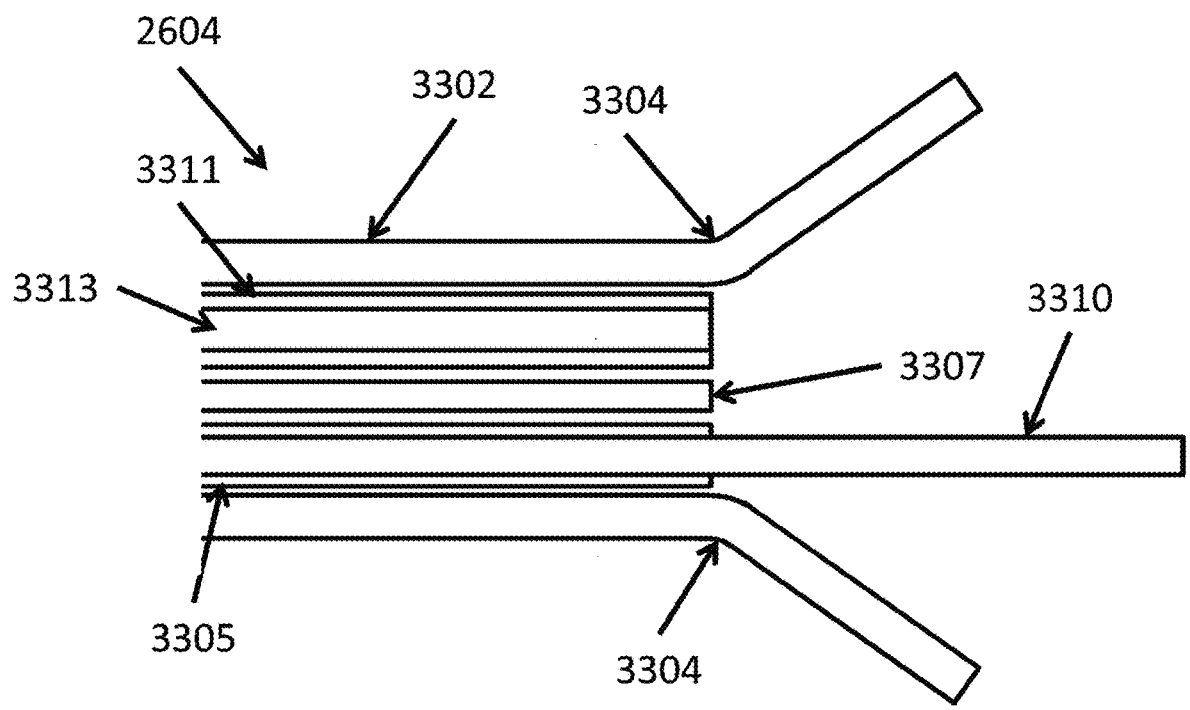

FIGS. 33A and 33B illustrate the external scope 2604 before and after dilation of the distal tip, respectively, to increase the field of view in accordance with various embodiments described herein. The external scope 2604 can include multiple elements included within by the tubular body 3302. In some embodiments, the tubular body 3302 has one or more hinges 3304. In some embodiments, a visualization channel 3311 lies within the tubular body 3302 through which imaging devices and/or illumination devices 3313 can be deployed. In some embodiments, elements within the visualization channel 3311 can be advanced or retracted with respect to the distal end 3301 of the tubular body. For example, the imaging device 3313 can be positioned several centimeters away from the distal end 3301 within the tubular body 3302. The imaging device 3313 can be positioned proximal to the hinge 3304 in some embodiments. A fluid channel 3307 can be included in the tubular body 3302. The fluid channel 3307 can be used to flow liquid (e.g., saline) to the distal end 3301 of the external scope 2604 in some embodiments. In some embodiments, the fluid channel 3307 can be used to suction fluids or gases (e.g., smoke) away from the distal end 3301 and through the fluid channel 3307.

The external scope 2604 can include a working channel 3305 through which tools or devices to cut or ablate tissue may pass. For example, a tissue removal device 3310 may pass through the working channel 3305. The tissue removal device 3310 can extend from the working channel 3305 or be contained entirely within the working channel 3305 in different embodiments. The tissue removal device 3310 can be extended or retracted relative to the working channel 3305 in some embodiments. The tissue removal device 3310 can include devices that apply energy to the tissue to burn, cut, singe, or ablate the tissue. The tissue removal device 3310 can utilize laser light, heat, electricity, ultrasound, coblation, QMR, or other techniques to affect the tissue. In embodiments that utilize laser light, the tissue removal device 3310 may be substantially in the form of an optical fiber as described above. In such an embodiment, it may be desirable to position the distal end of the tissue removal device 3310 at a recessed location with respect to the distal end 3301 of the tubular body. In other embodiments wherein the tissue removal device 3310 operates by directly contacting tissue, the tissue removal device 3310 can extend beyond the distal end 3301 of the tubular body 3302.

As shown in FIG. 33B, the distal end 3301 of the tubular body 3402 may be dilated upon deployment in some embodiments. Expansion of the diameter of the distal end 3301 may be accomplished as described above with respect to FIGS. 19A-24 in some embodiments. In some cases, only one hinge 3304 is deployed. By holding the imaging device 3313 and the tissue removal device 3310 at a recessed position relative to the distal end 3301 and dilating the distal end 3301, an increased field of view is obtained. In addition, the setback may enable improved focusing for the tissue removal device 3310 in the form of a laser because the focal point can be located, e.g., several centimeters away from the end of the tissue removal device 3310.

Figure 34A:
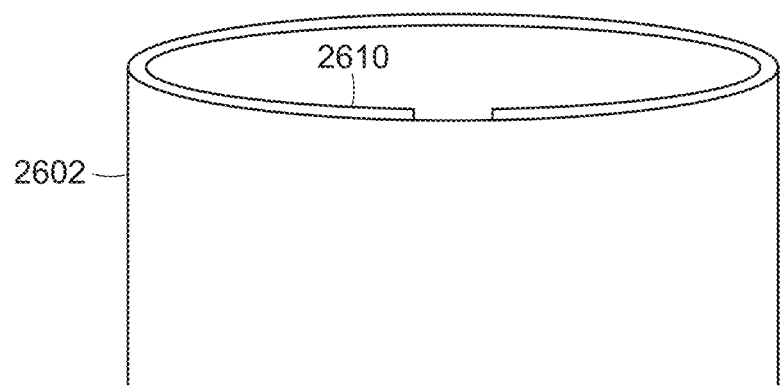
FIGS. 34A-34C illustrate progressive stages of deployment of a shield from a catheter in accordance with embodiments described herein.
Figure 34B:
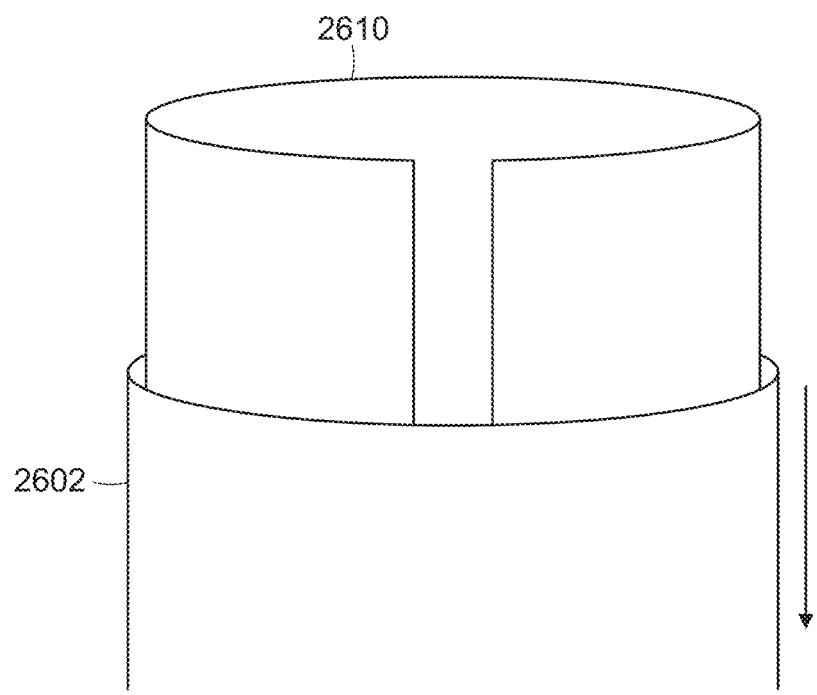
Figure 34C:
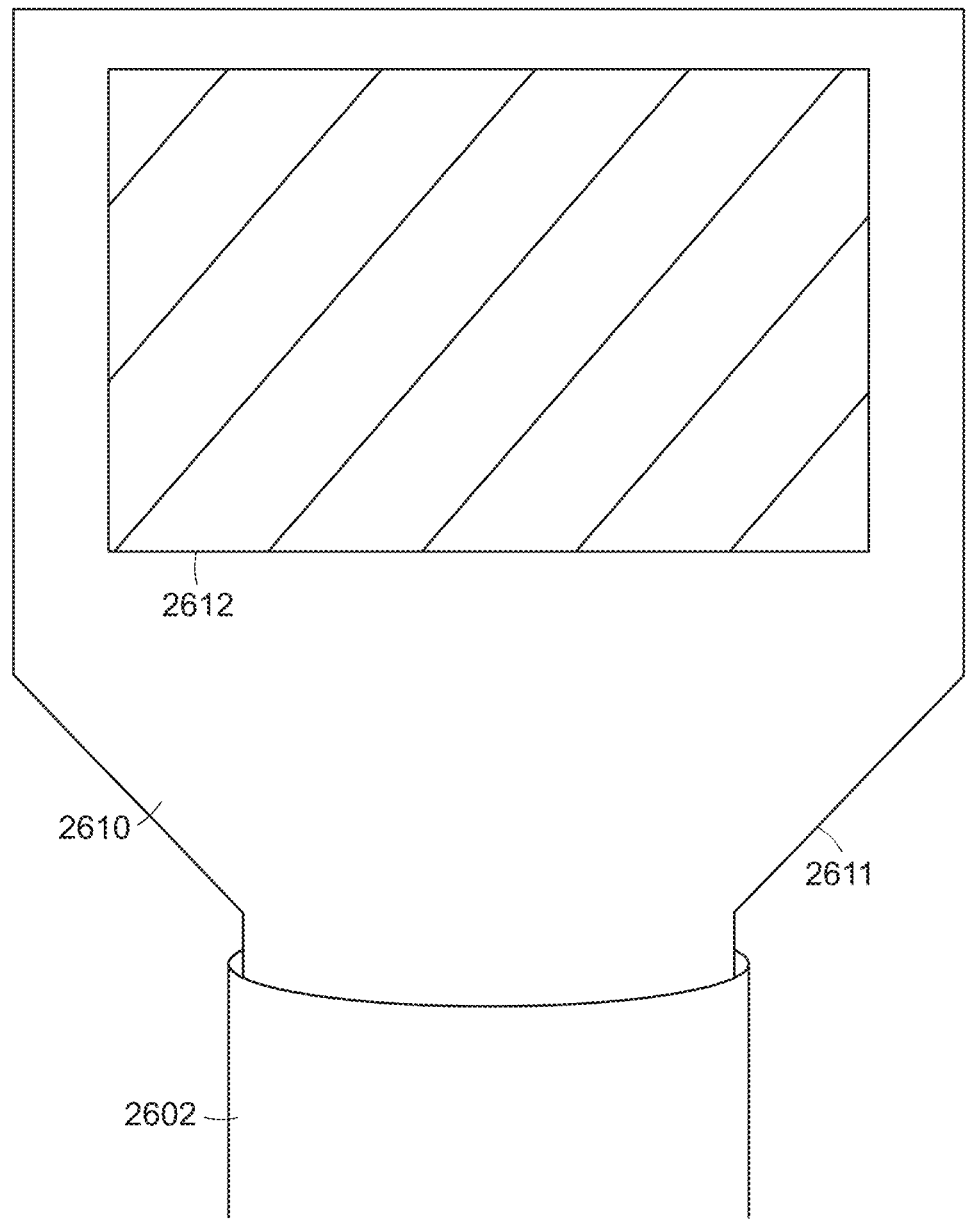

FIGS. 34A-34C depict deployment of the shield 2610 from the catheter 2602 according to some embodiments. In FIG. 34A, the catheter 2602 has been advanced to the proper position for deployment of the shield 2610 within the epidural space of the patient. The shield 2610 is still folded within the catheter 2602 at this stage. In FIG. 34B, the catheter 2602 is retracted to begin to expose the shield 2610. As the catheter 2602 retracts, the exposed portion of the shield 2610 may retain its folded character or may begin to unfold. When the narrowing portion 2611 of the shield 2610 extends out from the catheter 2602, the shield 2610 begins to expand and unfold. The final, unfolded shield 2610 is depicted in FIG. 34C. After the procedure, the catheter 2602 can be advanced over the shield 2610. As the catheter 2602 advances, the catheter engages with the narrowing portion 2611 to urge the shield 2610 back into a folded position.

As noted previously, the shield 2610 can be formed at least in part of nitinol. In some embodiments, the shield 2610 includes more than one component such as a polymer membrane with a second component embedded therein. For example, the shield 2610 can include a polymer membrane at the narrowing portion 2611 and forming a full or partial frame around a target region 2612. The target region 2612 can include nitinol that is untreated or treated with an agent that increases resistance to the energy of ablation, e.g., laser energy.

Figure 35A:
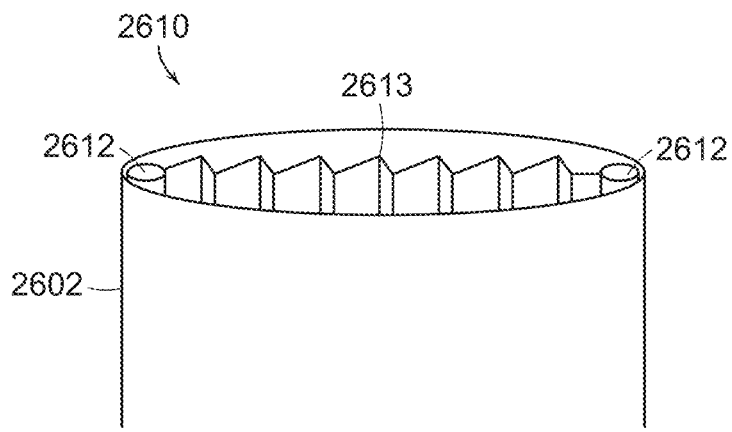
FIGS. 35A-35B illustrate deployment of a shield having a membrane and tines in accordance with embodiments described herein.
Figure 35B:
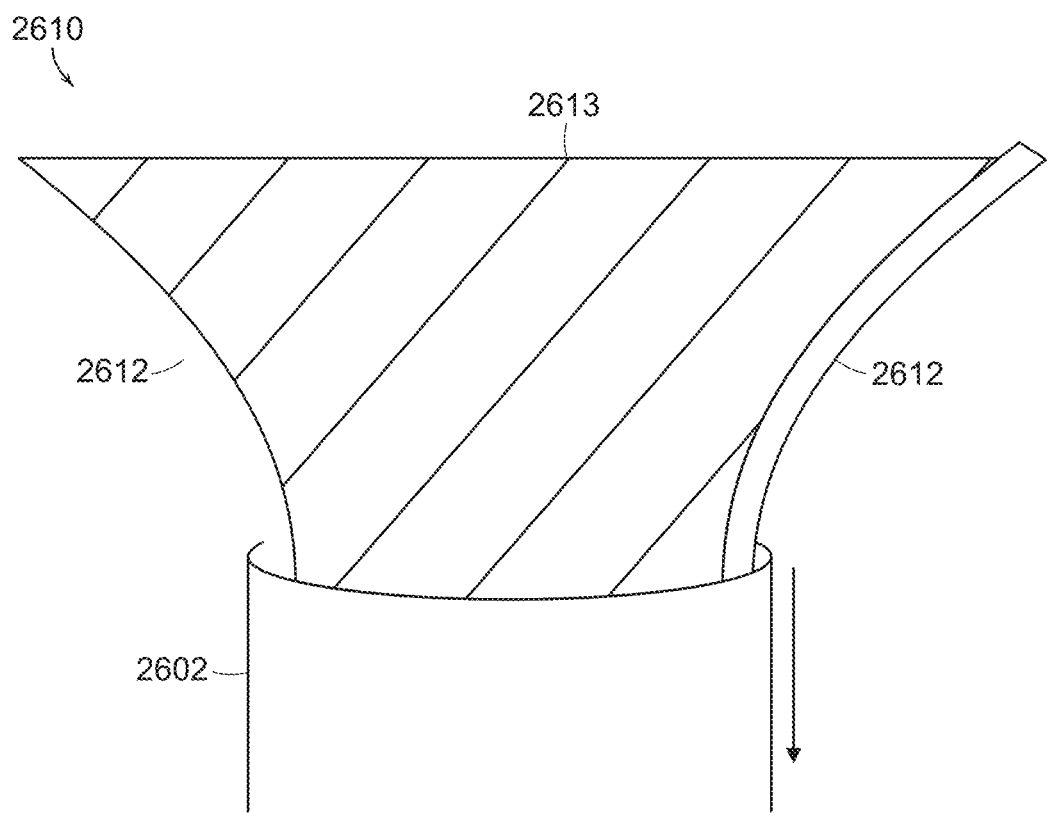

FIGS. 35A and 35B illustrate a shield 2610 having a membrane 2613 attached to tines 2612. The tines 2612 may be formed of nitinol or a shape memory metal, for example. The tines 2612 may be pre-stressed such that they curve outward or desire to bend outward or curl. In FIG. 35A, the shield 2610 is stowed inside the catheter 2602. In FIG. 35B, the catheter 2602 is retracted and the shield 2610 extends from the end of the catheter 2602. As the tines 2612 exit the catheter 2602, the tines 2612 bend outward to unfold the membrane 2613. The membrane 2613 thus extends beyond the diameter of the catheter 2602 to create a larger protective area to protect the spinal canal/nerves/dura mater from exposure to the energy of ablation during a procedure.

FIGS. 36-41 illustrate transverse views of steps of a procedure for spinal decompression using a contralateral approach to insert a surgical tool to remove the stenosis. Conventional methods have been developed for minimally invasive lumbar decompression (MILD). However, these conventional procedures have several drawbacks. First, conventional methods typically use an ipsilateral (same side) approach from inferior segment for inserting the instruments. However, the stenosis is often more pronounced laterally in the lateral recess and this approach from the inferior segment means that it is difficult to enter the area. Further, conventional methods attempt to introduce a safety zone inside the epidural space by injection of liquid contrast agent. The liquid contrast agent is intended to provide visual contrast of the boundary of the hypertrophied ligamentum flavum as well as to establish space between the flavum and the spinal canal. However, the injection of liquid contrast is frequently problematic as the dye immediately follows the path of least resistance and flows away from the most restricted area. Additionally, a fluid bolus will have variable appearance in depth depending on where it spreads. Moreover, it is often not possible to further compress tissue in this area as there is very little space due to the stenosis.

FIG. 4 illustrates a portion of a spine having a stenosis caused by bulging ligamentum flavum. The stenotic vertebral level is first identified using conventional imaging techniques. The laminae above and below the stenosis are identified using the x-ray images or magnetic resonance imaging (MRI).

Figure 36:
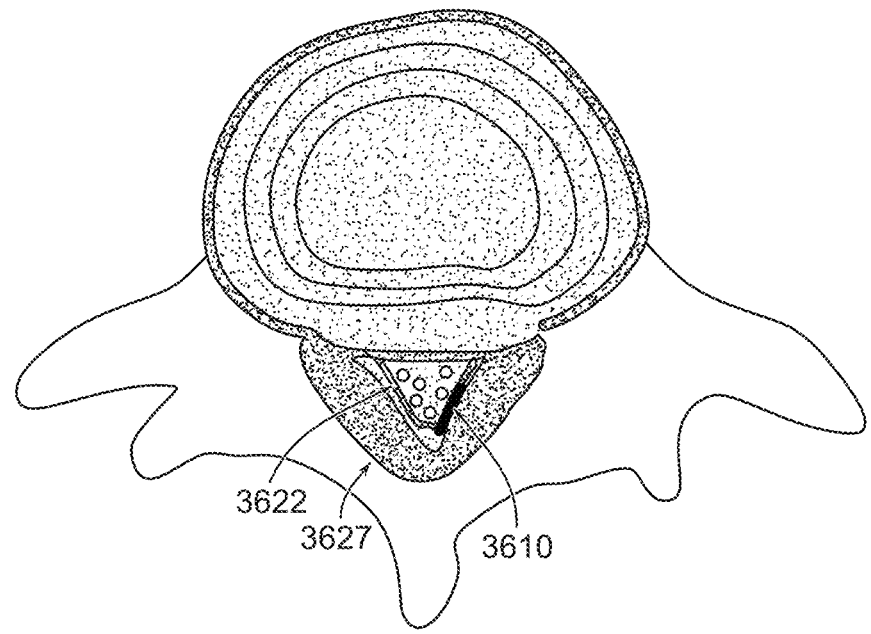
FIGS. 36-41 illustrate transverse views of steps of a procedure for spinal decompression using a contralateral approach.

FIG. 36 illustrates placement of a wire or sheath that operates as a protective membrane 3610 between the thecal sac 3622 and the ligamentum flavum 3627. The placement of the wire or sheath 3610 is preferred and can demarcate the safety zone. The safety zone is the space within which surgical tools can operate to decompress the stenosis without damaging nerve tissue in the thecal sac. To place the wire or sheath, a needle is inserted into the epidural space at a less stenotic or non-stenotic level. In exemplary embodiments, the level where the needle is inserted is below the stenosis or sacrum. A wire is placed and the needle is removed. In some embodiments, the wire is then advanced to the stenotic level and may itself serve as a radiopaque guide for the posterior boundary of the epidural space. In other embodiments, a membrane is placed instead of the wire. The membrane includes metal or polymer materials. In exemplary embodiments, the membrane is radiopaque. In some embodiments, the protective membrane has a width in a range from 1 to 7 mm. In some embodiments, the membrane has a thickness of less than a millimeter. In some embodiments, the width and thickness dimensions can be selected to provide the membrane with sufficient rigidity to negotiate the stenotic segment without deforming or folding. In various embodiments, the membrane can be placed at the midline and serve as a guideline for decompression of both lateral sides with a single membrane placement or can be placed only on one lateral side at a time during decompression of that side. In exemplary embodiments, the membrane can serve a protective function by protecting the dura mater and nerves from heat, vibrational energy, and mechanical energy. In some embodiments, the wire, sheath, or shield can be substantially similar to or can include the shield 2610 or membrane 2613 described above with respect to FIGS. 34A-35B.

Figure 37:
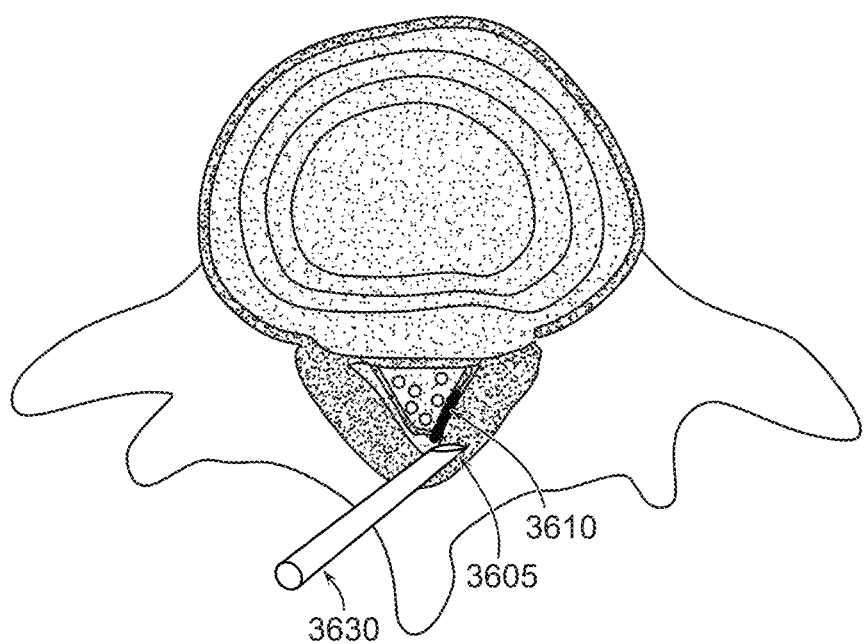

FIG. 37 illustrates contralateral introduction of an introducer tool 3630. As described below in greater detail, the contralateral oblique view is advantageous for visualization and placement of the introducer tool and decompression tool. In exemplary embodiments, the contralateral oblique (CLO) view is acquired at an angle of 35-45 degrees oblique from the antero-posterior view and to the opposite side to be decompressed. Further details concerning the advantages for the use of the CLO view are described in the publication by Jatinder S. Gill, M D, et al., "Contralateral Oblique View Is Superior To The Lateral View For Lumbar Epidural Access", Pain Medicine (2016) 17:839-850, the entire contents of which is incorporated herein by reference. In some embodiments, the angle is based on initial magnetic resonance imaging (MRI) and does not exceed 45 degrees. In the CLO view, a line termed the ventral interlaminar line (VILL) may be visualized as connecting the front margins of the laminae. Even in the absence of the shield, a surgical instrument placed behind (i.e., generally posterior to) the VILL is in a safe area and can access the ligament and the bone. The insertion point of the decompression tool is identified between the laminae on the CLO view and behind the VILL, usually several centimeters from the midline and at the same vertebral level as the stenosis. In some embodiments, the contralateral location of the insertion point can depend upon patient size. A sharp introducer tool 3630 can be advanced from the contralateral side up to a location 3605 at the middle of the spine, i.e., the spinolaminar junction. The tool is then advanced to the location 3604 of maximal insertion for stenosis decompression. If resistance is encountered during insertion of the introducer tool to the location 3604, the tool can be gently tapped in by a distance of 1 to 4 cm until bone is contacted. In various embodiments, a diameter of the introducer tool 3630 is in a range from 2 mm to 6 mm. In various embodiments, the introducer tool 3630 is of sufficient rigidity to allow motion or tilting at the spinolaminar junction by pushing on the proximal end. This motion or tilting allows decompression in multiple superior to inferior planes. In some embodiments, the introducer tool 3630 includes a sharp stylet to pierce hard tissue. In some embodiments, the introducer tool 3630 includes a small drill, ultrasonic bone shaver, or other decompression tool to remove hard tissue such as bone if the introducer tool cannot otherwise advance beyond the location 3605 at the spinolaminar junction. After the introducer tool 3630 has been advanced to the location of maximal extent, the introducer tool 3630 can be withdrawn to the midline. While the introducer tool 3630 is advanced and withdrawn, visualization is performed in the CLO view to ensure that the tool stays behind the VILL or, if a membrane is used, on one side of the membrane.

Figure 38:
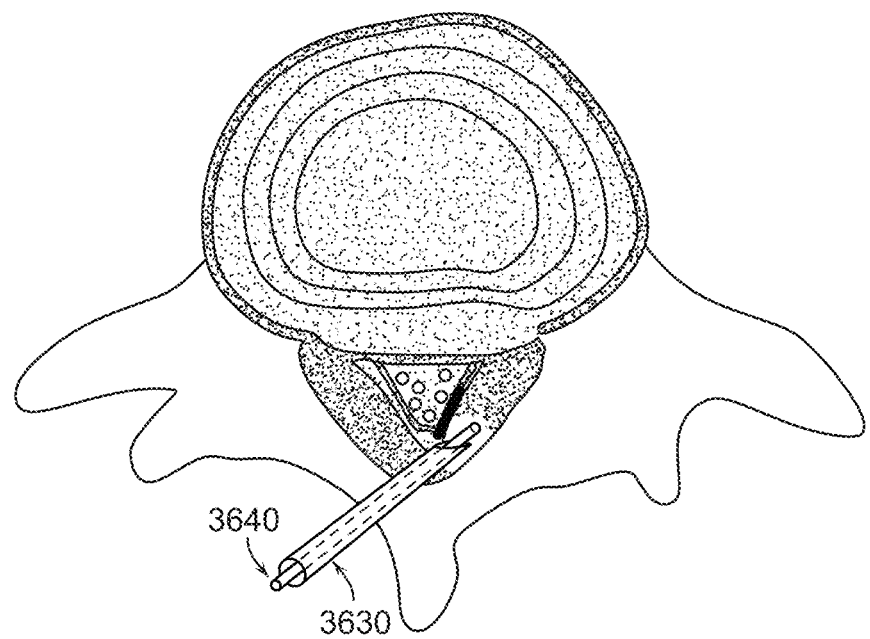

FIG. 38 illustrates initial stages of removal of ligamentum flavum as the decompression tool 3640 is advanced. The decompression tool 3640 can be inserted through the introducer tool 3630 and can be activated to sequentially decompress the area. Decompression using the decompression tool 3640 can be performed using fluoroscopic visualization (e.g., CLO view or other angle view) or using direct visualization with an imaging device optically coupled to a sensor at the distal end of the decompression tool 2640 or introducer tool 3630. In different embodiments, the direct visualization can be intermittent (i.e., alternation between visualization steps and decompression steps) or continuous (i.e., visualization can be performed during decompression). In some embodiments, the decompression tool 3640 or introducer tool 3630 includes a small camera or other imaging device at the distal end to enable direct visualization as described in conjunction with other embodiments herein. The decompression tool 3640 can utilize one or more techniques to ablate, debulk, or remove tissue. In some embodiments, the decompression tool 3640 can include mechanical withdrawal of tissue in stages or continuously using a withdrawal mechanism such as an Archimedes screw. In some embodiments, the decompression tool 3640 can include an ultrasonic decompressor or aspirator. The ultrasonic aspirator uses ultrasonic frequency vibration to dissect/remove tissue that can then be emulsified under irrigation. Aspiration then removes the emulsified tissue. In some embodiments, the decompression tool 3640 can include a laser ablation device or a quantum molecular resonance based removal device.

Figure 39:
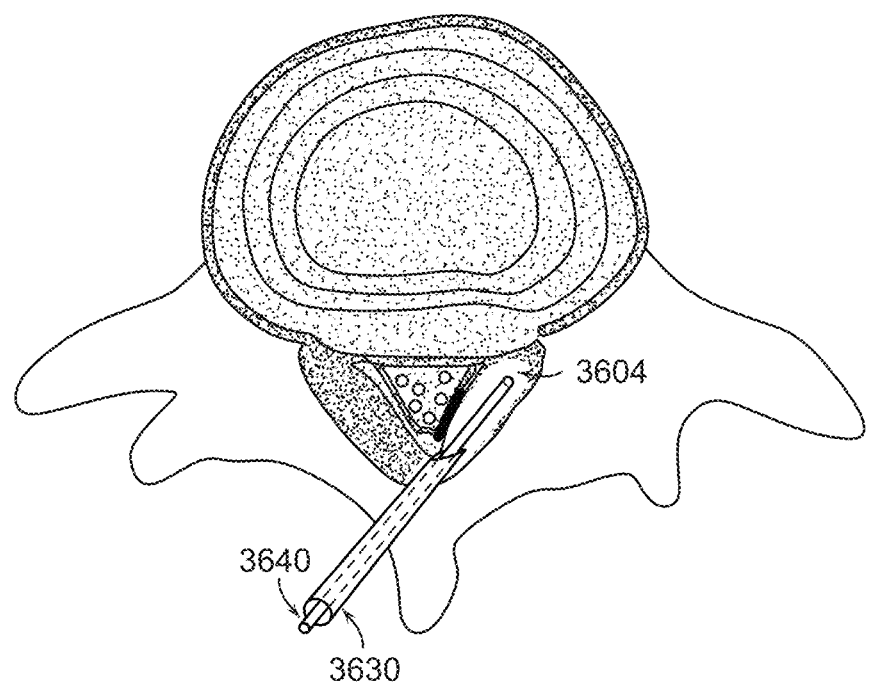

FIG. 39 illustrates further insertion of the decompression tool and additional removal of ligamentum flavum all the way to the superior articular process and dorsal lateral recess at location 3604. In this same plane, the tool may also be advanced into the foramen to accomplish a foraminotomy.

After the decompression tool has advanced from location 3605 to location 3604 in a particular plane, additional tissue removal can be done in other plane. The introducer tool can be directed cephalad or caudad at the spinolaminar junction (location 3604), and the decompression tool can be advanced as described above in a new plane that is cephalad or caudad, respectively, with respect to the initial removal. In some embodiments, the spinolaminar junction may function as a fulcrum to mobilize the decompression tool in the craniocaudal plane. In addition to the ligament, parts of the edges of the laminae may also be thus removed effectively accomplishing a functional laminectomy. Additional discussion of tissue removal in multiple planes appears below in relation to FIG. 51.

Figure 40:
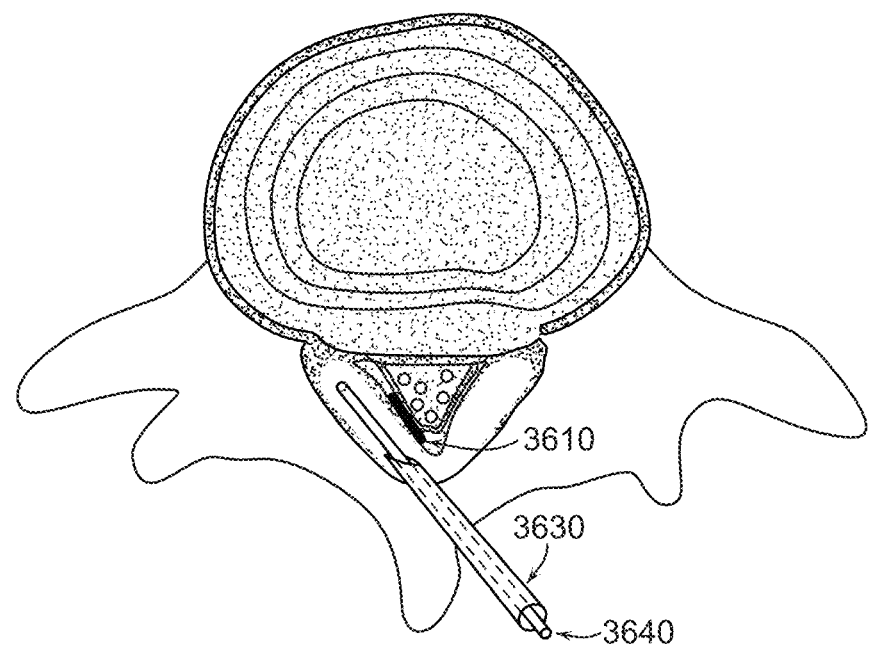
Figure 41:
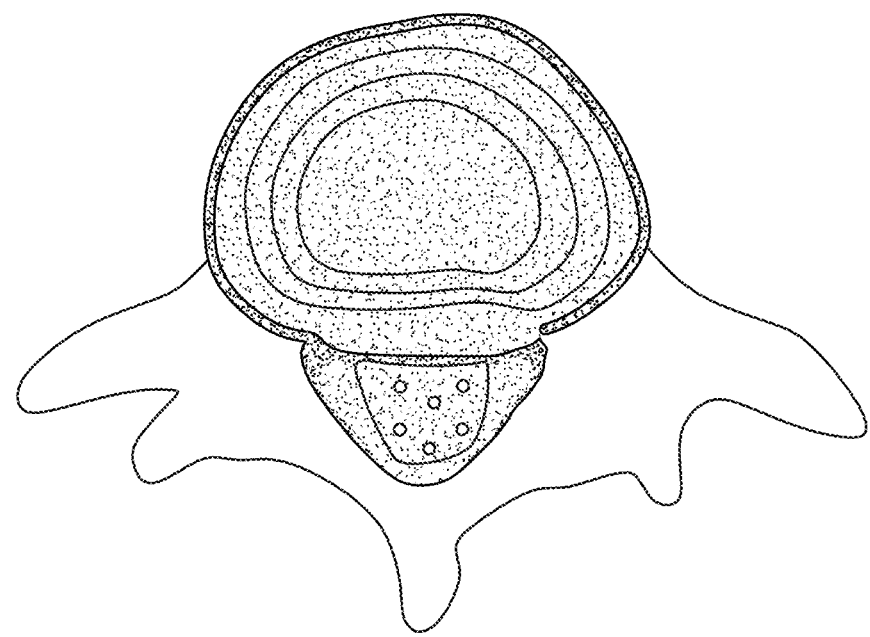

FIG. 40 illustrates placement of the shield member 3610 on the opposite lateral side and removal of ligamentum flavum by opposite contralateral insertion of the decompression tool 3640. The membrane may also be placed in the midline serving as a landmark for both sides to be decompressed without the need to place the membrane additional times. As shown in FIG. 41, upon removal of the tool there is expansion of the now decompressed epidural column into space vacated by the ligamentum flavum after the procedure is concluded. The nerves and cerebral spinal fluid (CSF) in the spinal canal can re-expand and reoccupy the newly opened area based upon how much tissue is removed by the decompression tool.

Figure 42:
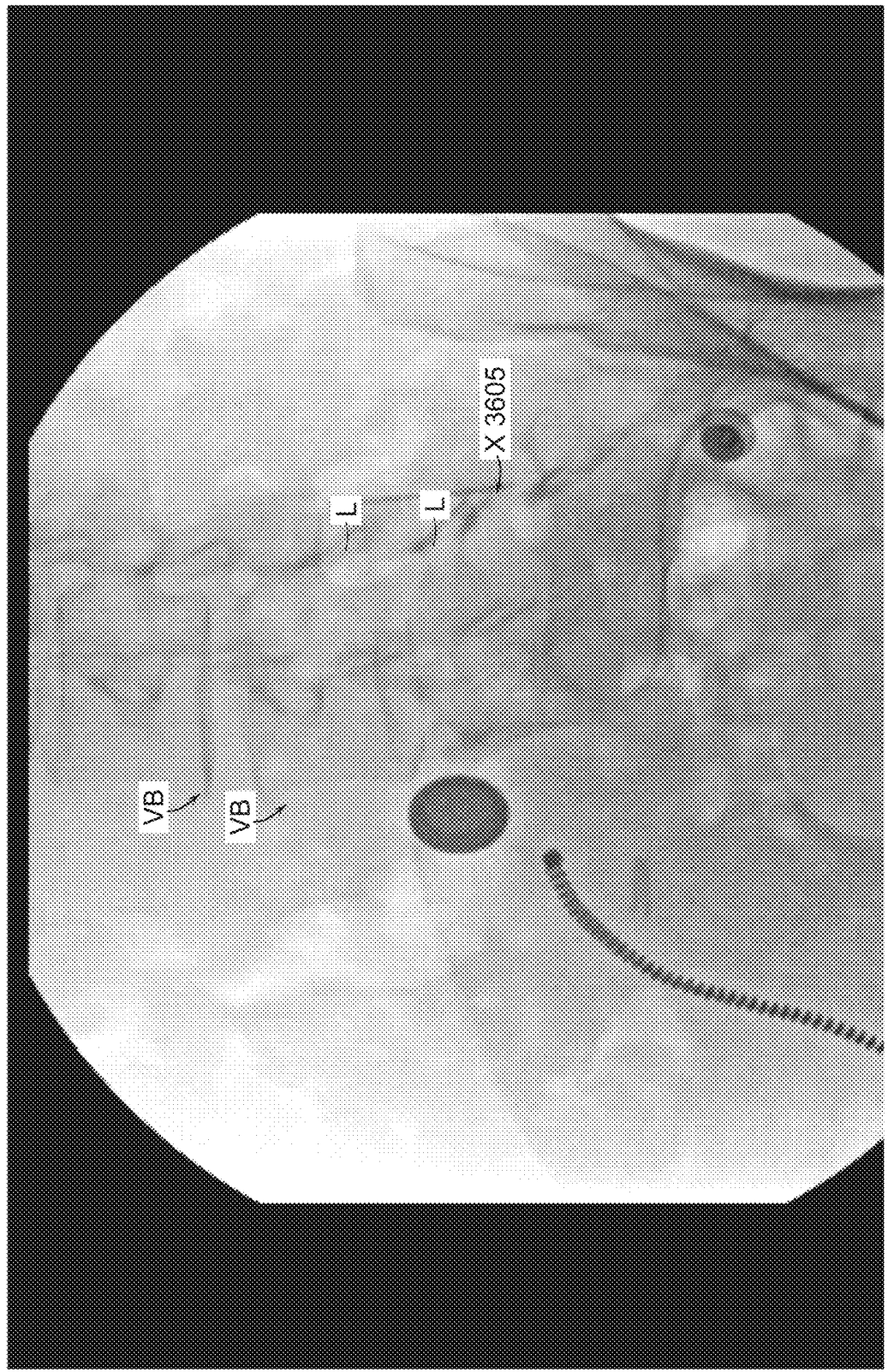
FIG. 42 illustrates an x-ray image taken from the contralateral oblique (CLO) view.

FIG. 42 illustrates an x-ray image of a spine taken from the contralateral oblique (CLO) view. The laminae L are seen with respect to each vertebral body VB. Between neighboring vertebrae, a small gap X exists between the laminae where a tool may be inserted to debulk ligamentum flavum, laminae, or foramen that are causing a stenosis.

Figure 43:
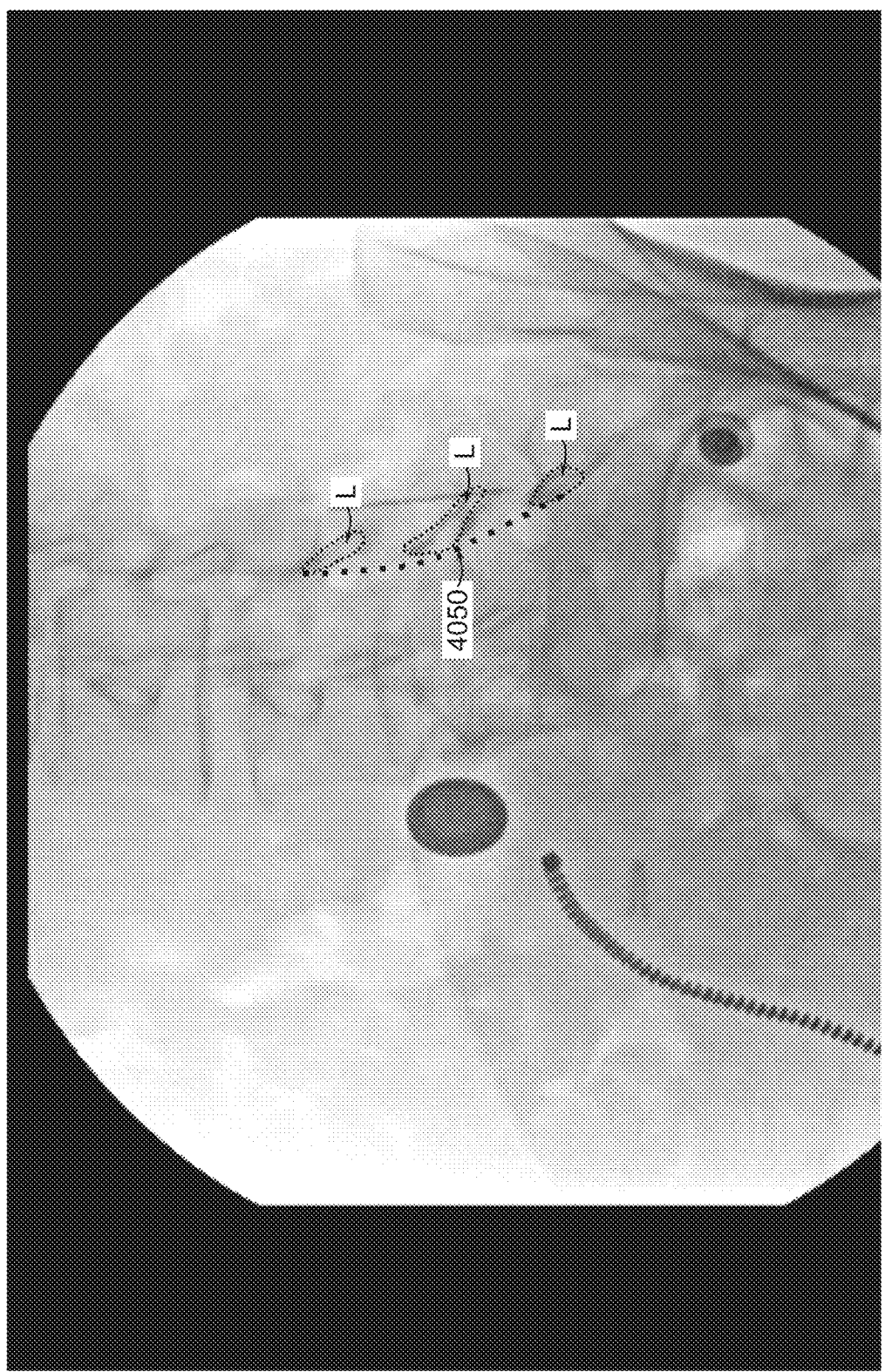
FIG. 43 illustrates an x-ray image in the CLO view highlighting the laminae and the ventral margin of the laminae.

FIG. 43 illustrates an x-ray image in the CLO view highlighting the laminae and the ventral margin of the laminae. In the CLO view, a projection of the laminae L of each vertebra can be seen. A curved line passing through the point at the ventral-most edge of each of the projected laminae in the CLO view is the ventral interlaminar line (VILL) 4050. The VILL 4050 as visualized from an angle of 45 degrees or less with respect to the midline represents the safe line behind which an operator of a decompression tool can be assured that the tool will not come in contact with the thecal sac or other sensitive structures in the epidural space.

Figure 44:
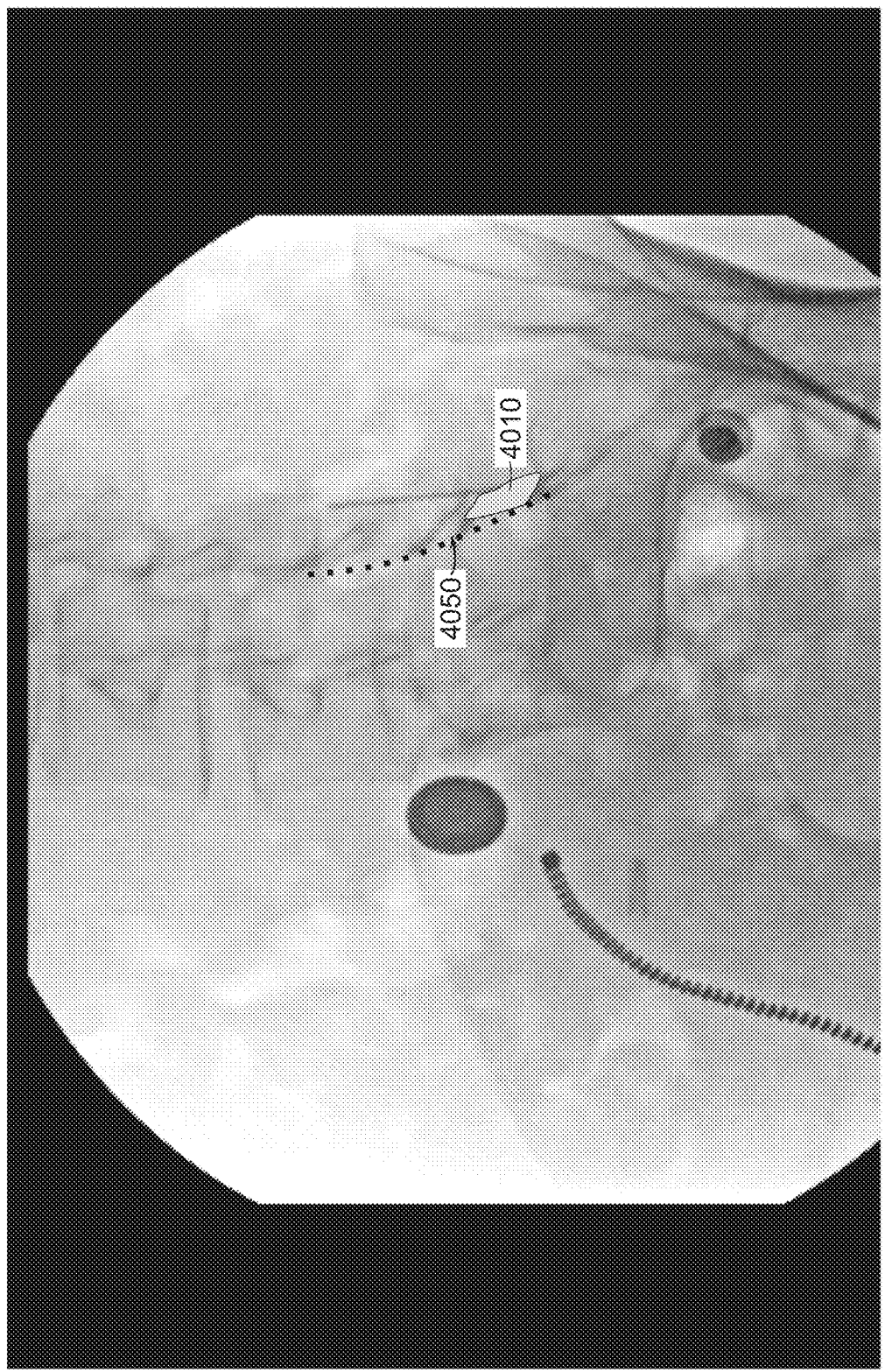
FIG. 44 illustrates an x-ray image in the CLO view showing the relationship between normal ligamentum flavum and the ventral interlaminar line (VILL).

FIG. 44 illustrates an x-ray image in the CLO view showing the relationship between normal ligamentum flavum 4010 and the ventral interlaminar line (VILL) 4050. The ligamentum flavum connects the two laminae (in this image, the lamina of the fifth lumbar vertebra and lamina of the first sacral vertebra). The epidural space lies in front of the VILL 4050 connecting the ventral (i.e., anterior) margins of the laminae A normal ligamentum flavum 4010 lies almost entirely posterior to the VILL.

Figure 45:
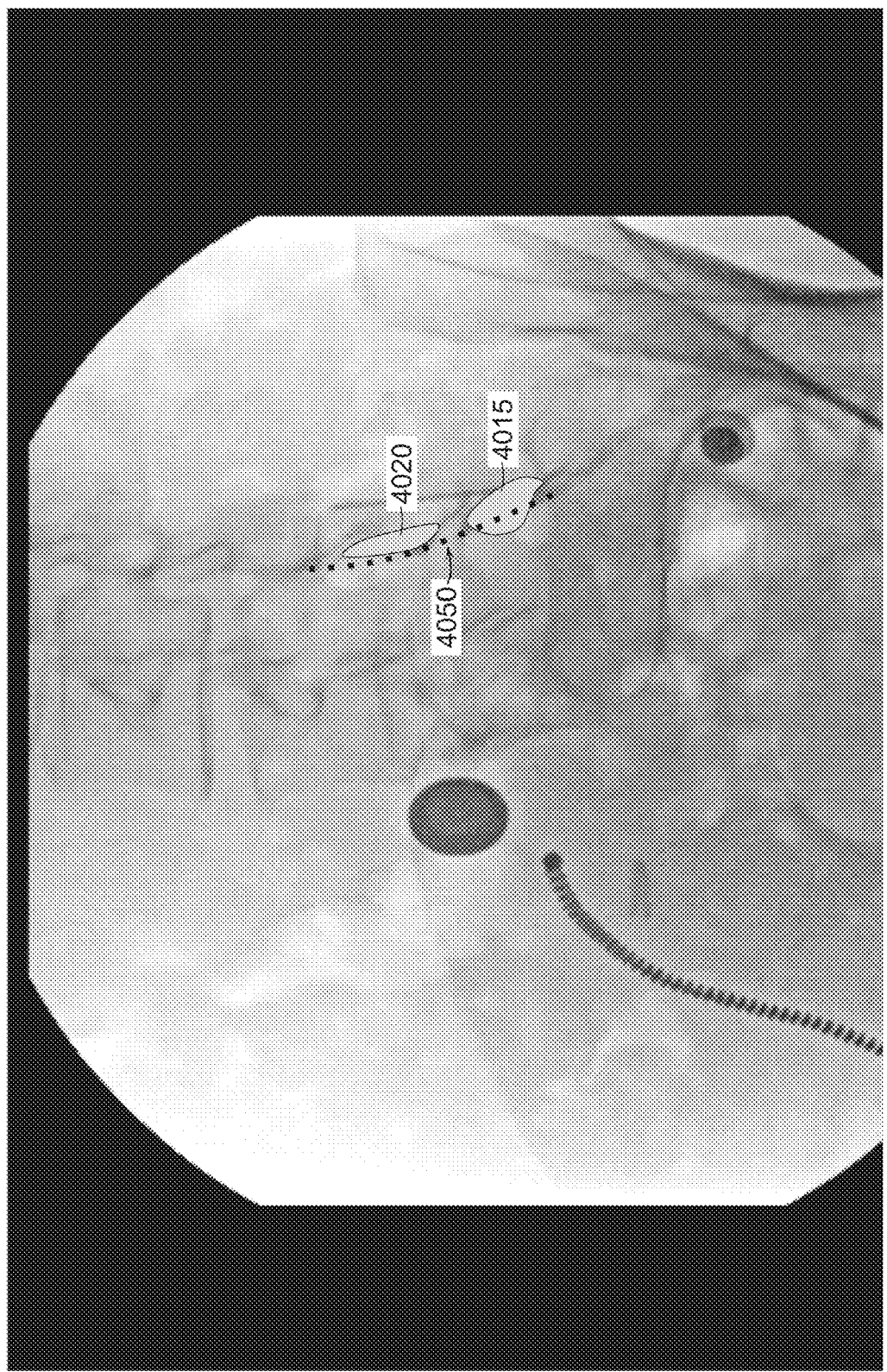
FIG. 45 illustrates an x-ray image in the CLO view showing the relationship between abnormal ligamentum flavum and the VILL.

FIG. 45 illustrates an x-ray image in the CLO view showing the relationship between abnormal ligamentum flavum and the VILL 4050. The ligamentum flavum 4015 connecting the fifth lumbar and first sacral vertebrae is abnormal while the ligamentum flavum 4020 connecting the fourth lumbar and fifth lumbar vertebrae is normal. As can be seen, the ligamentum flavum 4015 protrudes into the spinal canal and encroaches on the VILL 4050.

Figure 46:
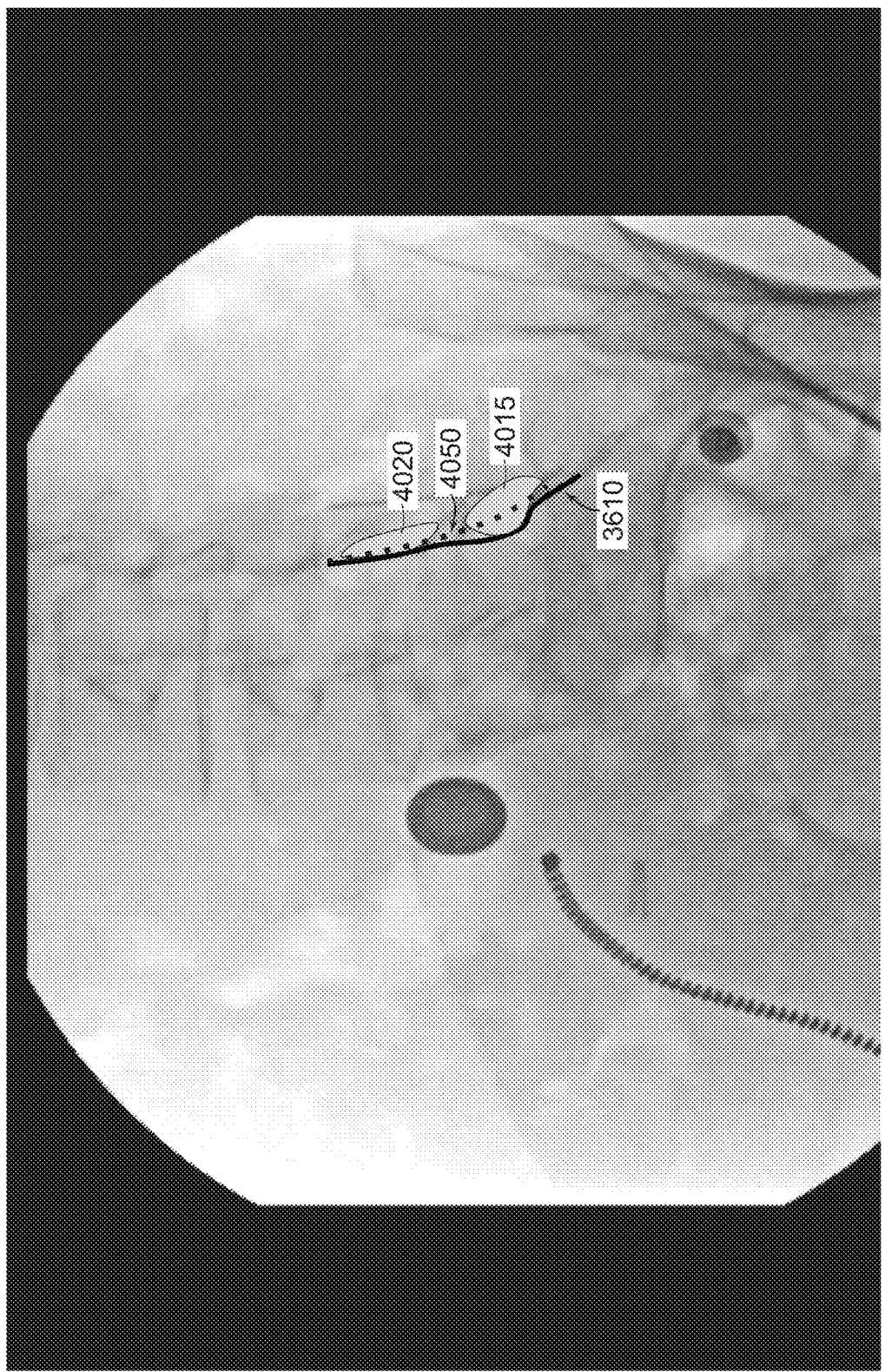
FIG. 46 illustrates an x-ray image in the CLO view showing a radiopaque shield inserted into the epidural space against the ventral edge of the ligamentum.

FIG. 46 illustrates an x-ray image in the CLO view showing a radiopaque protective membrane inserted into the epidural space against the ventral edge of the ligamentum. The membrane outlines the margin of the epidural space and/or the ventral edge of each ligamentum flavum 4015, 4020. As described previously, the membrane can provide a physical barrier between the ligamentum flavum and delicate tissues in the spinal canal. As such, the membrane protects the delicate structures from mechanical, electrical, or heating effects produced by the decompression process.

Figure 47:
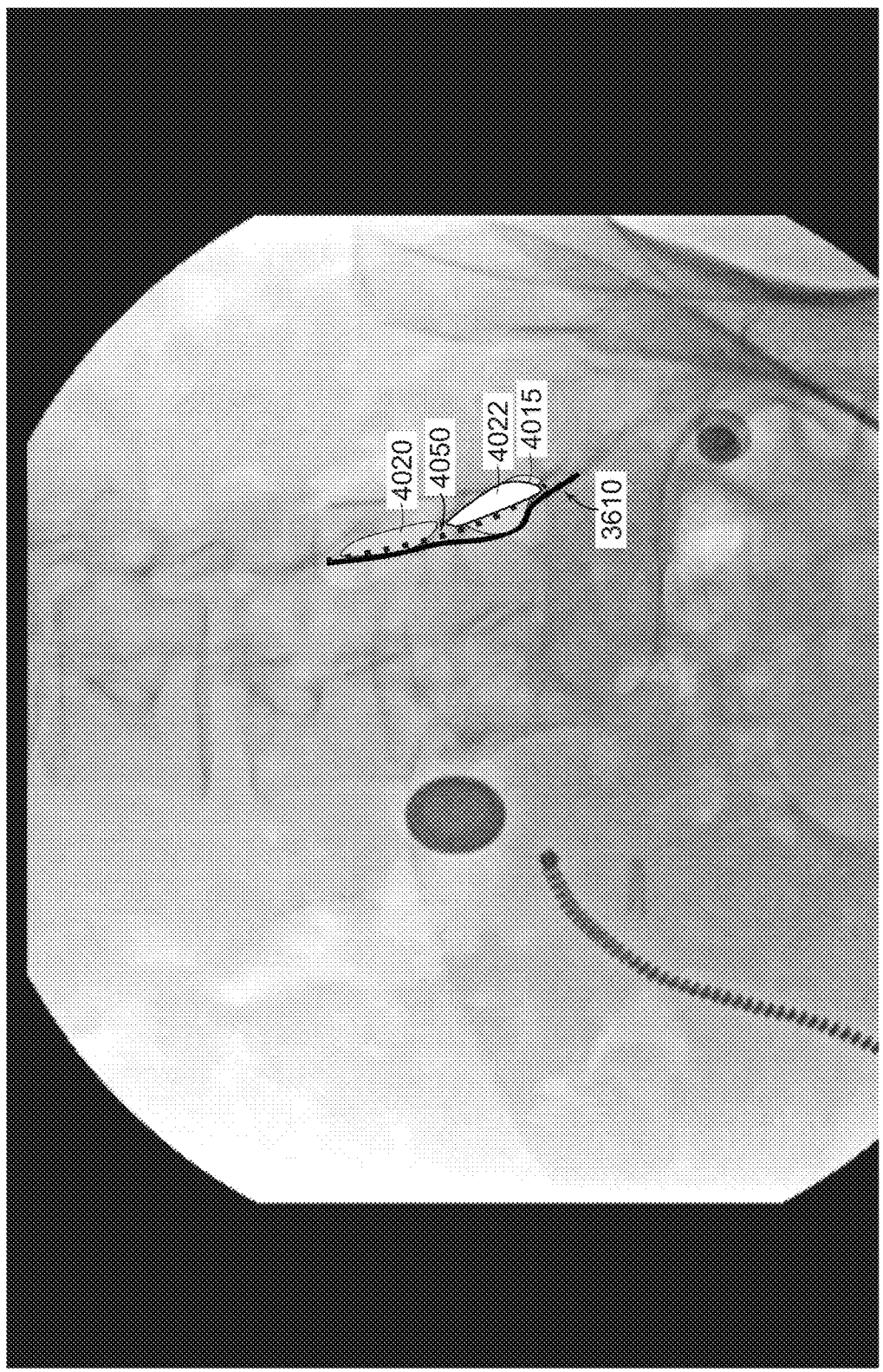
FIG. 47 illustrates an x-ray image in the CLO view illustrating the portion of the ligamentum that can safely be debulked even in the absence of a shield.

FIG. 47 illustrates an x-ray image in the CLO view at 45 degrees or less illustrating the portion of the ligamentum that can safely be debulked even in the absence of a shield. Although FIG. 47 shows a membrane in place, not all procedures must utilize a membrane to ensure safety of delicate structures such as nerves in the spinal canal. The portion 4022 of the ligamentum flavum 4015 and adjoining laminae posterior to the VILL 4050 can safely be removed in various embodiments of the present application. Because the practitioner can be assured that the delicate structures will not be found posterior to the VILL, any application of energy to remove tissue in this space does not affect the delicate tissue. In embodiments where a membrane is placed, additional decompression may be conducted anterior to the VILL 4050 but posterior to the membrane. Nonetheless, in many cases, the effect of removing the portion 4022 of the ligamentum flavum and adjoining laminae posterior to the VILL 4050 achieves sufficient debulking to relieve the stenosis. The membrane can be inserted without the need for an introducer, dilator or other spring member in some embodiments thereby simplifying the procedure.

Figure 48:
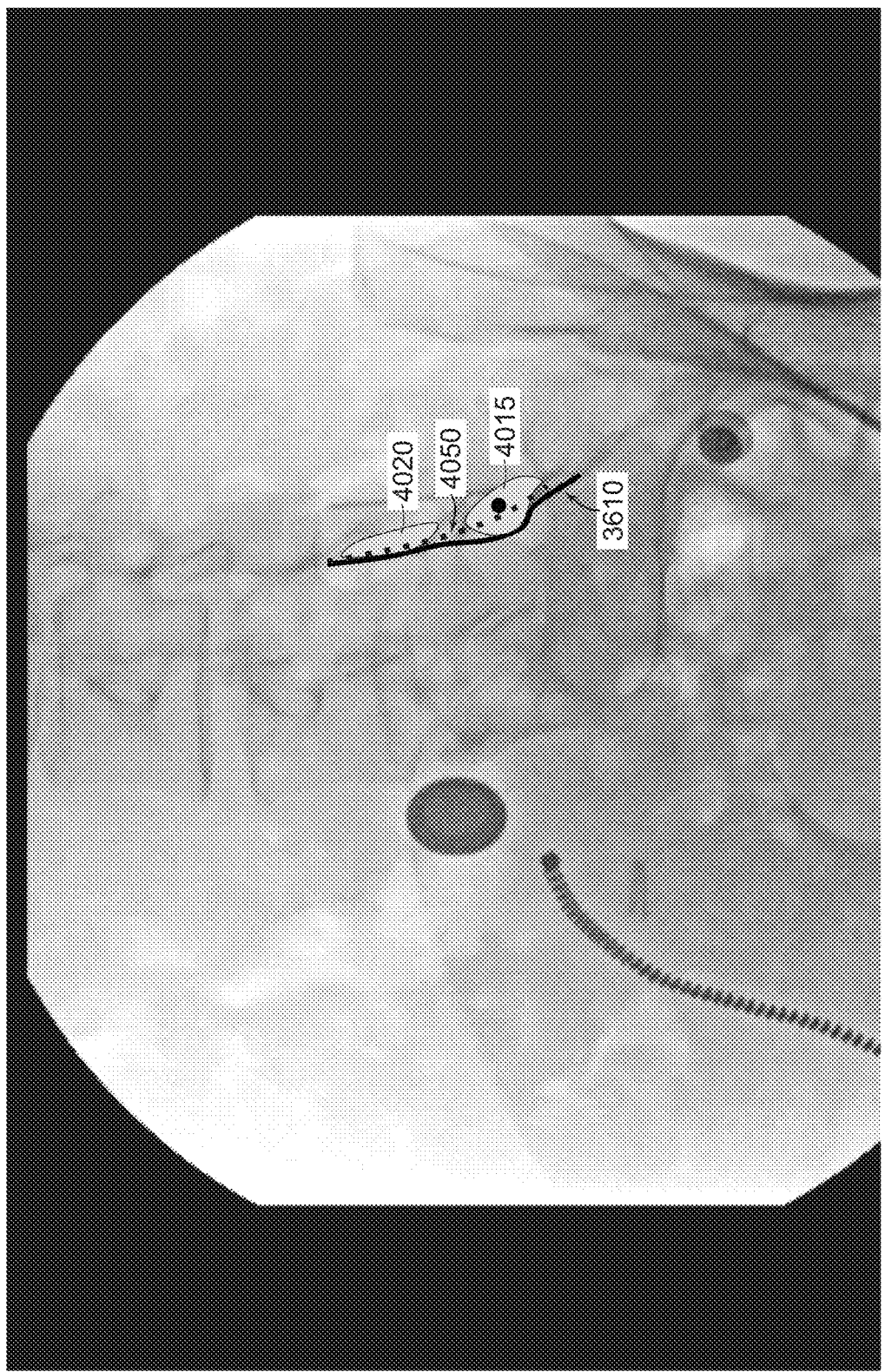
FIG. 48 illustrates an x-ray image in the CLO view illustrating the point of insertion of an introducer tool from the contralateral side.
Figure 50:
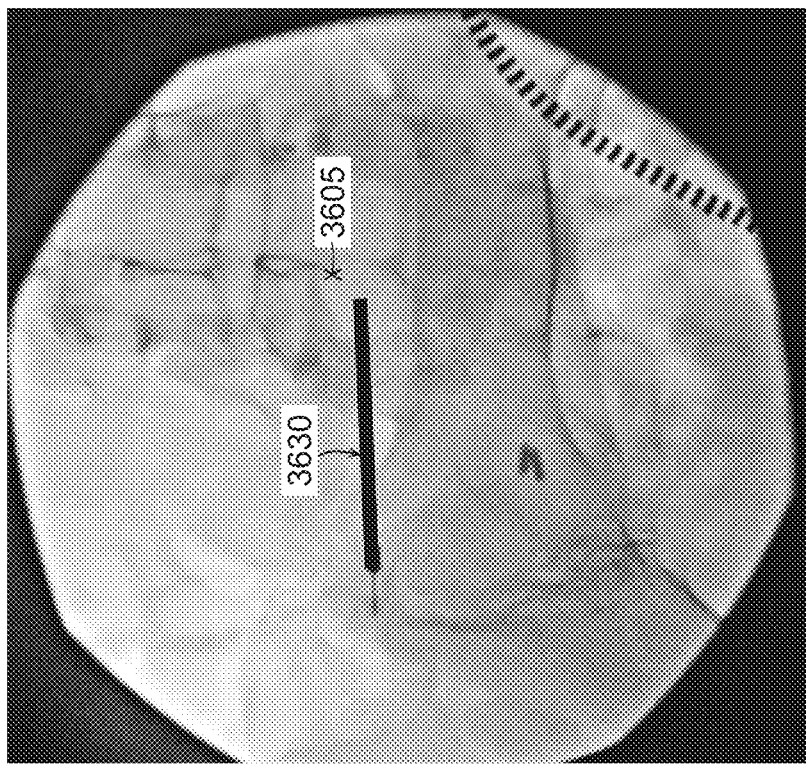
FIG. 50 illustrates an x-ray image in the antero-posterior projection view of the same region shown in FIG. 49.
Figure 49:
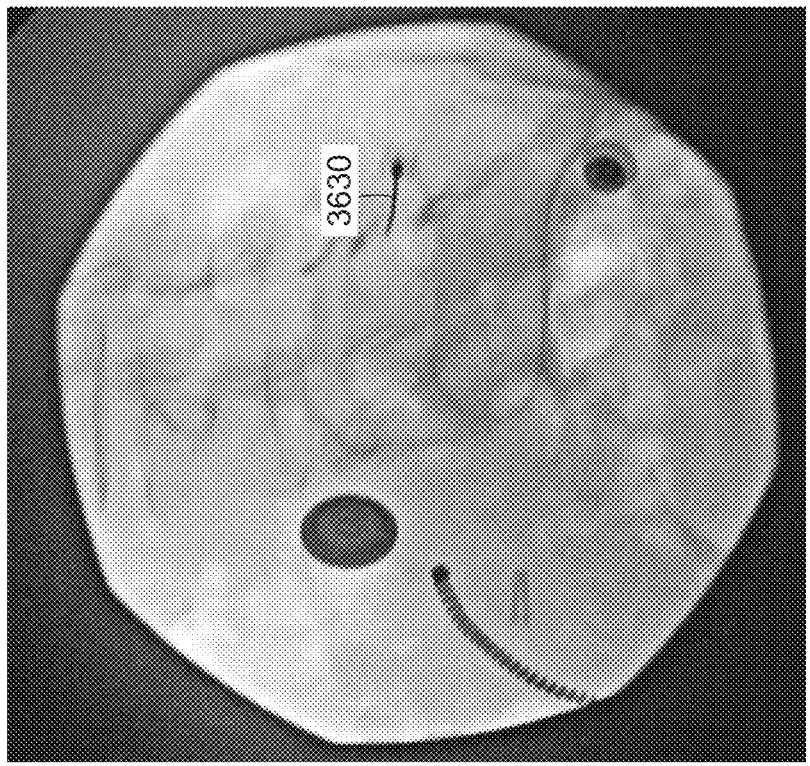
FIG. 49 illustrates an x-ray image in the CLO view showing advancement of the introducer tool.

FIG. 48 illustrates an x-ray image in the CLO view at 45 degrees or less illustrating the point of insertion of the introducer tool from the contralateral side. FIG. 49 illustrates an x-ray image in the CLO view showing advancement of the introducer tool. FIG. 50 illustrates an x-ray image in the antero-posterior projection view of the same region shown in FIG. 49. As described above in relation to FIGS. 36-41, the introducer tool 3630 may be used to introduce the compression tool between the laminae to allow for debulking and decompression to be conducted. The introducer tool 3630 is advanced in CLO and antero-posterior (AP) projection views. Upon insertion through the skin, the introducer tool 3630 generally contacts bone at the midline point 3605. In some embodiments, slight tapping or drilling may be needed to advance the introducer between laminae and to the opposite side without breaching the VILL 4050.

Figure 51:
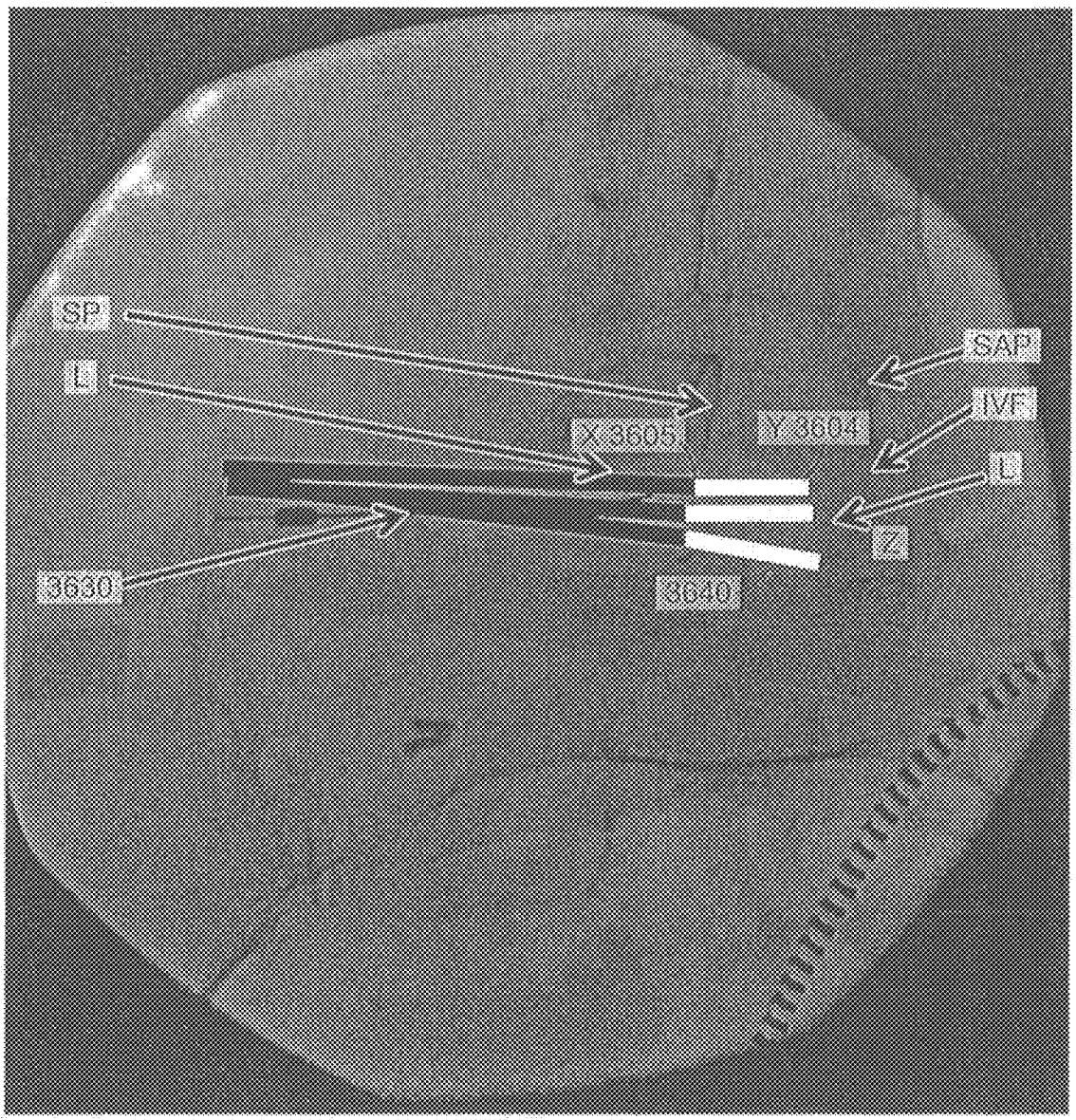
FIG. 51 illustrates an x-ray image in the AP view showing advancement of the decompression tool in multiple superior and inferior planes.

FIG. 51 illustrates an x-ray image in the AP view showing advancement of the decompression tool in multiple superior and inferior planes. The intravertabral foramen IVF and superior articulate process SAP are indicated. The introducer tool 3630 is advanced from the contralateral side and contacts the midline at the spinolaminar junction (position X, 3605), where bone may be contacted. If the introducer tool 3630 contacts bone, the introducer tool 3630 can be gently tapped and advanced to position Y where the superior articulate process SAP is contacted. Decompression can be carried out between position X and position Y in multiple superior and inferior planes. In the case where the foramen is causing stenosis, the introducer tool 3630 can be advanced beyond the position y to position z, which is the foramen, under vision.

Figure 52:
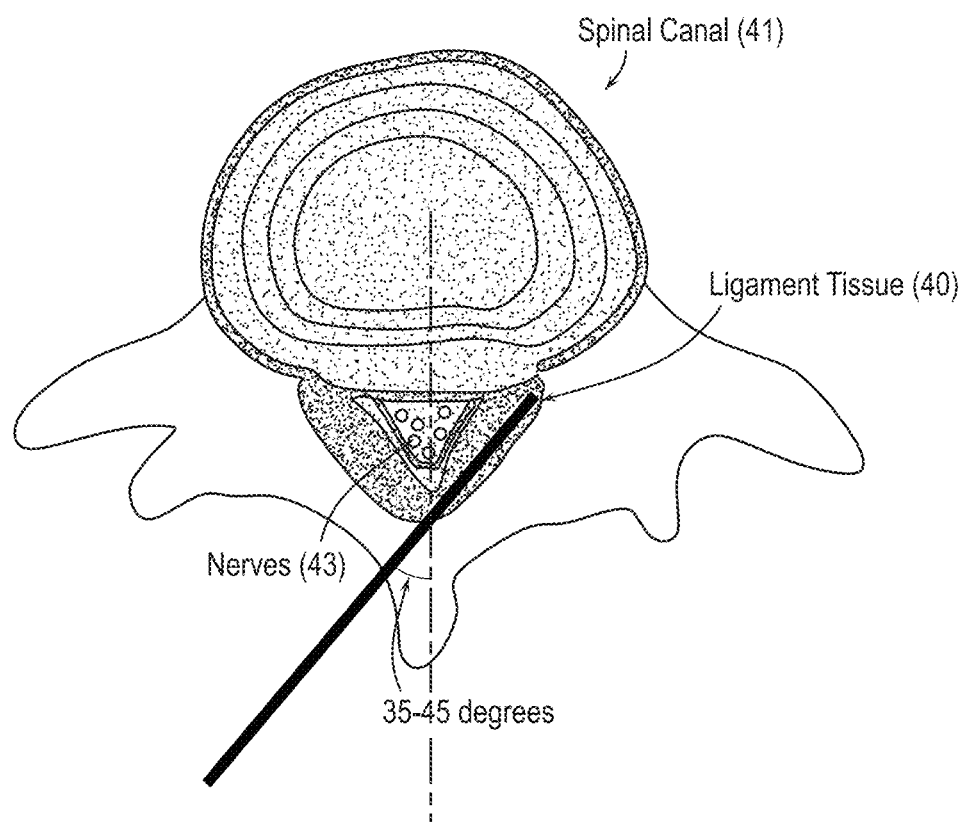
FIG. 52 illustrates a transverse view of advancement of the introducer tool or decompression tool from the contralateral side at an angle with respect to the midline.

FIG. 52 illustrates a transverse view of advancement of the introducer tool or decompression tool from the contralateral side at an angle with respect to the midline. By placing the tool at an angle in a range from 35 to 45 degrees with respect to the midline, the tool can debulk and remove ligament tissue 40 (ligamentum flavum) that is causing stenosis (compression of the nerves 43) while avoiding coming into contact with the nerves 43 or the spinal canal 41. The angle used in the contralateral oblique view may not exceed 45 degrees with respect to the midplane/midline of the patient; however, lesser angles may be used based upon the MRI and when a membrane is present and can be used as a guide.

The surgical tools for the removal of tissue as described herein can comprise a device such as that described in U.S. patent application Ser. No. 10/093,774, filed on Mar. 8, 2002 and published as U.S. Patent Application Publication 2002/0138091, the entire contents of which is incorporated herein by reference, wherein a rotating helical element or screw (e.g., Archimedes screw) extending from a tube or cannula is inserted percutaneously to remove a spinal stenosis as described herein. A motor is used to turn the thread at a speed sufficient to cut the tissue and remove it through the tube under suction. In a further embodiment, an ultrasonic aspirator such as a Sonopet® available from Stryker Corporation using soft tips or a bone cutting tip can be used to remove stenotic tissue as described herein.

Other embodiments will be apparent to those skilled in the art from consideration of the specification and practice of this disclosure. It is intended that the specification and examples be considered as exemplary only, with the true scope and spirit of the disclosed devices and methods being indicated by the following claims.

The invention claimed is:

1. A device for surgical removal of a spinal stenosis, comprising:
   a membrane having a size that can be inserted into an epidural space from a non-treatment level at a percutaneous insertion location along a spine of a patient between duramater and ligamentum flavum;
   a tissue removal device having a distal end to be inserted into the patient from a contralateral oblique angle that extends across a midline of the spine along a treatment level relative to the spine at a treatment location different from the insertion location such that the distal end is directed to a position to remove the spinal stenosis; and
   a fluoroscopic visualization device positioned to image a field of view along the contralateral oblique angle including a position of the membrane, the spinal stenosis and the tissue removal device.

2. The device of claim 1 further comprising a further imaging device to image a body region to be treated with the tissue removal device.

3. The device of claim 1 wherein the tissue removal device comprises at least one of a mechanical cutter, laser, an ultrasonic tool, or an Archimedes decompressing screw.

4. The device of claim 2 wherein the further imaging device comprises a camera and a guide light source that illuminates a region of tissue such that a user can identify a region of tissue for ablation.

5. The device of claim 1 wherein the membrane comprises a metal.

6. The device of claim 1 wherein the membrane comprises nitinol.

7. The device of claim 1 wherein the membrane comprises a polymer.

8. The device of claim 1 wherein the membrane comprises a composite structure including a polymer.

9. The device of claim 1 wherein the membrane is configured for placement adjacent a thecal sac in a spinal region of a patient.

10. The device of claim 1 wherein the membrane has a material and thickness to prevent delivery to the duramater of at least some energy delivered to other tissues.

11. The device of claim 2 wherein the tissue removal device further comprises the further imaging device positioned within a tubular body having a working channel through which the tissue removal device is inserted.

12. The device of claim 11 wherein the tubular body further comprises a suction device or a distally mounted dilator to expand a field of view.

13. The device of claim 12 wherein the suction device includes an ultrasonic suction tool or a decompressor tool that works on the principle of the Archimedes screw.

14. The device of claim 1 wherein the membrane has a thickness in a range from 100 microns to 2 millimeters, a length, and a width in a range of 1 to 6 millimeters.

15. A method for treating a spinal stenosis comprising:
   inserting a membrane from a non-treatment spinal level at an insertion location, the membrane having a distal end that protects duramater tissue during removal of a spinal stenosis along a spinal region of a spine of a patient;
   introducing a tubular body into the spinal region at a treatment level of the spine along a contralateral oblique axis extending across a midline of the spine such that the tubular body is inserted at a different location than the insertion location of the membrane, and thereby positioning a distal end of the tubular body into a spinal stenosis area;
   fluoroscopically visualizing the spinal stenosis area along the contralateral oblique axis to view a tissue removal device inserted through the tubular body and the membrane in the spinal region; and
   removing tissue from the spinal stenosis area as the tissue removal device is inserted along one side of the membrane.

16. The method of claim 15 wherein introducing the tubular body occurs under fluoroscopic visualization.

17. The method of claim 15 further comprising inserting a cutting tool through the tubular body.

18. The method of claim 15 further comprising removing at least a portion of tissue positioned in the epidural space from a spinal stenosis using at least one of manual removal or automated removal using an ultrasonic tool or a tool operating on the principle of the Archimedes screw.

19. The method of claim 15 wherein introducing the tubular body into the spinal region comprises percutaneously inserting the tubular body along a second contralateral oblique axis.

20. The method of claim 19, wherein inserting the tubular body occurs along axes with multiple superior and inferior orientations to compress the length of tissue in the spinal stenosis area and the bony edges of laminae in the spinal stenosis area.

21. The method of claim 15 wherein inserting the membrane from the non-treatment spinal level occurs along a sacral hiatus approach.

22. The method of claim 15 further comprising visualizing the epidural space with a detector and displaying an image.

23. The method of claim 15 further comprising visualizing insertion of the membrane under fluoroscopic examination.

24. The method of claim 15 wherein the membrane comprises a metal sheet having a planar or curved shape.

25. The method of claim 15 wherein the membrane comprises a nitinol sheet.

26. The method of claim 15 wherein the membrane comprises a polymer.

27. The method of claim 15 wherein the membrane comprises a composite material including a polymer.

28. A method for treating a spinal stenosis comprising:

introducing a tubular body into the spinal region along a contralateral oblique axis of a patient to access a spinal stenosis area, the contralateral oblique axis being in a range of 35 to 45 degrees offset from a midline of the spine of the patient such that a distal end of the tubular body is inserted across the midline and into a spinal stenosis while avoiding contact with nerves of the spinal canal;

fluoroscopically visualizing the spinal stenosis area and a tissue removal device inserted through the tubular body and into the spinal stenosis along the contralateral oblique axis; and removing tissue from the spinal stenosis as the tissue removal device is inserted sequentially and in multiple planes into the spinal stenosis.

29. The method of claim 28, further comprising positioning a membrane between the spinal stenosis and the nerves of the spinal canal.

30. The method of claim 28, wherein the tissue removal device is a manual tool and removing tissue includes manual removal of tissue or wherein the tissue removal device is an automated ultrasonic tool or a tool operating on the principle of the Archimedes screw and removing tissue includes automated removal of tissue.

31. The method of claim 28 further comprising using a bone cutting tool to remove bone for insertion of the tubular body into the spinal stenosis area.

32. The method of claim 28 wherein the tubular body is advanced from the contralateral side of the midline to contact a spinolaminar junction, the tubular body being advanced towards a spinal articulate process (SAP) and into the spinal stenosis.

* * * * *